(12) United States Patent
Hirohara et al.

(10) Patent No.: US 7,490,939 B2
(45) Date of Patent: Feb. 17, 2009

(54) EYE CHARACTERISTICS MEASURING SYSTEM

(75) Inventors: Yoko Hirohara, Tokyo (JP); Tatsuo Yamaguchi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 346 days.

(21) Appl. No.: 10/529,150

(22) PCT Filed: Sep. 25, 2003

(86) PCT No.: PCT/JP03/12203
§ 371 (c)(1), (2), (4) Date: Feb. 2, 2006

(87) PCT Pub. No.: WO2004/028355
PCT Pub. Date: Apr. 8, 2004

(65) Prior Publication Data
US 2006/0146285 A1    Jul. 6, 2006

(51) Int. Cl.
*A61B 3/10* (2006.01)
*A61B 3/14* (2006.01)

(52) U.S. Cl. .................. 351/205; 351/206; 351/208
(58) Field of Classification Search ......... 351/205–212, 351/243, 246, 233, 200
See application file for complete search history.

(56) References Cited

U.S. PATENT DOCUMENTS

| | | | |
|---|---|---|---|
| 6,042,233 A | 3/2000 | Mihashi et al. | 351/221 |
| 6,234,631 B1 | 5/2001 | Sarver et al. | 351/212 |
| 6,273,566 B1 | 8/2001 | Kobayashi et al. | 351/221 |
| 7,249,852 B2 * | 7/2007 | Mihashi et al. | 351/221 |
| 7,281,797 B2 * | 10/2007 | Yamaguchi et al. | 351/205 |
| 2002/0041359 A1 | 4/2002 | Mihashi et al. | 351/221 |

FOREIGN PATENT DOCUMENTS

| | | |
|---|---|---|
| EP | 1 113 251 A2 | 7/2001 |
| JP | 11-137522 A | 5/1999 |
| JP | 2001-095760 A | 4/2001 |
| JP | 2001-507258 A | 6/2001 |
| JP | 2001-321340 A | 11/2001 |
| WO | WO 98/27863 A1 | 7/1993 |

* cited by examiner

*Primary Examiner*—Mohammed Hasan
(74) *Attorney, Agent, or Firm*—Foley & Lardner LLP

(57) ABSTRACT

A first illuminating optical system illuminates an eye with a wide beam. A first light receiving unit receives reflection light fluxes from the eye that have been converted into at least 17 beams by a first conversion member. A first compensation optical unit, disposed in the first illuminating optical system, compensates an illuminating light flux to the eye for aberration. A second compensation optical unit, disposed in a first light receiving optical system, compensates a reflection light flux from the eye for aberration. An operation unit determines, based on an output from the first light receiving unit, a compensation amount for cancelling out aberration to deform the first and second compensation optical units and compensate for aberration. The operation unit determines the optical characteristics of the eye, based on an output from the first light receiving unit after compensation, and on compensated optical characteristics.

45 Claims, 46 Drawing Sheets

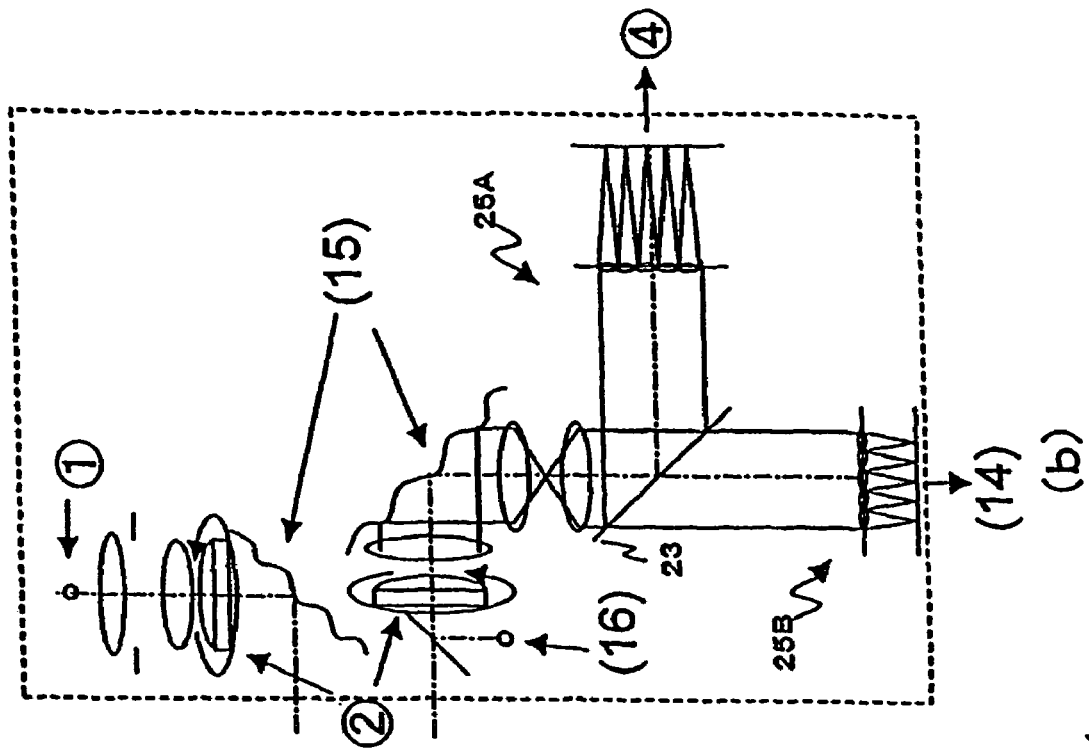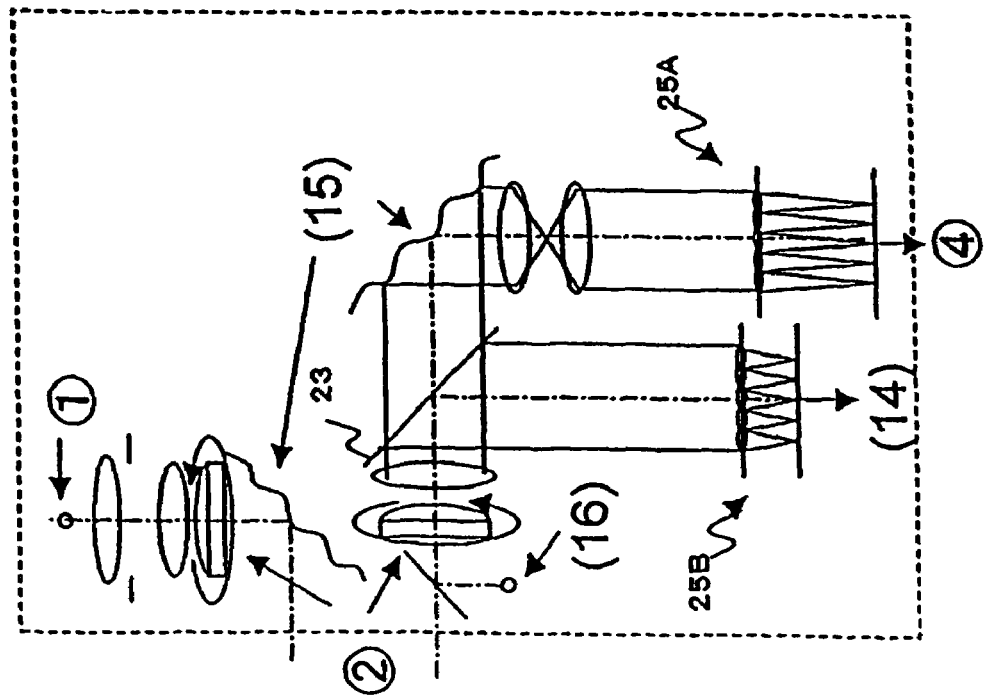
FIG.24

$$\begin{bmatrix}
i & 2j-i & \\
0 & 0 & 1 \\
1 & -1 & r\sin(t) \\
1 & 1 & \cos(t)\,r \\
2 & -2 & r^2\sin(2t) \\
2 & 0 & 2r^2-1 \\
2 & 2 & r^2\cos(2t) \\
3 & -3 & r^3\sin(3t) \\
3 & -1 & (3r^3-2r)\sin(t) \\
3 & 1 & (3r^3-2r)\cos(t) \\
3 & 3 & r^3\cos(3t) \\
4 & -4 & r^4\sin(4t) \\
4 & -2 & (4r^4-3r^2)\sin(2t) \\
4 & 0 & 6r^4-6r^2+1 \\
4 & 2 & (4r^4-3r^2)\cos(2t) \\
4 & 4 & r^4\cos(4t) \\
5 & -5 & r^5\sin(5t) \\
5 & -3 & (5r^5-4r^3)\sin(3t) \\
5 & -1 & (10r^5-12r^3+3r)\sin(t) \\
5 & 1 & (10r^5-12r^3+3r)\cos(t) \\
5 & 3 & (5r^5-4r^3)\cos(3t) \\
5 & 5 & r^5\cos(5t) \\
6 & -6 & r^6\sin(6t) \\
6 & -4 & (6r^6-5r^4)\sin(4t) \\
6 & -2 & (15r^6-20r^4+6r^2)\sin(2t) \\
6 & 0 & 20r^6-30r^4+12r^2-1 \\
6 & 2 & (15r^6-20r^4+6r^2)\cos(2t) \\
6 & 4 & (6r^6-5r^4)\cos(4t) \\
6 & 6 & r^6\cos(6t)
\end{bmatrix}$$

FIG.33

| i | 2j − i | |
|---|---|---|
| 0 | 0 | $1$ |
| 1 | −1 | $y$ |
| 1 | 1 | $x$ |
| 2 | −2 | $2yx$ |
| 2 | 0 | $2x^2 + 2y^2 - 1$ |
| 2 | 2 | $x^2 - y^2$ |
| 3 | −3 | $3yx^2 - y^3$ |
| 3 | −1 | $3yx^2 + 3y^3 - 2y$ |
| 3 | 1 | $3x^3 + 3xy^2 - 2x$ |
| 3 | 3 | $x^3 - 3xy^2$ |
| 4 | −4 | $4yx^3 - 4y^3 x$ |
| 4 | −2 | $8yx^3 + 8y^3 x - 6yx$ |
| 4 | 0 | $6x^4 + 12x^2 y^2 + 6y^4 - 6x^2 - 6y^2 + 1$ |
| 4 | 2 | $4x^4 - 4y^4 - 3x^2 + 3y^2$ |
| 4 | 4 | $x^4 - 6x^2 y^2 + y^4$ |
| 5 | −5 | $5yx^4 - 10y^3 x^2 + y^5$ |
| 5 | −3 | $15yx^4 + 10y^3 x^2 - 5y^5 - 12yx^2 + 4y^3$ |
| 5 | −1 | $10yx^4 + 20y^3 x^2 + 10y^5 - 12yx^2 - 12y^3 + 3y$ |
| 5 | 1 | $10x^5 + 20x^3 y^2 + 10xy^4 - 12x^3 - 12xy^2 + 3x$ |
| 5 | 3 | $5x^5 - 10x^3 y^2 - 15xy^4 - 4x^3 + 12xy^2$ |
| 5 | 5 | $x^5 - 10x^3 y^2 + 5xy^4$ |
| 6 | −6 | $6yx^5 - 20y^3 x^3 + 6y^5 x$ |
| 6 | −4 | $24yx^5 - 24y^5 x - 20yx^3 + 20y^3 x$ |
| 6 | −2 | $30yx^5 + 60y^3 x^3 + 30y^5 x - 40yx^3 - 40y^3 x + 12yx$ |
| 6 | 0 | $20x^6 + 60x^4 y^2 + 60x^2 y^4 + 20y^6 - 30x^4 - 60x^2 y^2 - 30y^4 + 12x^2 + 12y^2 - 1$ |
| 6 | 2 | $15x^6 + 15x^4 y^2 - 15x^2 y^4 - 15y^6 - 20x^4 + 20y^4 + 6x^2 - 6y^2$ |
| 6 | 4 | $6x^6 - 30x^4 y^2 - 30x^2 y^4 + 6y^6 - 5x^4 + 30x^2 y^2 - 5y^4$ |
| 6 | 6 | $x^6 - 15x^4 y^2 + 15x^2 y^4 - y^6$ |

FIG. 34

EYE CHARACTERISTICS MEASURING SYSTEM

TECHNICAL FIELD

The present invention relates to eye-characteristics measurement apparatuses, and more particularly, to an eye-characteristics measurement apparatus for precisely measuring the optical characteristics of an eye under measurement by using a wavefront sensor.

BACKGROUND ART

Recently, optical instruments used in the medical field have been spread. Especially in ophthalmology, optical-characteristics measurement apparatuses for checking eye functions such as the refraction and adjustment of eyes and the insides of eyeballs have been spread. For example, there exists a photorefractometer for obtaining the refractive power and the corneal shape of an eye under measurement.

A retina-image resolution improving apparatus for compensating for wave aberration by deforming a compensation optical member similar to a deformable mirror has been disclosed (for example, in PCT Japanese Translation Patent Publication No. 2001-507258). In this apparatus, laser light reflected from the retina of an eye forms a wavefront on the Hartmann-Shack wavefront sensor through a deformable mirror. The formed wavefront is digitized by a digital processor through a camera to measure wave aberration. The digital-data processor transmits a correction signal to be fed back to the deformable mirror, based on the measured wave aberration. The deformable mirror is deformed to compensate the eye for the wave aberration.

DISCLOSURE OF INVENTION

In apparatuses for measuring the optical characteristics of an eye under measurement having aberration, however, correct measurement is difficult in some cases due to much aberration. Especially, a secondary light source formed by collecting incident light on an eyeground has a bad light-collecting state due to much aberration, and therefore, the secondary light source blurs and spreads in some cases. Double-path measurement, which uses a wide (large-diameter) beam, is susceptible to the effect of aberration, and cannot be performed in some cases.

In view of the foregoing, an object of the present invention is to provide an eye-characteristics measurement apparatus having a wide measurement range and capable of performing correct measurement even if there is much aberration. In addition, another object of the present invention is to illuminate an eye under measurement in an appropriate illumination state. Further, another object of the present invention is to apply compensation to light incident on an eye under measurement to cancel aberration to remove the effect of the aberration on the incident light. An object of the present invention is to provide an eye-characteristics measurement apparatus for precisely measuring the optical characteristics of an eye under measurement by applying compensation to cancel aberration included in measurement light and further by measuring the amount of aberration after the compensation. An object of the present invention is to provide an eye-characteristics measurement apparatus for measuring optical characteristics more precisely and more quickly by applying compensation to cancel aberration included in measurement light and further by using low-sensitivity and high-sensitivity optical systems. Furthermore, an object of the present invention is to perform more correct measurement with the difference between a value input to cancel aberration and aberration actually compensated for being taken into account.

According to first solving means of this invention, there is provided an eye-characteristics measurement apparatus comprising:
a first light-source section for emitting a light beam having a first wavelength;
a first illumination optical system for illuminating a minute area on the retina of an eye under measurement, with a light beam emitted from the first light-source section;
a compensation optical section for compensating for aberration of a light beam transmitted or reflected, according to the amount of compensation given based on an optical characteristic of a reflected light beam which is reflected and returned from the retina of the eye under measurement;
a first light-receiving optical system for receiving a part of the reflected light beam which is reflected and returned from the retina of the eye under measurement, through the compensation optical section and a first conversion member having a long focal length or a high sensitivity for converting to at least substantially 17 beams;
a first light-receiving section for receiving a light beam received by the first light-receiving optical system;
a third light-source section for illuminating the compensation optical section with a light beam having a third wavelength;
a third light-receiving optical system for receiving a light beam emitted from the third light-source section, through the compensation optical section and a third conversion member for converting to at least substantially 17 beams;
a third light-receiving section for receiving a light beam received by the third light-receiving optical system;
a second light-receiving optical system for receiving a part of the reflected light beam which is reflected and returned from the retina of the eye under measurement, through the compensation optical section and a second conversion member having a short focal length, a low sensitivity, or a high density for converting to at least substantially 17 beams;
a second light-receiving section for receiving a light beam received by the second light-receiving optical system;
a compensation-amount calculation section for obtaining an optical characteristic of the eye under measurement based on the output of the second light-receiving section, for obtaining the amount of compensation based on the optical characteristic, and for outputting the amount of compensation to the compensation optical section; and
a measurement calculation section for measuring an optical characteristic compensated by the compensation optical section based on the output of the third light-receiving section and an optical characteristic based on the output of the first light-receiving section, obtained after the compensation of the compensation optical section, and for obtaining an optical characteristic of the eye under measurement according to the measured optical characteristics.

According to second solving means of this invention, there is provided an eye-characteristics measurement apparatus comprising:
a first light-source section for emitting a light beam having a first wavelength;
a first illumination optical system for illuminating a minute area on the retina of an eye under measurement, with a light beam emitted from the first light-source section;
a compensation optical section for compensating for aberration of a light beam transmitted or reflected, according to the amount of compensation given based on an optical characteristic of a reflected light beam which is reflected and returned from the retina of the eye under measurement;

a third light-source section for illuminating the compensation optical section with a light beam having a third wavelength;

a first light-receiving optical system for receiving a part of the reflected light beam which is reflected and returned from the retina of the eye under measurement and the light beam emitted from the third light-source section, through the compensation optical section and a first conversion member having a long focal length or a high sensitivity for converting to at least substantially 17 beams;

a first light-receiving section for receiving a light beam received by the first light-receiving optical system;

a second light-receiving optical system for receiving a part of the reflected light beam which is reflected and returned from the retina of the eye under measurement, through the compensation optical section and a second conversion member having a short focal length, a low sensitivity, or a high density for converting to at least substantially 17 beams;

a second light-receiving section for receiving a light beam received by the second light-receiving optical system;

a compensation-amount calculation section for obtaining an optical characteristic of the eye under measurement based on the output of the second light-receiving section, for obtaining the amount of compensation based on the optical characteristic, and for outputting the amount of compensation to the compensation optical section; and a measurement calculation section for measuring an optical characteristic compensated by the compensation optical section based on the output of the first light-receiving section caused by the light beam emitted from the third light-source section, for measuring an optical characteristic obtained after the compensation of the compensation optical section based on the output of the first light-receiving section caused by the light beam emitted from the first light-source section, and for obtaining an optical characteristic of the eye under measurement according to the measured optical characteristics.

According to third solving means of this invention, there is provided an eye-characteristics measurement apparatus comprising:

a first light-source section for emitting a light beam having a first wavelength;

a first illumination optical system for illuminating a minute area on the retina of an eye under measurement, with a light beam emitted from the first light-source section;

a first light-receiving optical system for receiving a part of a reflected light beam which is reflected and returned from the retina of the eye under measurement, through a first conversion member having a long focal length or a high sensitivity for converting to at least substantially 17 beams;

a second light-receiving optical system for receiving a part of the reflected light beam which is reflected and returned from the retina of the eye under measurement, through a second conversion member having a short focal length, a low sensitivity, or a high density for converting to at least substantially 17 beams;

a first light-receiving section for receiving a light beam received by the first light-receiving optical system;

a second light-receiving section for receiving a light beam received by the second light-receiving optical system;

a compensation-amount calculation section for obtaining an optical characteristic of the eye under measurement based on the output of the first light-receiving section and/or the second light-receiving section, and for obtaining and outputting the amount of compensation required to cancel aberration based on the optical characteristic;

a compensation optical section for applying aberration compensation based on the amount of compensation output from the compensation-amount calculation section to the reflected light beam from the retina of the eye under measurement, or to both an illumination light beam coming from the first illumination optical system and the reflected light beam from the retina of the eye under measurement; and a measurement calculation section for obtaining an optical characteristic of the eye under measurement according to an optical characteristic based on the output of the first light-receiving section and/or the second light-receiving section, obtained after the compensation of the compensation optical section, and an optical characteristic compensated by the compensation optical section.

According to fourth solving means of this invention, there is provided an eye-characteristics measurement apparatus comprising:

a first light-source section for emitting a light beam having a first wavelength;

a first illumination optical system for illuminating a minute area on the retina of an eye under measurement, with a light beam emitted from the first light-source section;

a first light-receiving optical system for receiving a part of a reflected light beam which is reflected and returned from the retina of the eye under measurement, through a first conversion member for converting to at least substantially 17 beams;

a first light-receiving section for receiving a light beam received by the first light-receiving optical system;

a second light-source section for emitting a light beam having a second wavelength;

an eye-front-part illumination section for illuminating a portion close to the retina of the eye under measurement at a predetermined pattern with a light beam emitted from the second light-source section;

an eye-front-part observation section for receiving a reflected light beam which is reflected and returned from the portion close to the retina of the eye under measurement;

an eye-front-part-image light-receiving section for receiving a light beam received by the eye-front-part observation section;

a compensation-amount calculation section for obtaining an optical characteristic of the eye under measurement based on the output of the eye-front-part-image light-receiving section, and for obtaining and outputting the amount of compensation required to cancel aberration based on the optical characteristic;

a compensation optical section for applying aberration compensation based on the amount of compensation output from the compensation-amount calculation section to the reflected light beam from the retina of the eye under measurement, or to both an illumination light beam coming from the first illumination optical system and the reflected light beam from the retina of the eye under measurement; and a measurement calculation section for obtaining an optical characteristic of the eye under measurement according to an optical characteristic based on the output of the first light-receiving section, obtained after the compensation of the compensation optical section, and an optical characteristic compensated by the compensation optical section.

According to fifth solving means of this invention, there is provided an eye-characteristics measurement apparatus comprising:

a first light-source section for emitting a light beam having a first wavelength;

a first illumination optical system for illuminating a minute area on the retina of an eye under measurement, with a light beam emitted from the first light-source section;

a first light-receiving optical system for receiving a part of a reflected light beam which is reflected and returned from the retina of the eye under measurement, through a first conversion member for converting to at least substantially 17 beams;

a first light-receiving section for receiving a light beam received by the first light-receiving optical system;

a compensation-amount calculation section for obtaining an optical characteristic of the eye under measurement based on the output of the first light-receiving section, and for obtaining and outputting the amount of compensation required to cancel aberration based on the optical characteristic;

a compensation optical section for applying aberration compensation based on the amount of compensation output from the compensation-amount calculation section to the reflected light beam from the retina of the eye under measurement, or to both an illumination light beam coming from the first illumination optical system and the reflected light beam from the retina of the eye under measurement;

a third light-source section for emitting a light beam to illuminate the compensation optical section;

a third light-receiving optical system for receiving a light beam emitted from the third light-source section, through the compensation optical section and a third conversion member for converting to at least substantially 17 beams;

a third light-receiving section for receiving a light beam received by the third light-receiving optical system; and a measurement calculation section for measuring an optical characteristic based on the output of the first light-receiving section, obtained after the compensation of the compensation optical section, and an optical characteristic compensated by the compensation optical section based on the output of the third light-receiving section, and for obtaining an optical characteristic of the eye under measurement according to the measured optical characteristics.

According to sixth solving means of this invention, there is provided an eye-characteristics measurement apparatus comprising:

a first light-source section for emitting a light beam having a first wavelength;

a first illumination optical system for illuminating a minute area on the retina of an eye under measurement, with a light beam emitted from the first light-source section;

a third light-source section for emitting a light beam used for measuring aberration compensated for;

a first light-receiving optical system for receiving a part of a reflected light beam which is reflected and returned from the retina of the eye under measurement and a light beam emitted from the third light-receiving section, through a first conversion member for converting to at least substantially 17 beams;

a first light-receiving section for receiving a light beam received by the first light-receiving optical system;

a compensation-amount calculation section for obtaining an optical characteristic of the eye under measurement based on the output of the first light-receiving section, and for obtaining and outputting the amount of compensation required to cancel aberration based on the optical characteristic;

a compensation optical section for applying aberration compensation based on the amount of compensation output from the compensation-amount calculation section to the reflected light beam from the retina of the eye under measurement and a light beam coming from the third light-source section, or to an illumination light beam coming from the first illumination optical system, the reflected light beam from the retina of the eye under measurement, and the light beam coming from the third light-source section; and a measurement calculation section for measuring an optical characteristic compensated by the compensation optical section based on the output of the first light-receiving section caused by the light beam emitted from the third light-source section, for measuring an optical characteristic obtained after the compensation of the compensation optical section based on the output of the first light-receiving section caused by the light beam emitted from the first light-source section, and for obtaining an optical characteristic of the eye under measurement according to the measured optical characteristics.

BRIEF DESCRIPTION OF THE DRAWINGS

FIG. 24 is a view showing the structure of an optical system according to a first modification of the sixth embodiment.

FIG. 33 shows a Zernike polynomial (1).

FIG. 34 shows a Zernike polynomial (2).

BEST MODE FOR CARRYING OUT THE INVENTION

1. FIRST EMBODIMENT (Optical-System Structure)

Figure 1:
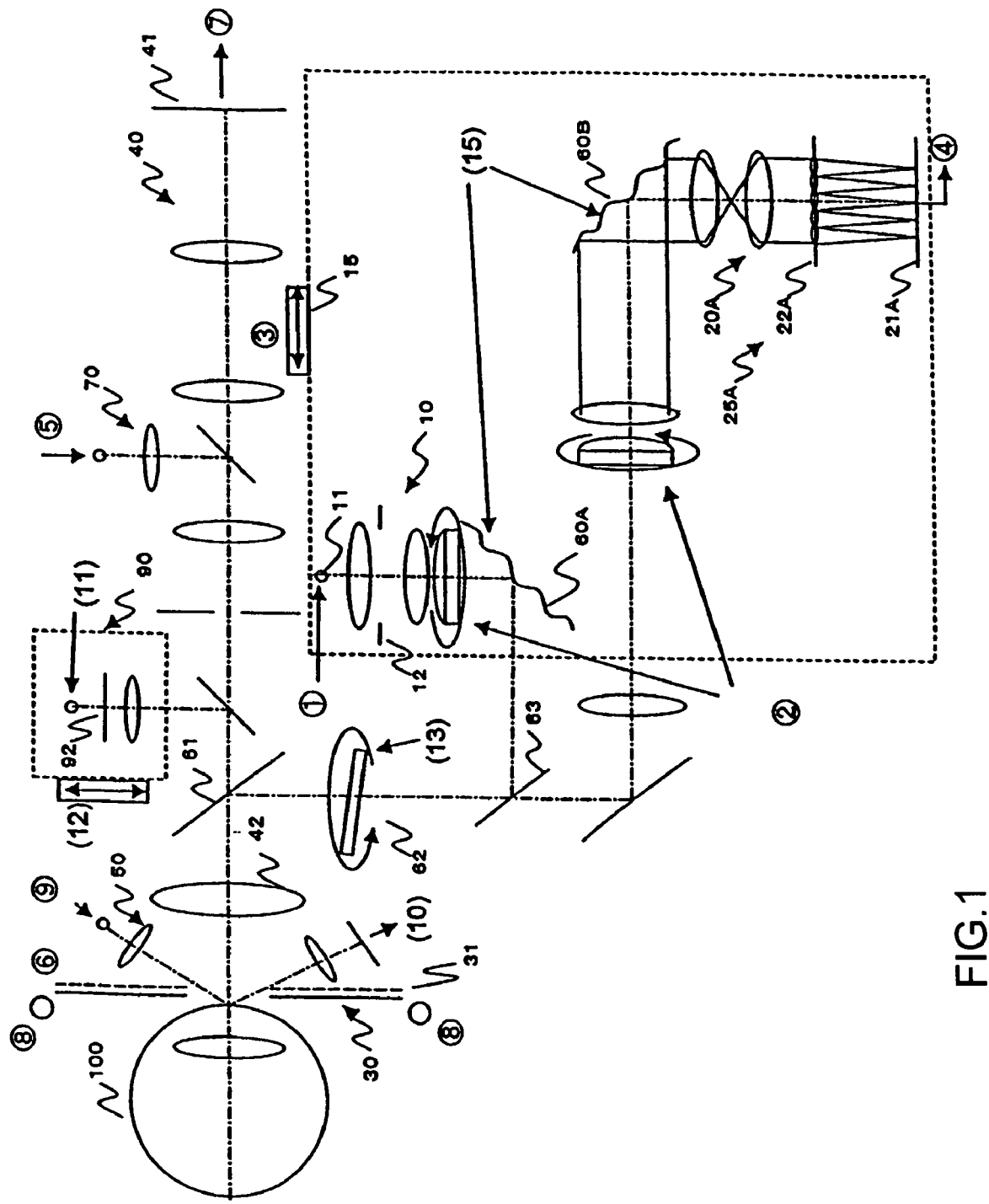
FIG. 1 is a view showing the structure of an optical system according to a first embodiment.

FIG. 1 is a view showing the structure of an optical system according to a first embodiment.

An eye-characteristics measurement apparatus includes a first illumination optical system 10, a first light-source section 11, a first measurement section 25A, an eye-front-part illumination section 30, an eye-front-part observation section 40, a first adjustment optical section 50, a first compensation optical section 60A, a second compensation optical section 60B, a second adjustment optical section 70, and an eyesight-target optical section 90. The first measurement section 25A has a first light-receiving optical system 20A and a first light-receiving section 21A. In an eye 100 under measurement, a retina (eyeground) and a cornea (eye-front part) are shown in the figure.

Each section will be described below in detail.

The first illumination optical system 10 illuminates a minute area on the eyeground of the eye 100 under measurement with a light beam emitted from the first light-source section 11. The first illumination optical system 10 includes, for example, a condenser lens, a pair of positive and negative cylinder lenses (so-called variable cross cylinders), and a relay lens. The variable cross cylinders may be omitted.

The first light-source section 11 emits a light beam having a first wavelength. It is desired that the first light-source section 11 have high spatial coherence and not-high temporal coherence. As an example, an SLD (super luminescence diode) is employed as the first light-source section 11, and provides a point light source having high luminance. The first light-source section 11 is not limited to an SLD. Even a laser, having both high spatial coherence and high temporal coherence, can be used by inserting a rotating diffusion plate to appropriately reduce the temporal coherence. Further, even an LED, having both low spatial coherence and low temporal coherence, can be used by inserting a pin hole or the like at the position of the light source in the optical path if the amount of light emitted from the LED is sufficient. The wavelength of the first light-source section 11 for illumination can be set, for example, to a wavelength (780 nm, for instance) in the infrared region.

The first light-receiving optical system 20A, for example, receives a light beam reflected by the retina of the eye under measurement 100 and leads it to the first light-receiving section 21A. The first light-receiving optical system 20A includes, for example, a first conversion member 22A (such as a Hartmann plate), an afocal lens, variable cross cylinders, and a relay lens. The variable cross cylinders may be omitted. The first conversion member 22A is a wavefront conversion member having a lens section for converting the reflected light beam to a plurality of at least 17 light beams. The first conversion member 22A may be a wavefront conversion member having a lens section with a long focal length or a high sensitivity. The first conversion member 22A is preferably a wavefront conversion member having a lens section with a long focal length and a high sensitivity. The first conversion member 22A can be a plurality of micro Fresnel lenses disposed on a plane perpendicular to the optical axis. The light reflected from the eyeground is collected on the first light-receiving section 21A through the first conversion member 22A. The first light-receiving section 21A receives the light coming from the first light-receiving optical system 20A and passing through the first conversion member 22A to generate a first signal. The front focus of the afocal lens 42 is almost at the pupil of the eye 100 under measurement.

A moving section 15 collectively moves a block enclosed by a dotted line in FIG. 1, which includes the first illumination optical system 10 and the first light-receiving optical system 20A. For example, when it is assumed that a light beam emitted from the first light-source section 11 is reflected at a point where the light beam is collected, while a relationship is maintained where the first light-receiving section 21A has the maximum signal peak caused by the reflection light, the moving section 15 can move the block in a direction in which the first light-receiving section 21A has a higher signal peak and stop the block at a position where the maximum strength is obtained. It is also possible that the first illumination optical system 10 and the first light-receiving optical system 20A are separately moved, and for example, when it is assumed that a light beam emitted from the first light-source section 11 is reflected at a point where the light beam is collected, while a relationship is maintained where the first light-receiving section 21A has the maximum signal peak caused by the reflection light, movement is performed in a direction in which the first light-receiving section 21A has a higher signal peak and movement is stopped at a position where the maximum strength is obtained.

The diameter of light emitted from the first light-source section 11 and incident on the eye 100 under measurement is adjusted by a diaphragm 12. In the present embodiment, adjustment is made for so-called double-path measurement where the eye 100 under measurement is illuminated with a wide (large-diameter) beam. In double-path measurement, the amount of light can be made large. This is an advantage, but at the same time, the effect of aberration tends to apply when incident light forms a secondary light source at the eyeground, and light blurs to spread the secondary light source. In the present embodiment, a light beam which cancels aberration is incident on the eye 100 under measurement to remove the effect of aberration to implement double-path measurement. The diaphragm 12 may be configured so as to allow so-called single-path aberration measurement, where the diameter of the diaphragm 12 is smaller than the effective area of the Hartmann plate and eye aberration affects only the light-receiving side. After incident light emitted from the first light-source section 11 advances the same optical path as measurement light diffuse-reflected from the eyeground, the incident light advances in the same way as the measurement light diffuse-reflected from the eyeground at a zone close to the axis.

The eye-front-part illumination section 30 includes a second light-source section 31 emitting a light beam having a second wavelength. The light beam emitted from the second light-source section 31 illuminates an eye front part at a predetermined pattern by using, for example, a Placido's ring or a kerato-ring. When a kerato-ring is used, only a pattern near the curvature center of the cornea is obtained due to the kerato-image. The second wavelength of the light beam emitted from the second light-source section 31 can, for example, differ from the first wavelength (780 nm in this case) and be a long wavelength (such as 940 nm).

The eye-front-part observation section 40 includes an eye-front-part-image light-receiving section 41 formed, for example, of a relay lens, a telecentric diaphragm, and a CCD, and observes, for example, a light beam obtained when the pattern of the eye-front-part illumination section 30, such as a Placido's ring or a kerato-ring, is reflected by the eye front part of the eye 100 under measurement. The telecentric diaphragm prevents the eye-front-part image from blurring.

The first adjustment optical section 50 mainly performs, for example, working-distance adjustment, and includes a light-source section, a condenser lens, and a light-receiving section. The working-distance adjustment is performed by illuminating the eye 100 under measurement with parallel beams close to the optical axis and emitted from the light-source section and by receiving light reflected from the eye 100 under measurement by the light-receiving section through the condenser lens. When the eye 100 under measurement is located at an appropriate working distance, a spot image of the light-source section is formed on the light-receiving section in the optical axis. If the eye 100 under measurement is shifted ahead or behind from an appropriate working distance, a spot image of the light-source section is formed upper or lower with respect to the optical axis on the light-receiving section. Since the light-receiving section needs to detect a change of the beam position on a plane which includes the light-source section, the optical axis, and the light-receiving section, a device disposed on the plane, such as a one-dimensional CCD or a position sensing device (PSD), can be used.

The first compensation optical section 60A and the second compensation optical section 60B are adaptive optical systems (adaptive optics) for compensating for aberration included in measurement light, by deformation. The first compensation optical section 60A is disposed in the first illumination optical system 10, and, for example, reflects a light beam emitted from the first light-source section 11 and sends a light beam for compensating for aberration to the eye 100 under measurement. The second compensation optical system 60B is disposed in the first light-receiving optical system 20A, and, for example, compensates for aberration included in a reflection light beam reflected and returned from the eye 100 under measurement. The first and second compensation optical sections 60A and 60B can, for example, be deformable mirrors or liquid-crystal spatial optical modulators. In addition, appropriate optical systems capable of compensating for aberration included in measurement light can also be used. A deformable mirror changes the direction of reflection of a light beam by deforming the mirror by an actuator provided inside the mirror. There are also a deformation method using a capacitor and a deformation method using a piezoelectric device. In addition, other appropriate methods can be used. Liquid-crystal spatial optical modulators modulate the phase by using the alignment characteristic of liquid crystal, and reflect a light beam in the same way as mirrors. A polarizer is required in the optical path. In the present embodiment, a beam splitter 63 plays that role. The beam splitter 63 is formed of a mirror (such as a polarization beam splitter) which reflects a light beam emitted from the first light-source section 11 and transmits a reflection light beam reflected and returned from the retina of the eye 100 under measurement. The first compensation optical section 60A and the second compensation optical section 60B may be transmission-type optical systems in stead of reflection optical systems. The first compensation optical section 60A and the second compensation optical section 60B are not limited to those described above, but it is preferred that parallel beams be incident thereon. If the eye 100 under measurement had no aberration, for example, a light beam reflected from the retina of the eye 100 under measurement is incident on the second compensation optical section 60B as a parallel beam. For example, a light beam emitted from the first light-source section 11 is always incident on the first compensation optical section 60A as parallel light.

A beam splitter 61 is formed, for example, of a dichroic mirror which reflects a light beam having the first wavelength and transmits a light beam having the second wavelength. A rotary prism 62 for making uniform light having reflection unevenness coming from the eyeground is also disposed.

The second adjustment optical section 70, for example, performs alignment adjustment in the X and Y directions, and includes an alignment light-source section, a lens, and a beam splitter in order to make a bright point at the vertex of the cornea.

The eyesight-target optical section 90 includes, for example, a landscape chart for the eye 100 under measurement and an optical path for projecting an eyesight-target for fixation and clouding and fogging, and is provided with a light-source section (such as a lamp), a fixation target 92, and a relay lens. The section 90 can project the fixation target 92 on the eyeground with a light beam emitted from the light-source section, and makes the eye 100 under measurement observe its image.

(Conjugate Relation)

The eyeground of the eye 100 under measurement, the fixation target 92 in the eyesight-target optical section 90, the first light-source section 11, and the first light-receiving section 21A are conjugate. The pupil (iris) of the eye of the eye 100 under measurement, the rotary prism 62, the first conversion member (Hartmann plate) 22A, the diaphragm 12 at the measurement-light incidence side of the first illumination optical system 10, the first compensation optical section 60A, and the second compensation optical section 60B are conjugate.

(Electrical-System Configuration)

Figure 2:
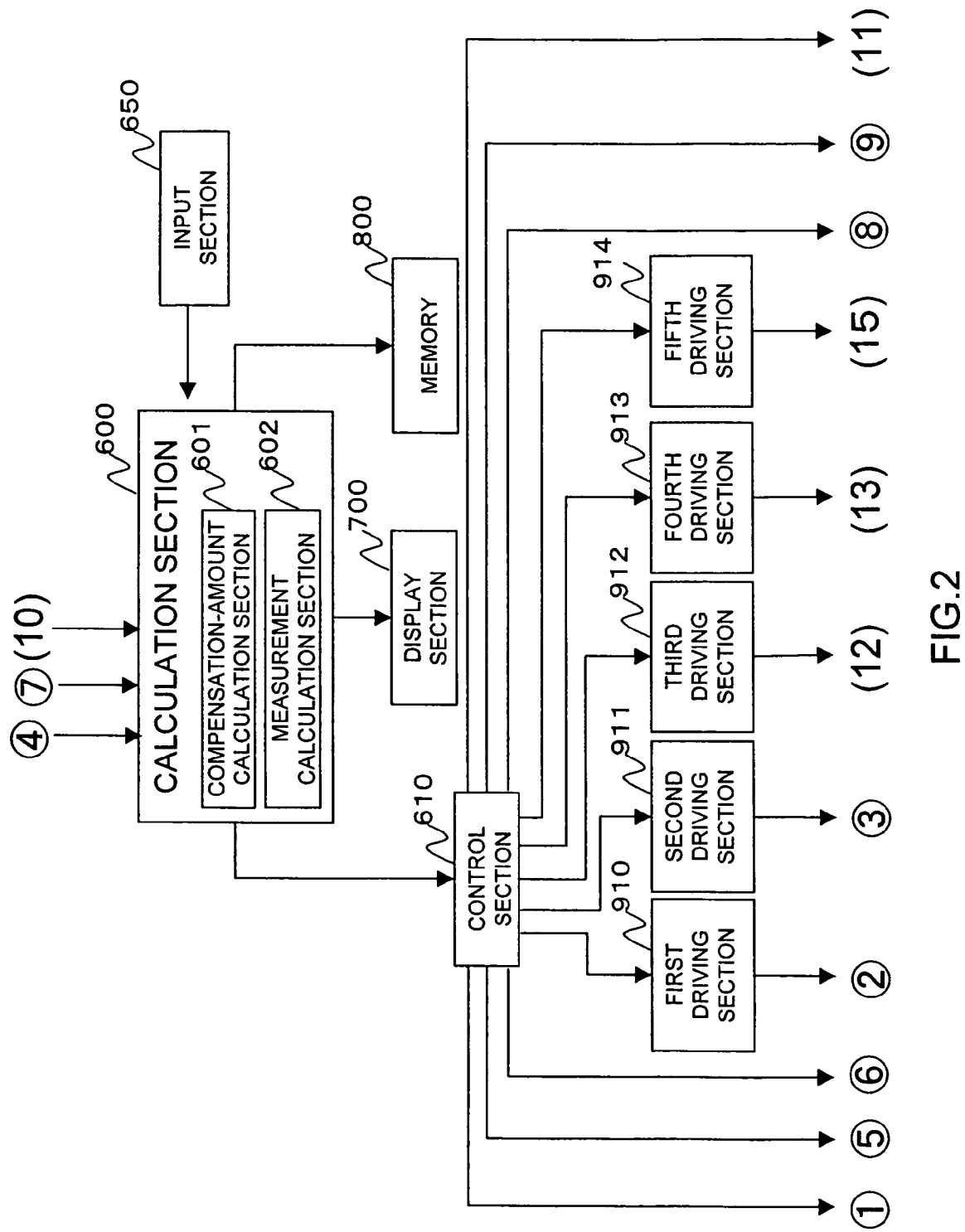
FIG. 2 is a view showing the structure of an electrical system according to the first embodiment.

FIG. 2 is a structural view of an electrical system according to the first embodiment.

In the structure of the electrical system of the eye-characteristics measurement apparatus, a calculation section 600, a control section 610, an input section 650, a display section 700, a memory 800, a first driving section 910, a second driving section 911, a third driving section 912, a fourth driving section 913, and a fifth driving section 914 are provided. The calculation section 600 includes, for example, a compensation-amount calculation section 601 and a measurement calculation section 602 for measuring various eye characteristics. The input section 650 includes a pointing device for pointing a button, an icon, a position, an area, or others displayed on the display section 700, if necessary, a keyboard for inputting various types of data, and others.

The calculation section 600 receives, for example, a first signal ④ from the first light-receiving section 21A, a signal ⑦ from the eye-front-part observation section 40, and a signal (10) from the first adjustment optical section 50.

The measurement calculation section 602 receives the first signal ④ from the first light-receiving section 21A and the signal ⑦ from the eye-front-part observation section 40 and obtains an optical characteristic of the eye 100 under measurement. The compensation-amount calculation section 601 obtains the amounts of compensation used in the first and second compensation optical sections 60A and 60B according, for example, to an optical characteristic obtained from the output of the first measurement section 25A. The compensation-amount calculation section 601 may obtain the amounts of compensation according to an optical characteristic obtained from the output of other measurement sections or optical-characteristic data input from the input section 650 or the memory 800. The calculation section 600 appropriately outputs signals corresponding to these calculation results, or other signals and data to the control section 610, which controls an electrical driving system, to the display section 700, and to the memory 800.

The control section 600 controls turning on and off of the first light-source section 11 and controls the first driving section 910 to the fifth driving section 914 according to control signals sent from the calculation section 600. For example, the control section 610 outputs a signal ① to the first light-source section 11, a signal ⑤ to the second adjustment optical section 70, a signal ⑥ to the eye-front-part illumination section 30, signals ⑧ and ⑨ to the first adjustment optical section 50, a signal (11) to the eyesight-target optical section 90, and further signals to the first driving section 910 to the fifth driving section 914, according to signals corresponding to the calculation results of the calculation section 600.

The first driving section 910 outputs a signal ② based on the signal ④ sent from the first light-receiving section 21A, which was input to the calculation section 600, to drive appropriate lens-moving means to rotate the variable cross cylinders of the first illumination optical system 10 and the variable cross cylinders of the first light-receiving optical system 20A to compensate for an astigmatic component of the eye under measurement. This compensation may be omitted.

The second driving section 911, for example, moves the first illumination optical system 10 and the first light-receiving optical system 20A along the optical axis, based on the signal ④ sent from the first light-receiving section 21A, which was input to the calculation section 600, outputs a signal ③ to the moving section 15, and drives lens moving means of the moving section 15. By moving the first light-receiving optical system 20A and others along the optical axis, the spherical-power component of lower-order aberration can be compensated for.

The third driving section 912, for example, moves the eyesight-target optical section 90, outputs a signal (12) to appropriate moving means (not shown), and drives the moving means. The fourth driving section 913 rotates the rotary prism 62, outputs a signal (13) to appropriate lens moving means (not shown), and drives the lens moving means. The fifth driving section 914 drives the first and second compensation optical sections 60A and 60B, outputs a signal (15) based on the amount of compensation obtained by the compensation-amount calculation section 602, to deformation means of the first and second compensation optical sections 60A and 60B, and drives the deformation means.

(Flowchart)

Figure 3:
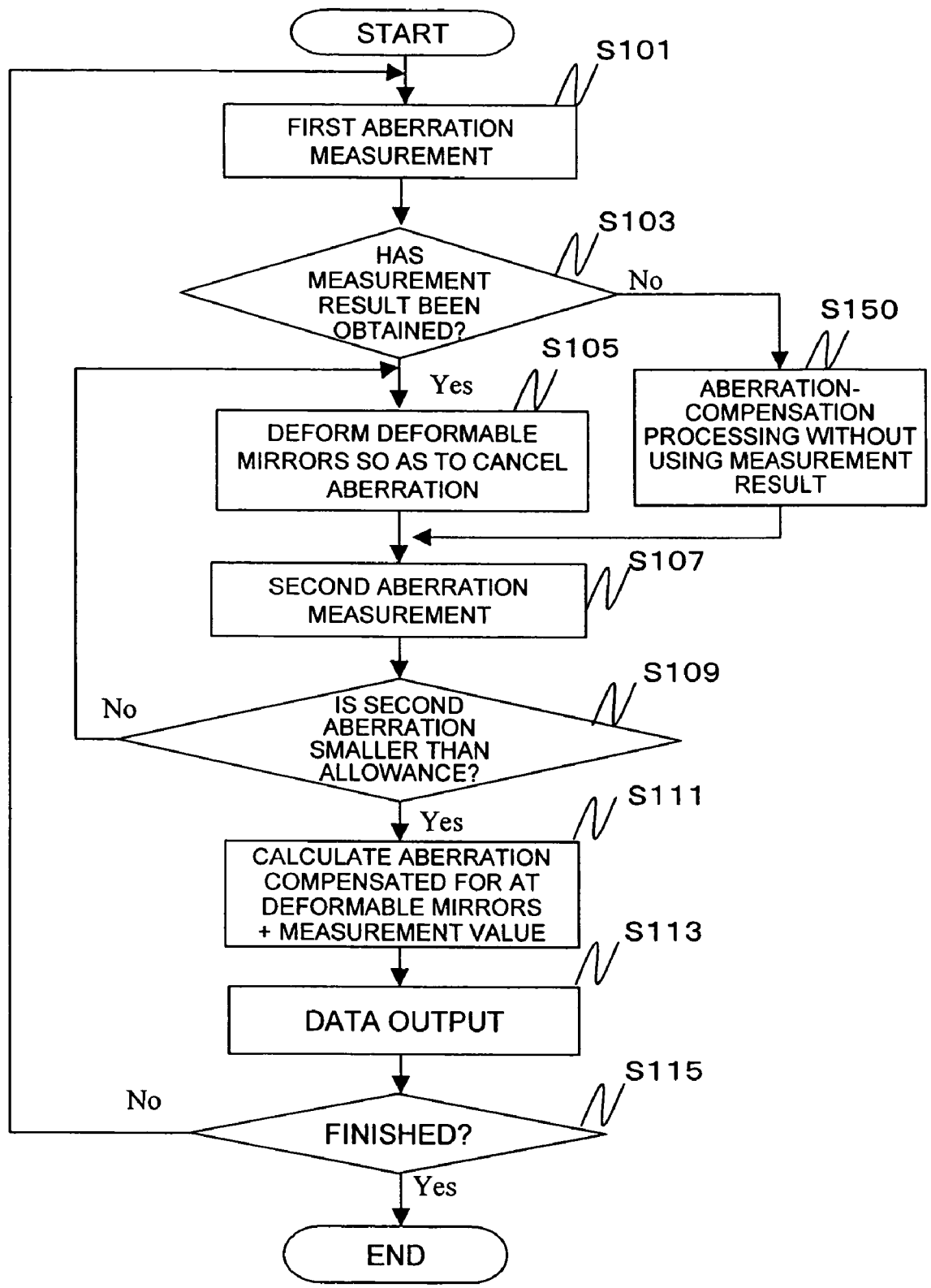
FIG. 3 is a flowchart of aberration measurement which uses the optical system according to the first embodiment.
Figure 4:
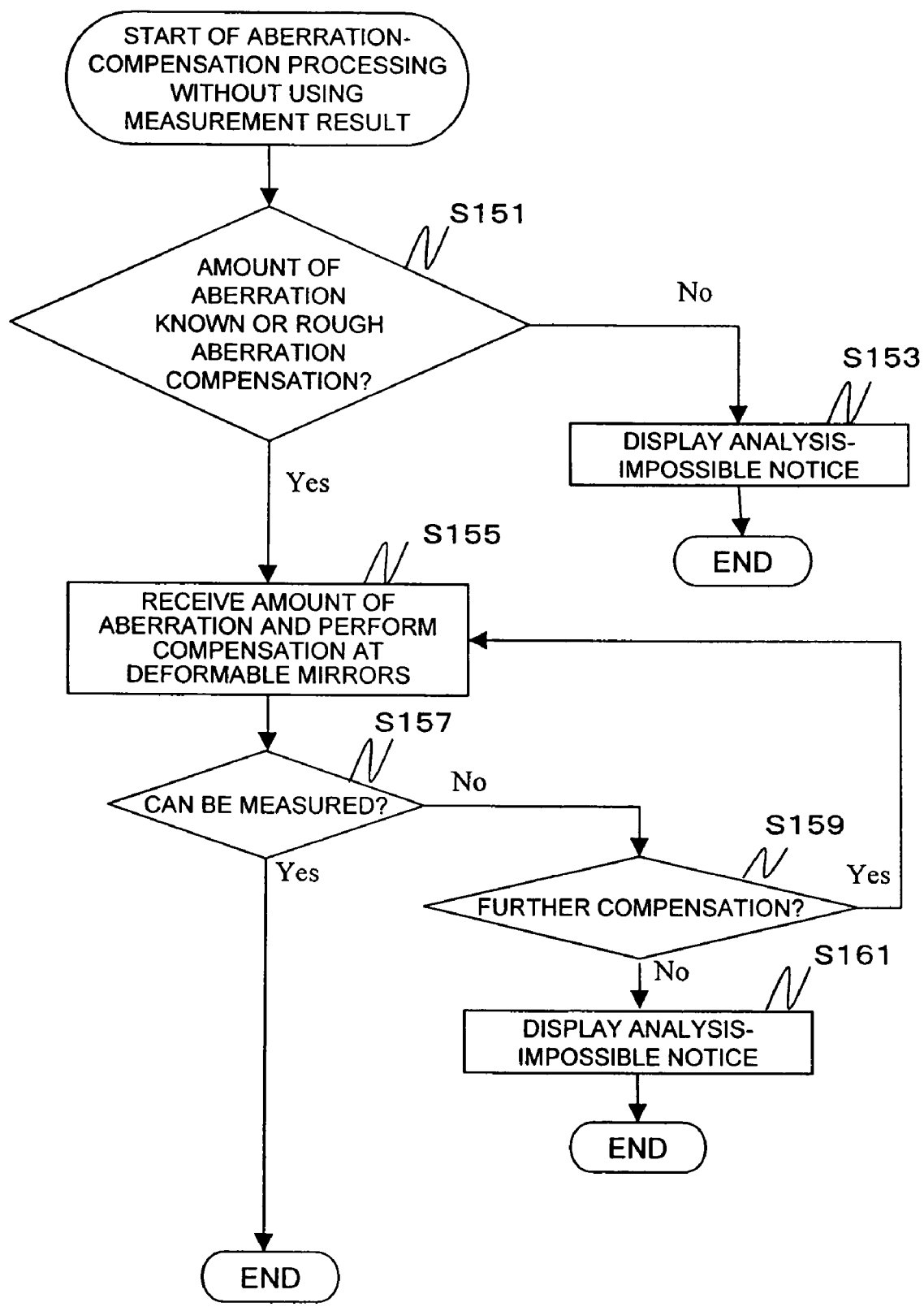
FIG. 4 is a flowchart of aberration-compensation processing other than a first aberration measurement.

FIG. 3 and FIG. 4 are flowcharts of aberration measurement which uses the optical system according to the first embodiment. The calculation section 600 determines the amount of compensation based on the output of the first light-receiving section 21A, the output being obtained in a first aberration measurement, deforms the first and second compensation optical sections 60A and 60B to compensate for aberration, and obtains an optical characteristic of the eye 100 under measurement from aberration obtained after the compensation and the aberration compensated for. If aberration is not obtained from the Hartmann image from the first light-receiving section 21A, compensation is, for example, performed according to an optical characteristic at a portion close to the cornea based on the eye-front-part-image light-receiving section 41 to implement aberration measurement.

First, the calculation section 600 obtains the aberration of the eye 100 under measurement according to the first signal sent from the first light-receiving section 21A in a first aberration measurement (S101). The calculation section 600 receives the first signal of the Hartmann image from the first light-receiving section 21A of the first measurement section 25A. Then, the calculation section 600 obtains the point-image movement distances Δx and Δy of the Hartmann image from the received first signal, calculates the Zernike coefficients according to the point-image movement distances, and obtains the aberration of the eye 100 under measurement. Further, the calculation section 600 may obtain the shape, aberration, and others of the cornea according to the signal from the eye-front-part-image light-receiving section 41 of the eye-front-part observation section 40. The calculation section 600 stores there calculation results in the memory 800.

An aberration calculation will be described below. The calculation section 600 obtains the movement distances Δx and Δy of each point image from the image of the first measurement section 25A. The movement distances and the aberration W are associated with each other by the following partial differential equations.

$$\frac{\partial W(X,Y)}{\partial X} = \frac{\Delta x}{f}, \quad (1)$$

$$\frac{\partial W(X,Y)}{\partial Y} = \frac{\Delta y}{f}$$

(f: Distance Between the Hartmann Plate and the CCD in the First Measurement Section 25A)

When the wavefront W is expressed by the expansion of the Zernike polynomial $Z_i^{2j-i}$, $$W(X,Y) = \sum_{i=0}^{n} \sum_{j=0}^{i} c_i^{2j-i} Z_i^{2j-i}(X,Y) \quad (2)$$

The value of the Zernike coefficients $C_i^{2j-i}$ can be obtained from the foregoing two expressions and measurement values related to Δx and Δy (therefore, including X and Y) obtained by the measurement. To obtain the cornea aberration, the tilt angle and height of the cornea are calculated according to the signal sent from the eye-front-part-image light-receiving section 41 of the eye-front-part observation section 40, and the cornea is treated in the same way as an optical lens to calculate its optical characteristics. FIG. 33 and FIG. 34 are views (1) and (2) showing the Zernike polynomial.

Then, the calculation section 600 determines whether the measurement result has been obtained (S103). The calculation section 600 can determine it according to one or a plurality of appropriate conditions determined in advance, such as whether the number of centers of gravity of the point images of the Hartmann image obtained in the first aberration measurement is less than a predetermined value (for example, less than one third the predetermined value), whether each point image has a large blur (for example, has a blur 20 times or more that obtained when there is no aberration), or whether the number of points which cannot be separated from an adjacent spot image and therefore cannot be detected is not less than a predetermined value. When the calculation section 600 has obtained the measurement result (S103), the processing proceeds to the process of step S105. When the calculation section 600 has not obtained the measurement result (S103), the processing proceeds to the process of step S150.

In step S105, the calculation section 600 obtains the amount M of compensation to cancel the obtained aberration, at the first and second compensation optical sections 60A and 60B, outputs a signal (15) corresponding to the amount M of compensation through the control section 610 and the fifth driving section 914, and deforms the first and second compensation optical sections 60A and 60B, such as a deformable mirror (S105). The first and second compensation optical sections 60A and 60B are deformed by appropriate deformation means according to the signal (15). The first and second compensation optical sections 60A and 60B may be liquid-crystal spatial optical modulators, instead of deformable mirrors. When the first compensation optical section 60A compensates for aberration included in incident light, an illumination state is obtained where a point light source is made on the eyeground even if the eye 100 under measurement has much aberration. Especially in double-path measurement, which is susceptible to the effect of aberration, the effect of aberration can be removed. When the second compensation optical section 60B compensates for aberration included in a reflection light beam returned from the eye under measurement, the light beam obtained after compensation can be precisely measured. The calculation of the amount M of compensation to cancel aberration will be described below.

Figure 5:
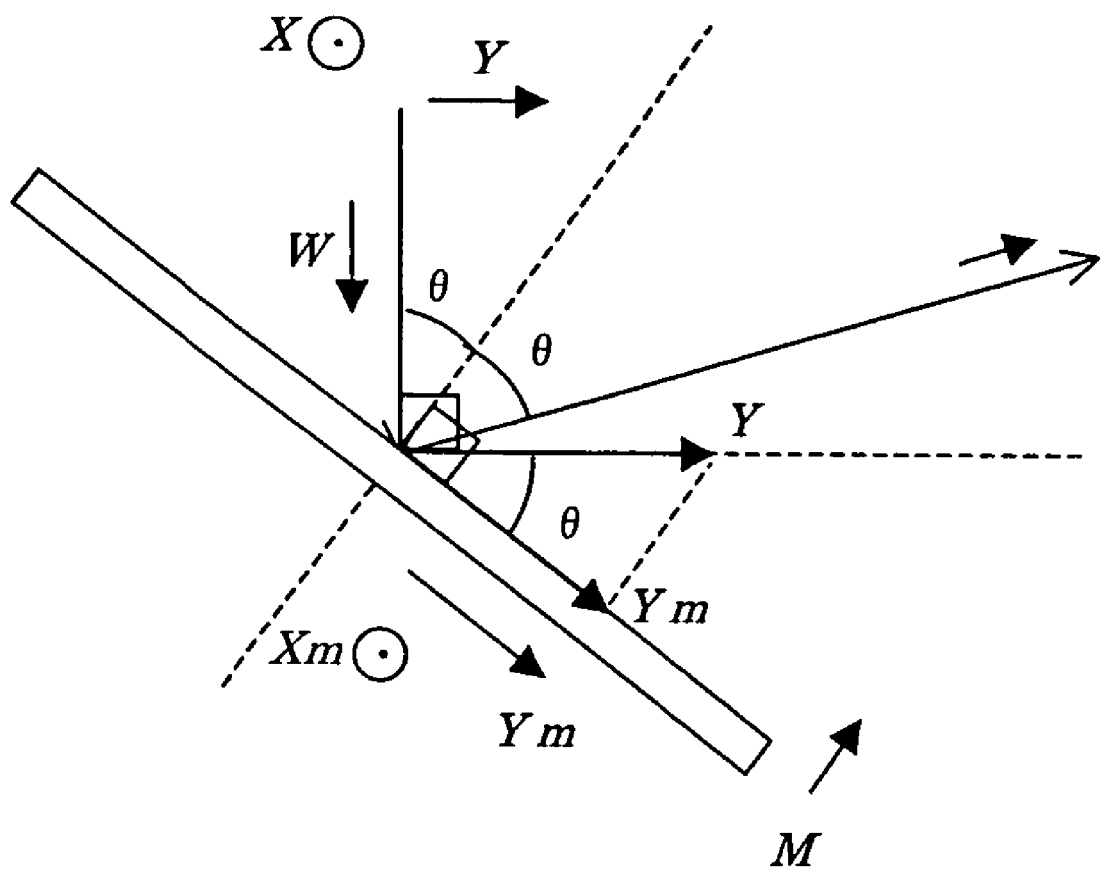
FIG. 5 is a view showing the relationship between coordinates.

FIG. 5 is a view showing the relationships between coordinates $(X_m, Y_m)$ on a deformable mirror and coordinates (X, Y) on the optical system. When an analyzed aberration expression is shown as described below with aberration to be compensated for being called Wc, $$Wc = \sum_{n=1}^{N} \sum_{m=-n,-n+2,...}^{n} c_n^m Z_n^m(X,Y) \quad (3)$$

the relationships between coordinates $(X_m, Y_m)$ on the deformable mirror and coordinates (X, Y) on the optical system are indicated below with the angle of incidence θ to the deformable mirror being taken into account.

$$\begin{cases} X_m = X \\ Y_m = Y/\cos\theta \end{cases} \quad (4)$$

$$\begin{cases} X = X_m \\ Y = Y_m \cos\theta \end{cases}$$

The facts that the amount M of compensation for the deformable mirror affects twice because of reflection, and that the pupil of the eye and the deformable mirror have their magnifications are taken into account. When the magnification of the deformable mirror with respect to the pupil is "k", the amount M of compensation is expressed as below.

$$M = \frac{1}{k}\sum_{n=1}^{N}\sum_{m=-n,-n+2,...}^{n}\left(-\frac{1}{2}c_n^m\right)Z_n^m(X_m, Y_m\cos\theta) \quad (5)$$

The amount M of compensation obtained here can have higher order aberrations. The first and second compensation optical sections 60A and 60B are deformed according to the amount M of compensation output from the calculation section 600. The magnification "k" and the angle of incidence θ obtained at the no-compensation state are specified in advance, and stored in the memory 800 beforehand.

The spherical-power component, which is lower-order aberration, can be compensated for by moving the first light-receiving section 25A by the moving section 15. The astigmatic component, which is lower-order aberration, can be compensated for by rotating the variable cross cylinders. To further deform the deformed deformable mirror, it is necessary to obtain the amount M of compensation with respect to aberration measured after the compensation in the same way as in the above-described analysis and to additionally apply the amount M of compensation to the deformable mirror obtained after the compensation. The first and second compensation optical sections 60A and 60B may direct the light incident on the Hartmann plate slightly toward a divergence direction or make it slightly tilted, instead of canceling the aberration completely. With this, for example, high-sensitivity measurement can be made with the use of the first light-receiving optical system 20A having a first conversion member 22A having a long focal length or a high sensitivity, or a long focal length and a high sensitivity.

When the third-order of higher aberration is lower than a predetermined value among the obtained aberration, for example, the calculation section 600 can move the first light-receiving optical system 20A and/or rotate the variable cross cylinders according to the obtained aberration. In this case, the calculation section 600, for example, moves the second light-receiving optical system 20A according to the spherical power component $c_2^0$ among the obtained aberration, and/or rotates the variable cross cylinders according to the astigmatic components $c_2^{-2}$ and $c_2^2$. Further, the calculation section 600 obtains the amount M of compensation based on aberration other than $c_2^0$ and/or $c_2^{-2}$, and $c_2^2$, and deforms the compensation optical section 60 based on the amount M of compensation. In this case, the amount M of compensation needs to be obtained by using the settings: $C_2^0=0$ and/or $C_2^{-2}=0$, and $C_2^2=0$. Aberration may be measured again after the spherical-power component and/or the astigmatic components are compensated for to calculate the amount M of compensation based on the aberration.

In step S150, the calculation section 600 performs aberration-compensation processing (S150) without using the measurement result obtained in step S101, and the processing proceeds to step S107.

FIG. 4 is a flowchart of aberration-compensation processing without using the first aberration measurement. The processing shown in FIG. 4 will be described below.

First, the calculation section 600 determines whether a rough amount of aberration is understood, or aberration compensation is to be performed roughly (S151). For example, it is determined whether to continue measurement by using cornea aberration, past aberration data, and others as references. As a determination method, the calculation section 600 may receive a signal which continues or terminates measurement from a dialog box automatically displayed or the input section 650 or others called from the menu. The calculation section 600 may search the memory 800 for cornea aberration data or past aberration data to determine whether to continue or terminate measurement according to whether data exists.

If the measurement is not continued, the calculation section 600 displays an analysis-impossible notice on the display section 700 (S153), and terminates the measurement. When the measurement is continued, the calculation section 600 receives the Zernike coefficients and aberration data such as cornea aberration data and past aberration data from the memory 800 in the apparatus or the input section 650, obtains the amount M of compensation for the first and second compensation optical sections 60A and 60B such as deformable mirrors, and deforms the deformable mirrors through the control section 610 and the fifth driving section 914 (S155). The calculation section 600 may receive a signal from the eye-front-part-image light-receiving section 41 of the eye-front-part observation section 40 to obtain the cornea aberration and to calculate the amount M of compensation according to the obtained aberration. The amount M of compensation is calculated in the same way as in step S105. The calculation section 600 outputs the signal (15) corresponding to the amount M of compensation through the control section 610 and the fifth driving section 914 to deform the first and second compensation optical sections 60A and 60B. In the present embodiment, if the optical characteristics of the eye under measurement cannot be measured from the Hartmann image, the measurement is made possible by compensating for aberration according to the cornea aberration and others as described above by the first and second compensation optical sections 60A and 60B.

Then, the calculation section 600 determines whether the optical characteristics can be measured after the compensation (S157). The calculation section 600 can determine it according to one or a plurality of appropriate conditions determined in advance, such as whether the number of centers of gravity of the Hartmann image received from the first light-receiving section 21A is less than a predetermined value (for example, less than one third the predetermined value), whether each point image has a large blur (for example, has a blur 20 times or more that obtained when there is no aberration), or whether the number of points which cannot be separated from an adjacent spot image and therefore cannot be detected is not less than a predetermined value. When the measurement is impossible, the calculation section 600 determines whether to apply further compensation (S159). For example, the calculation section 600 may receive a signal which continues or terminates the measurement from a dialog box automatically displayed or the input section 650 or others called from the menu. The calculation section 600 may search the memory 800 for another aberration data. When further compensation is to be applied, the calculation section 600 goes back to step S155. When further compensation is not applied, the calculation section 600 displays an analysis-impossible notice on the display section 700 (S161), and terminates the measurement.

When the measurement is possible (S157), the calculation section 600 terminals the aberration compensation processing.

Back to FIG. 3, the calculation section 600 obtains the first signal from the first light-receiving section 21A to obtain the aberration in a second aberration measurement (S107). The aberration to be obtained is the aberration after the compensation. For example, the first measurement section 25A can measure minute aberration at high precision. When the first and second compensation optical sections 60A and 60B have compensated for cornea aberration, the aberration to be obtained here is intraocular aberration.

Then, the calculation section 600 determines whether the aberration obtained in step S107 is equal to or smaller than an allowance specified in advance (S109). For example, the calculation section 600 may determine whether the RMS value of higher-order aberration is 0.1 or less. The RMS value (root-mean-square error) of aberration is calculated by the following expression with the use of the Zernike coefficients $C_i^{2j-i}$.

$$RMS_i^{2j-1} = \sqrt{\frac{\varepsilon_i^{2j-i}}{2(i+1)}} \, c_i^{2j-i} \quad (6)$$

$$(\varepsilon_i^{2j-i} = 2(2j=i), \varepsilon_i^{2j-i} = 1 \ (2j \neq i))$$

The calculation section 600 determines whether one or a plurality of the RMS values of these aberrations specified in advance is equal to or smaller than an allowance.

When the aberration is larger than the allowance (S109), the calculation section 600 goes back to step S105, and further deforms the first and second compensation optical sections 60A and 60B. When the aberration is smaller than the allowance (S109), the calculation section 600 adds the aberration canceled by the first and second compensation optical sections 60A and 60B to the aberration measured in step S107 to obtain the actual aberration W (including the Zernike coefficients $c_i^{2j-i}$) of the eye under measurement (S111). The calculation section 600 can obtain optical characteristics such as the spherical power S, the astigmatic power C, the astigmatic axis A, and higher-order spherical aberration by the use of a known method from the obtained Zernike coefficients $c_i^{2j-i}$ and the arrangement (for example, information of the movement position at the initial condition) of the optical system. The calculation section 600 can obtain the spherical power S, the astigmatic power C, and the astigmatic axis A from the second order terms of the Zernike coefficients by the following expressions.

$$SE = S_{move} - 4 \cdot \frac{c_2^0}{r^2} \quad (7)$$

$$S = SE - \frac{1}{2} \cdot C$$

$$C = -4 \cdot \frac{\sqrt{(c_2^{-2})^2 + (c_2^2)^2}}{r^2}$$

$$A = \tan^{-1}\left(\frac{c_2^{-2}}{c_2^2}\right) \cdot \frac{1}{2} \cdot \frac{180}{\pi} + 90$$

(where, SE: Equivalent Spherical Power, Smove: Spherical Power for Fixation Movement, r: Pupil Diameter)

The calculation section 600 displays the obtained aberration map, aberration coefficients, and the measurement results of the Hartmann image and the others on the display section 700, and stores them in the memory 800 (S113). The calculation section 600 may read the cornea shape data and others from the memory 800 and displays them further on the display section 700.

Further, the calculation section 600 determines whether to finish the measurement (S115). When the measurement is continued, the processing returns to step S101. When the measurement is finished, the calculation section 600 terminates the measurement. This measurement-termination determination may be made, for example, by a signal which continues or terminates the measurement, input to the calculation section 600 from a dialog box automatically displayed or from the input section 650 or others called from the menu.

Figure 6:
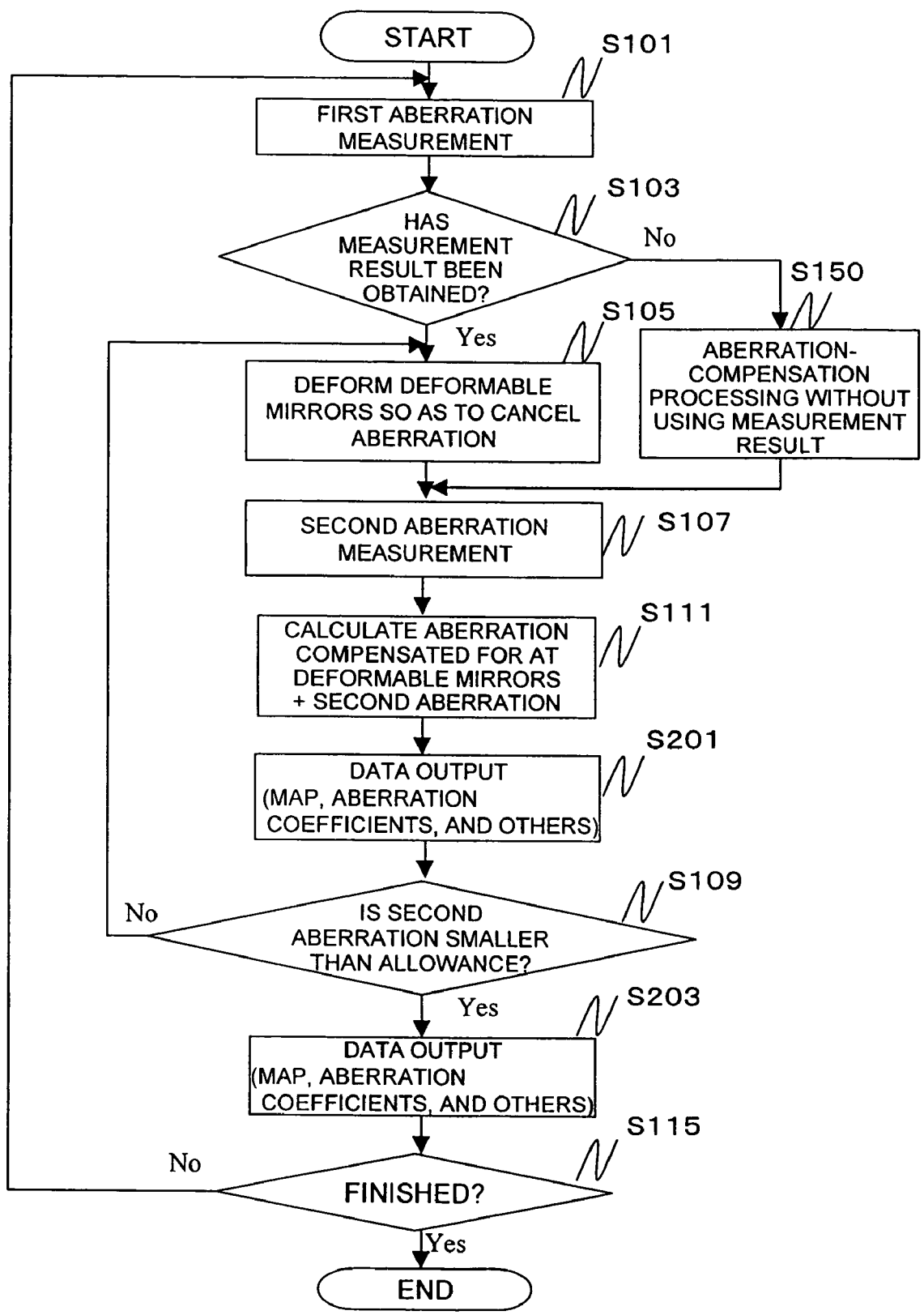
FIG. 6 is a modification of the flowchart of aberration measurement which uses the optical system according to the first embodiment.

FIG. 6 is a modification of the flowchart of the aberration measurement which uses the optical system according to the first embodiment. In the present modification, aberration calculation for the eye 100 under measurement and the output of the calculation result are performed each time aberration measurement is performed after compensation.

First, the calculation section 600 executes the processes of steps S101 to S107, and S111. Since the details of the processes are the same as those described above, a description thereof is omitted here.

The calculation section 600 displays the measurement results such as the obtained aberration map and aberration coefficients on the display section 700 and stores them in the memory 800 (S201). The measurement results need not necessarily to be displayed on the display section 700 every time. For example, when this display process to the display section 700 affects the measurement as in a case in which the display process takes long time, the measurement results may be displayed at an interval of a certain number of measurements.

The calculation section 600 determines whether the aberration obtained in step S111 is equal to or smaller than an allowance specified in advance (S109). The determination criterion can be the same as described above. When the aberration is larger than the allowance, the calculation section 600 goes back to step S105. When the aberration is smaller than the allowance, the calculation section 600 displays the measurement results such as the obtained aberration map, aberration coefficients, and Hartmann image on the display section 700 and stores them in the memory 800 (S203). When the measurement results have been displayed and stored in step S201, the process of step S203 may be omitted. The calculation section 600 may output to the display section 700 a display item which instructs an input of determining whether to further deform the first and second compensation optical sections 60A and 60B and receive a signal from the input section 650, instead of determining whether the aberration is equal to or smaller than the allowance. Then, the calculation section 600 executes the process of step S115. The details of the process are the same as described above.

2. SECOND EMBODIMENT (Optical-System Structure)

Figure 7:
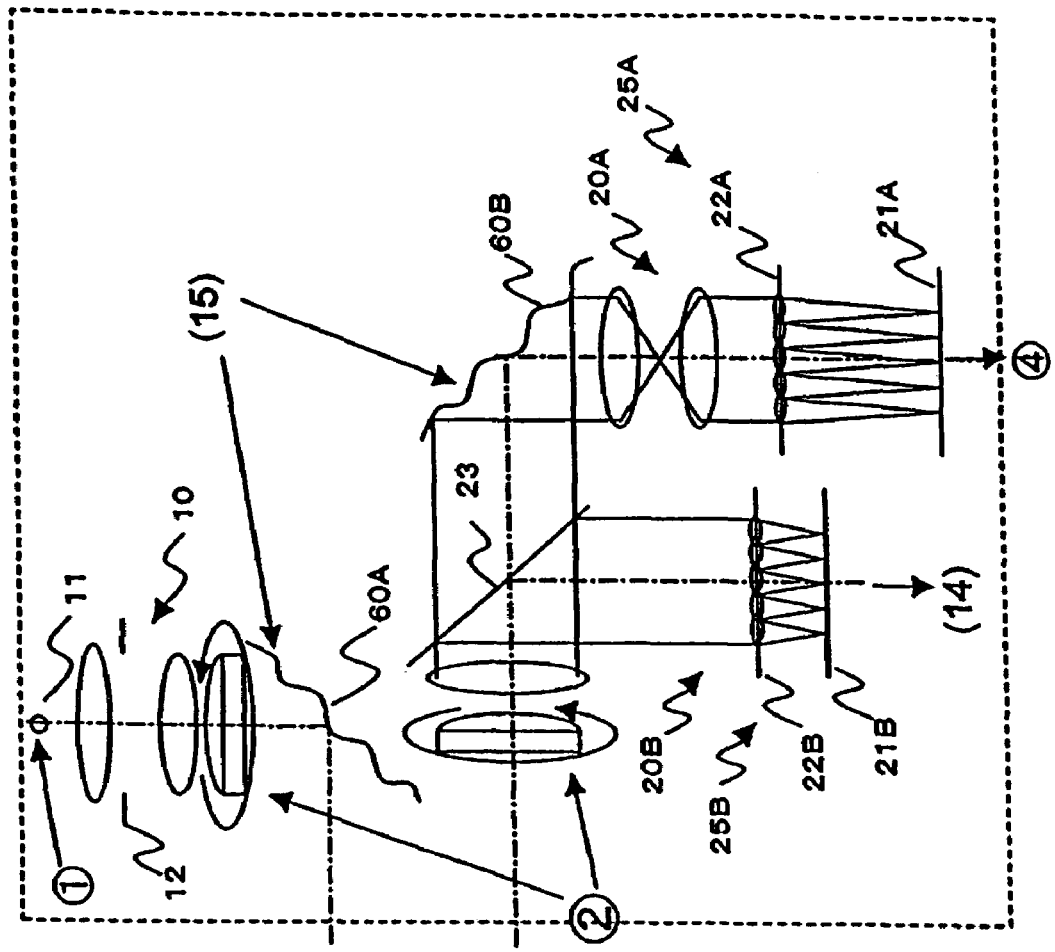
FIG. 7 is a view showing the structure of an optical system according to a second embodiment.

FIG. 7 is a view showing the structure of an optical system according to a second embodiment. FIG. 7 shows only a portion corresponding to that enclosed by the dotted line in FIG. 1, but the other portions are the same as those shown in FIG. 1. An eye-characteristics measurement apparatus shown in FIG. 7 further includes a second measurement section 25B having a short focal length, a low sensitivity, or a high density, and a beam splitter 23. A first conversion member 22A according to the present embodiment is a wavefront conversion member having a lens section with a long focal length or a high sensitivity. It is preferred that the second measurement section 25B be configured to have a short focal length, a low sensitivity, and a high density. The first conversion member 22A may be configured to have a long focal length and a high sensitivity.

The second measurement section 25B has a second light-receiving optical system 20B and a second light-receiving section 21B. The second light-receiving optical system 20B receives a light beam reflected and returned from the retina of the eye 100 under measurement and leads it to the second light-receiving section 21B, in the same way as the first light-receiving optical system 20A. The second light-receiving optical system 20B includes, for example, a second conversion member 22B (such as a Hartmann plate), and an afocal lens, variable cross cylinders, and a relay lens which are shared by the first light-receiving optical system 20A. The second conversion member 22B is a wavefront conversion member having a lens section having a short focal length, a low sensitivity, or a high density for converting the reflected light beam to a plurality of at least 17 light beams. It is more preferred that the second conversion member 22B be configured to have at least a short focal length and a low sensitivity.

The second conversion member 22B can be a plurality of micro Fresnel lenses disposed on a plane perpendicular to the optical axis. The light reflected from the eyeground is collected on the second light-receiving section 21B through the second conversion member 22B. The second light-receiving section 21B receives the light sent from the second light-receiving optical system 20B and passing through the second conversion member 22B to generate a second signal. A beam splitter 23 divides a light beam into one for the first measurement section 25A and the other for the second measurement section 25B. Alternately, instead of the beam splitter 23, a mirror can be used, which is moved and inserted into the optical path to switch between the first and second measurement sections 25A and 25B. The optical system according to the second embodiment, described above, is configured for double-path measurement. It can be changed for single-path measurement, if necessary.

In the present embodiment, "a short focal length, a low sensitivity, and a high density" means that the change of the beam converted by the second conversion member 22B over the area where measurement is possible is set smaller than the conversion pitch of the second conversion member 22B. As a result, it is easier to associate each spot obtained by the second light-receiving section 21B with a grid point, and signal processing can be made more easily and more quickly. In measurement with a long focal length and/or a high sensitivity, a shift in spot position is large, and a spot may be disposed outside the range of the Hartmann grid. Therefore, if a spot position shifts very large due to much aberration or other reasons, it is difficult in some cases to associate each spot with a grid point, making signal processing long.

(Conjugate Relation)

The second light-receiving section 21B is conjugate with the eyeground of the eye 100 under measurement and others. The second conversion member 22B of the second light-receiving optical system 20B is conjugate with the pupil (iris) of the eye 100 under measurement and others.

(Electrical-System Configuration)

The structure of an electrical system according to the second embodiment can be the same as the structure of the electrical system according to the first embodiment. The calculation section 600 further receives a second signal (14) from the second light-receiving section 21B, and obtains the optical characteristics of the eye 100 under measurement according to the second signal (14).

(Flowchart)

Figure 8:
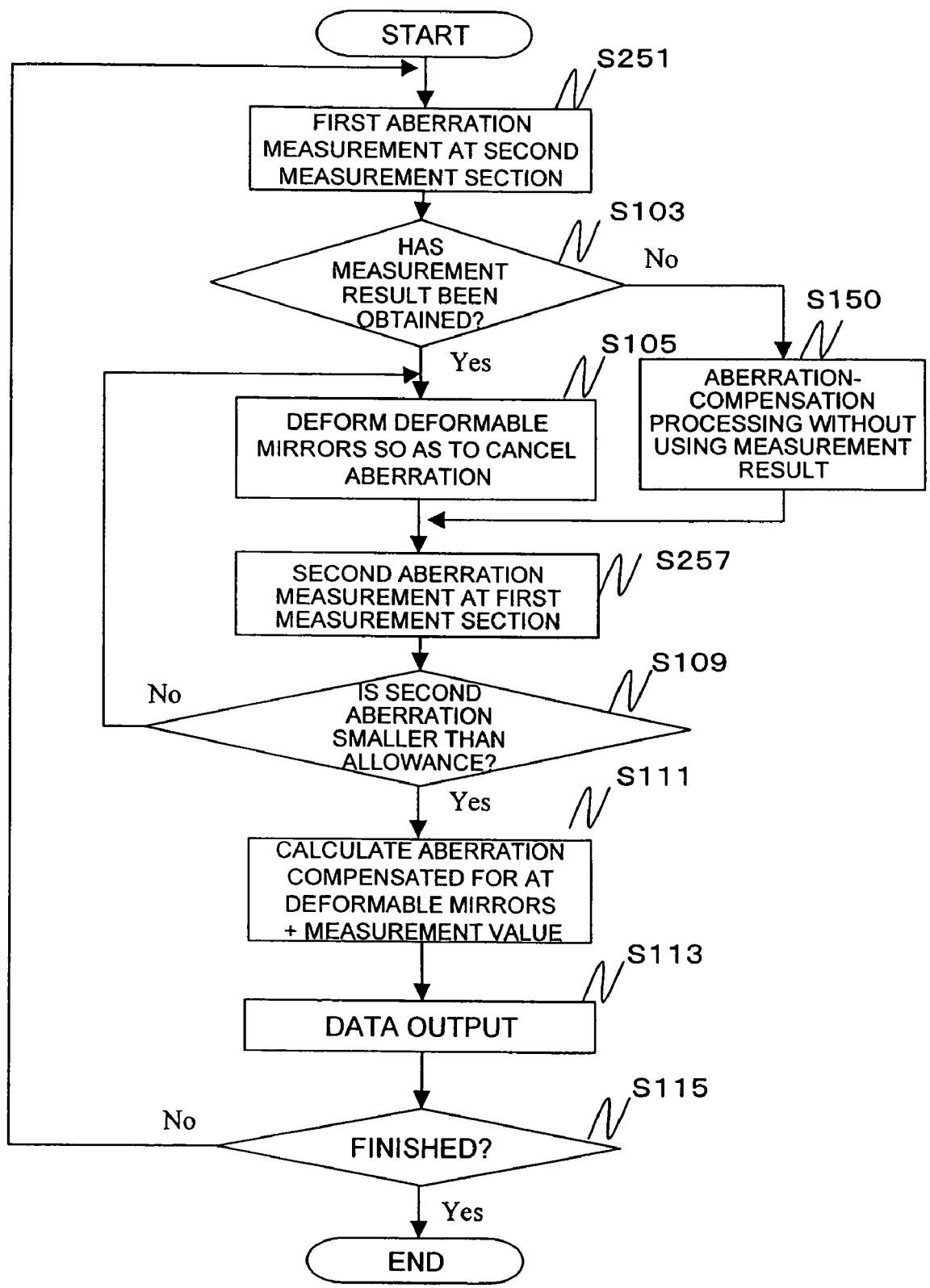
FIG. 8 is a flowchart of aberration measurement which uses the optical system according to the second embodiment.

FIG. 8 is a flowchart of aberration measurement which uses the optical system according to the second embodiment. FIG. 8 is a flowchart of aberration measurement which determines the amount of compensation according to a signal sent from the second light-receiving optical system 20B having a short focal length, a low sensitivity, and/or a high density. The calculation section 600 allows high-sensitivity and high-speed measurement by obtaining the amount M of compensation for the first and second compensation optical sections 60A and 60B according to the output from the second measurement section 25B at a high speed and by precisely measuring a light beam for which aberration is compensated for by the first measurement section 25A having a long focal length and/or a high sensitivity.

The calculation section 600 performs first aberration measurement according to a signal sent from the second measurement section 25B having a short focal length, a low sensitivity, and a high density (S251). The calculation section 600 obtains the second signal of the Hartmann image from the second light-receiving section 21B of the second measurement section 25B, and detects the center of gravity of the spot image according to the obtained image. The center of gravity associated with the spot is searched for in a rectangular area whose center is located at the center of gravity obtained at no aberration, and association is executed so as to be able to be at a high speed. The calculation section 600 obtains rough aberration of the eye 100 under measurement according to the obtained center of gravity of the spot image.

Then, the calculation section 600 executes the processes of steps S103, S105, and S150. The details of the processes are the same as those described above, and a description thereof is omitted.

The calculation section 600 performs a second aberration measurement according to a signal sent from the first measurement section 25A having a long focal length and a high sensitivity (S257). The calculation section 600 receives the first signal of the Hartmann image from the first light-receiving section 21A of the first measurement section 25A. Then, the calculation section 600 obtains the point-image movement distances of the Hartmann image from the received first signal, and obtains the optical characteristics of the eye under measurement according to the point-image movement distances. In conventional aberration measurement which uses a measurement section having a long focal length and/or a high sensitivity, the spot images may have large shifts and the association of the spot images takes long time. Alternatively, the association cannot be obtained, and therefore measurement cannot be performed in some cases. In the present embodiment, since the first signal of the Hartmann image for which the aberration of the eye 100 under measurement has been canceled to some extent is received, even if a long focal length and/or a high sensitivity is provided, the positional shift of a spot is small, and therefore, precise, quick aberration measurement is possible.

Next, the calculation section 600 executes the processes of steps S109 to S115. The details of the processes are the same as those described above, and a description thereof is omitted. As shown in the modification shown in FIG. 6, aberration calculation for the eye 100 under measurement and the output of the calculation result may be performed each time aberration measurement is performed after compensation.

3. THIRD EMBODIMENT

Figure 9:
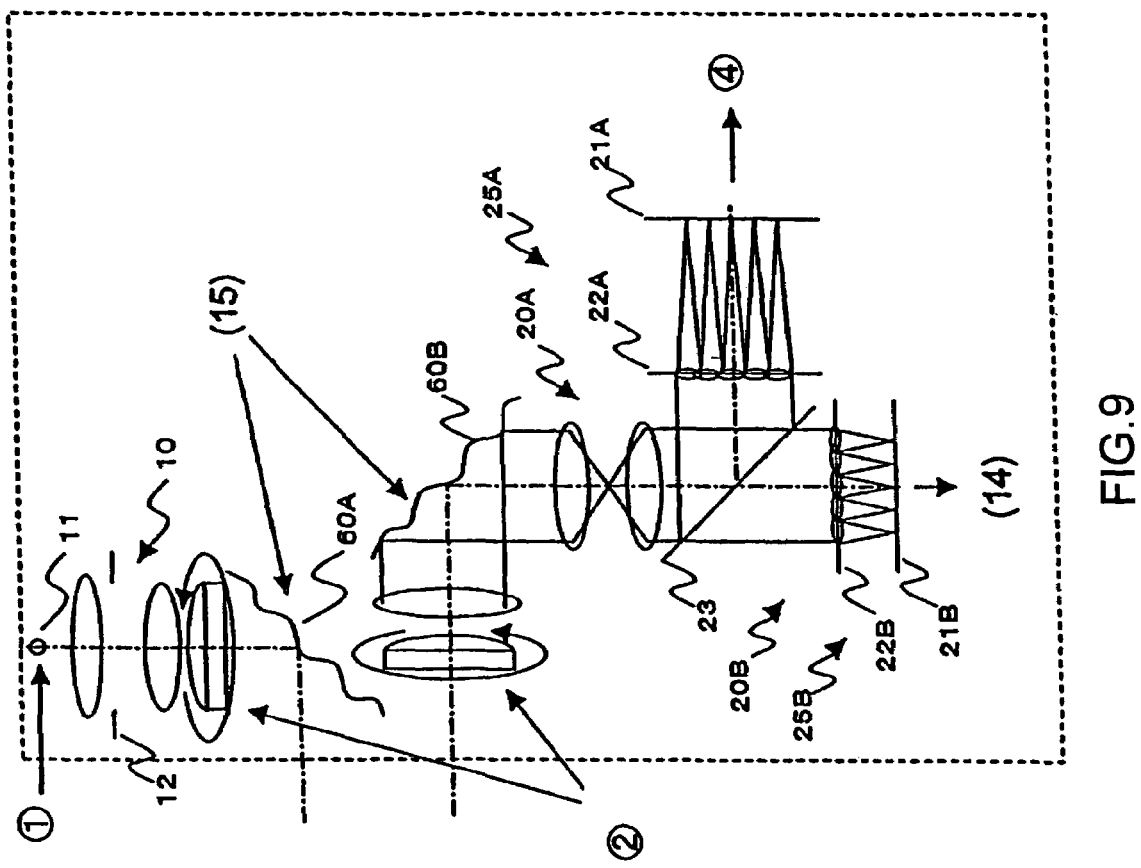
FIG. 9 is a view showing the structure of an optical system according to a third embodiment.

FIG. 9 is a view showing the structure of an optical system according to a third embodiment. FIG. 9 shows only a portion corresponding to that enclosed by the dotted line in FIG. 1, but the other portions are the same as those shown in FIG. 1. In the optical system shown in FIG. 9, a second compensation optical section 60B is inserted in common into first and second measurement sections 25A and 25B. A light beam reflected and returned from the retina of an eye 100 under measurement is led to the first and second measurement sections 25A and 25B through the second compensation optical section 60B. Since the optical beam is led to the second measurement section 25B through the second compensation optical section 60B, aberration obtained after compensation can be measured even in the second measurement section 25B. In addition, it is possible that the first and second compensation optical sections 60A and 60B are deformed until aberration measured at the output of the second measurement section 25B becomes equal to or smaller than an allowance specified in advance. A first conversion member 22A used in the optical system according to the third embodiment is a wavefront conversion member having a long focal length and/or a high sensitivity. The optical system according to the third embodiment, described above, is configured for double-path measurement. It can be changed for single-path measurement, if necessary.

The structure of an electrical system according to the third embodiment can be the same as the structure of the electrical system according to the second embodiment. A flowchart of aberration measurement which uses the optical system according to the third embodiment can be the flowchart shown in FIG. 8.

4. FOURTH EMBODIMENT

In the present embodiment, aberration (compensation aberration) actually compensated for by first and second compensation optical sections 60A and 60B is further measured, and the optical characteristics of the eye 100 under measurement is obtained according to the measured compensation aberration and aberration included in a light beam reflected from the eye under measurement after the compensation. If there is an error between an input value at a compensation optical section and the actual compensation aberration, more precise measurement is possible.

Figure 10:
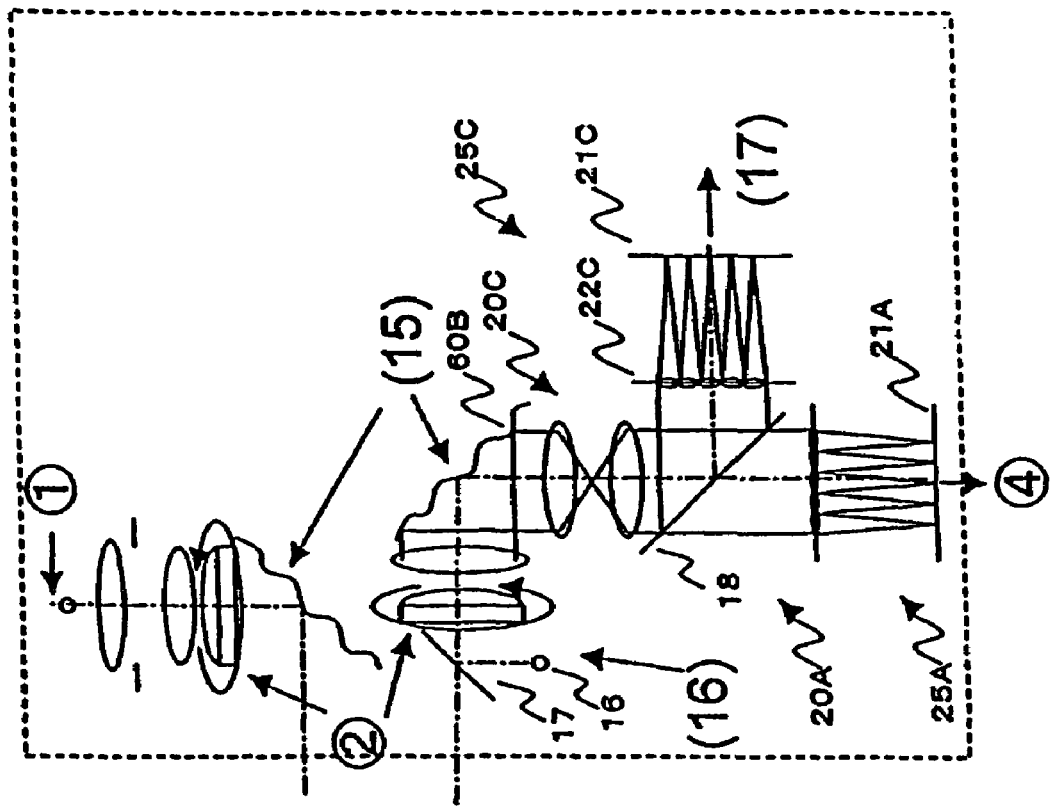
FIG. 10 is a view showing the structure of an optical system according to a fourth embodiment.

FIG. 10 is a view showing the structure of an optical system according to a fourth embodiment. The optical system shown in FIG. 10 is obtained by adding an optical system for measuring compensation aberration to the optical system used in the first embodiment, shown in FIG. 1, and further includes a third light-source section 16, beam splitters 17 and 18, and a third measurement section 25C. The third measurement section 25C includes a third light-receiving optical system 20C and a third light-receiving section 21C. The other portions are the same as those shown in FIG. 1. FIG. 10 shows only a portion corresponding to that enclosed by the dotted line in FIG. 1, but the other portions are the same as those shown in FIG. 1.

The third light-source section 16 emits a light beam having a third wavelength. The light beam emitted from the third light-source section 16 is used, for example, for measuring aberration (second compensation aberration) compensated for by a second compensation optical section 60B. The light beam emitted from the third light-source section 16 is reflected by the beam splitter 17 through a lens to illuminate the second compensation optical section 60B. For example, the light beam emitted from the third light-source section 16 is always incident on the second compensation optical section 60B as parallel light. A light beam having aberration because it is reflected from or transmits the second compensation optical section 60B is reflected by the beam splitter 18, is received by the third light-receiving optical system 20C, and its aberration is measured. The beam splitters 17 and 18 can, for example, be dichroic mirrors which transmit a light beam having a first wavelength emitted from a first light-source section 11 and which reflect a light beam having the third wavelength emitted from the third light-source section 16. In this case, the third wavelength emitted from the third light-source section 16 should be different from the first wavelength emitted from the first light-source section 11. The light beam emitted from the third light-source section 16 may be light having a polarization direction opposite that of a light beam reflected from the eye 100 under measurement. This can be implemented by using a polarization beam splitter which transmits the polarization direction of the reflected light beam from the retina of the eye 100 under measurement and which reflects the opposite polarization direction. The beam splitter 18 can, for example, be a polarization beam splitter to divide into the reflected light beam from the eye 100 under measurement and the light beam from the third light-source section 16. The beam splitter 17 can also be a half mirror. The third light-source section 16 is conjugate with the retina of the eye 100 under measurement and others. In the present embodiment, the reflected light beam from the retina of the eye 100 under measurement is transmitted and led to the first light-receiving section 21A, and the light beam from the third light-source section 16 is reflected and led to the third light-receiving section 21C. It may be configured that the relationship between the reflection and transmission is reversed, and the light-receiving sections are interchanged to perform measurement.

The third light-receiving optical system 20C receives a light beam emitted from the third light-source section 16 and reflected by the second compensation optical section 60B and leads it to the third light-receiving section 21C. The third light-receiving optical system 20C includes, for example, a third conversion member 22C (such as a Hartmann plate), and an afocal lens, variable cross cylinders, and a relay lens which are shared with the first light-receiving optical system 20A. The third conversion member 22C is a wavefront conversion member having a lens section for converting the reflected light beam from the second compensation optical section 60B to a plurality of at least 17 light beams. The third conversion member 22C can be a plurality of micro Fresnel lenses disposed on a plane perpendicular to the optical axis. The light beam from the third light-source section 16 is collected to the third light-receiving section 21C through the second compensation optical section 60B and the third conversion member 22C. The third light-receiving section 21C receives the light coming from the third light-receiving optical system 20C and passing through the third conversion member 22C to generate a third signal. The light beams of the first light-receiving optical system 20A and the third light-receiving optical system 20C can be divided, for example, by the beam splitter 18. In the present embodiment, the reflected light beam from the retina of the eye 100 under measurement is transmitted and led to the first light-receiving section 21A, and the light beam from the third light-source section 16 is reflected and led to the third light-receiving section 21C. It may be configured that the relationship between the reflection and transmission is reversed, and the light-receiving sections are interchanged to perform measurement.

In FIG. 10, the optical system is disposed so as to measure the second compensation aberration at the second compensation optical section 60B. The optical system may be disposed so as to measure compensation aberration (first compensation aberration) at the first compensation optical section 60A. In this case, the third light-source section 16 can also serve as the first light-source section 11.

The structure of an electrical system according to the fourth embodiment can be the same as the structure of the electrical system according to the first embodiment. A calculation section 600 further receives a third signal (17) from the third light-receiving section 21C, and calculates compensation aberration at the second compensation optical section 60B according to the third signal (17). A control section 610 further outputs a signal (16) to the third light-source section 16.

Figure 11:
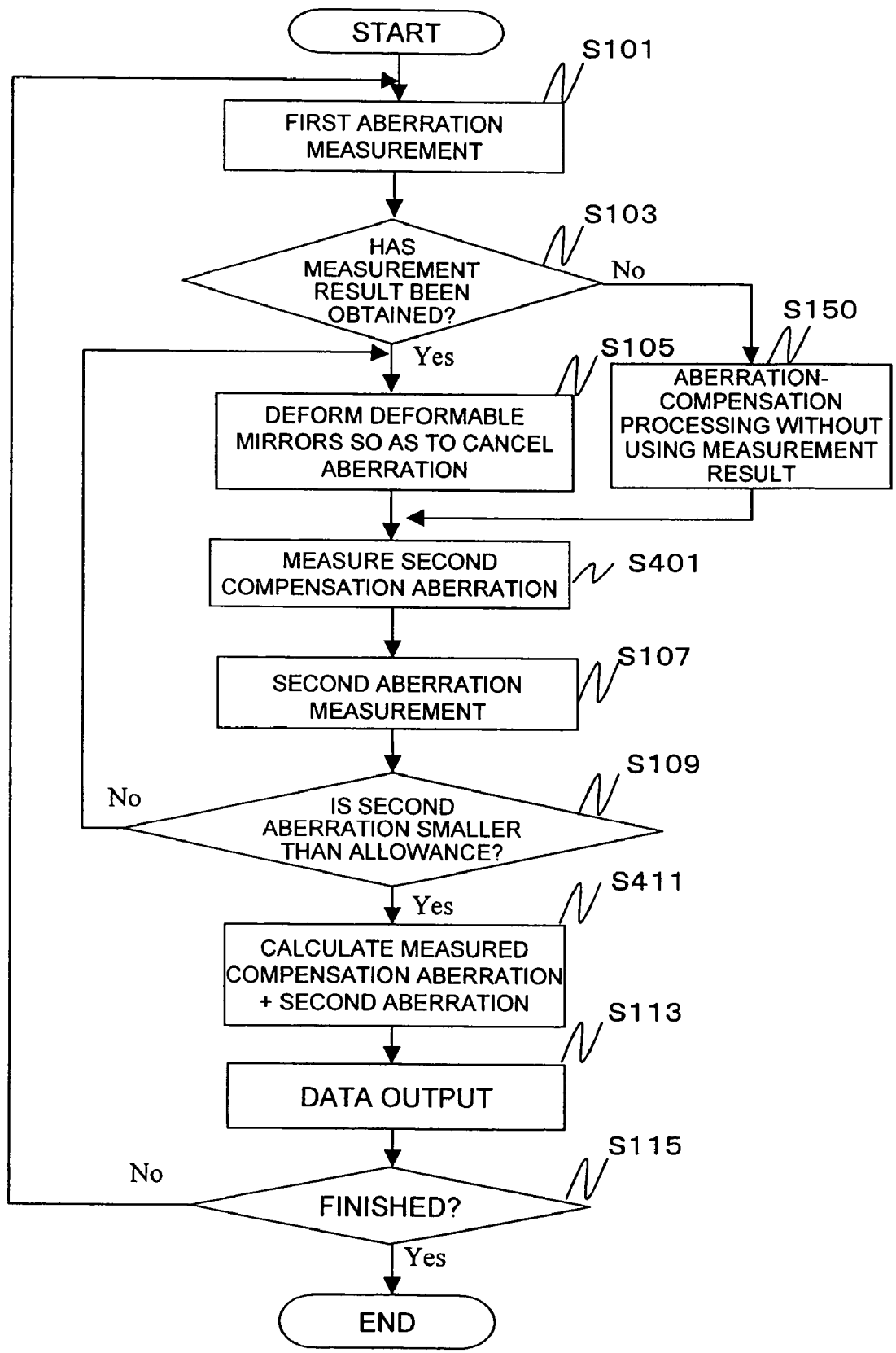
FIG. 11 is a flowchart of aberration measurement which uses the optical system according to the fourth embodiment.

FIG. 11 is a flowchart of aberration measurement which uses the optical system according to the fourth embodiment. In the flowchart shown in FIG. 11, the aberration actually compensated for by the second compensation optical section 60B is further measured, and the optical characteristics of the eye 100 under measurement is obtained with the measured aberration being taken into account, in addition to the flowchart shown in FIG. 3.

The calculation section 600 executes the processes of steps S101 to S105, and S150. The details of the processes are the same as those described above, and a description thereof is omitted. Then, the calculation section 600 measures second compensation aberration (S401). The calculation section 600 receives the third signal from the third light-receiving section 21C, and calculates the second compensation aberration compensated for by the second compensation optical section 60B, according to the received third signal. The aberration calculation is the same as that described above. The calculation section 600 executes the processes of steps S107 and S109. The details of the processes are the same as those described above, and a description thereof is omitted. The processes of steps S401 and S107 may be executed in the reverse order, or executed in parallel.

The calculation section 600 adds the second compensation aberration measured in step S401 to the aberration measured in step S107 to obtain the aberration W of the eye 100 under measurement (S411). The calculation section 600 may obtain optical characteristics such as the spherical power. Calculation details are the same as in step S111 shown in FIG. 3. Next, the calculation section 600 executes the processes of steps S113 and S115. The details of the processes are the same as those described above, and a description thereof is omitted. Compensation-aberration measurement may be performed by appropriately arranging an optical system and measuring compensation aberration at the first compensation optical section 60A. As shown in the modification shown in FIG. 6, aberration calculation for the eye 100 under measurement and the output of the calculation result may be performed each time aberration measurement is performed after compensation.

Figure 12:
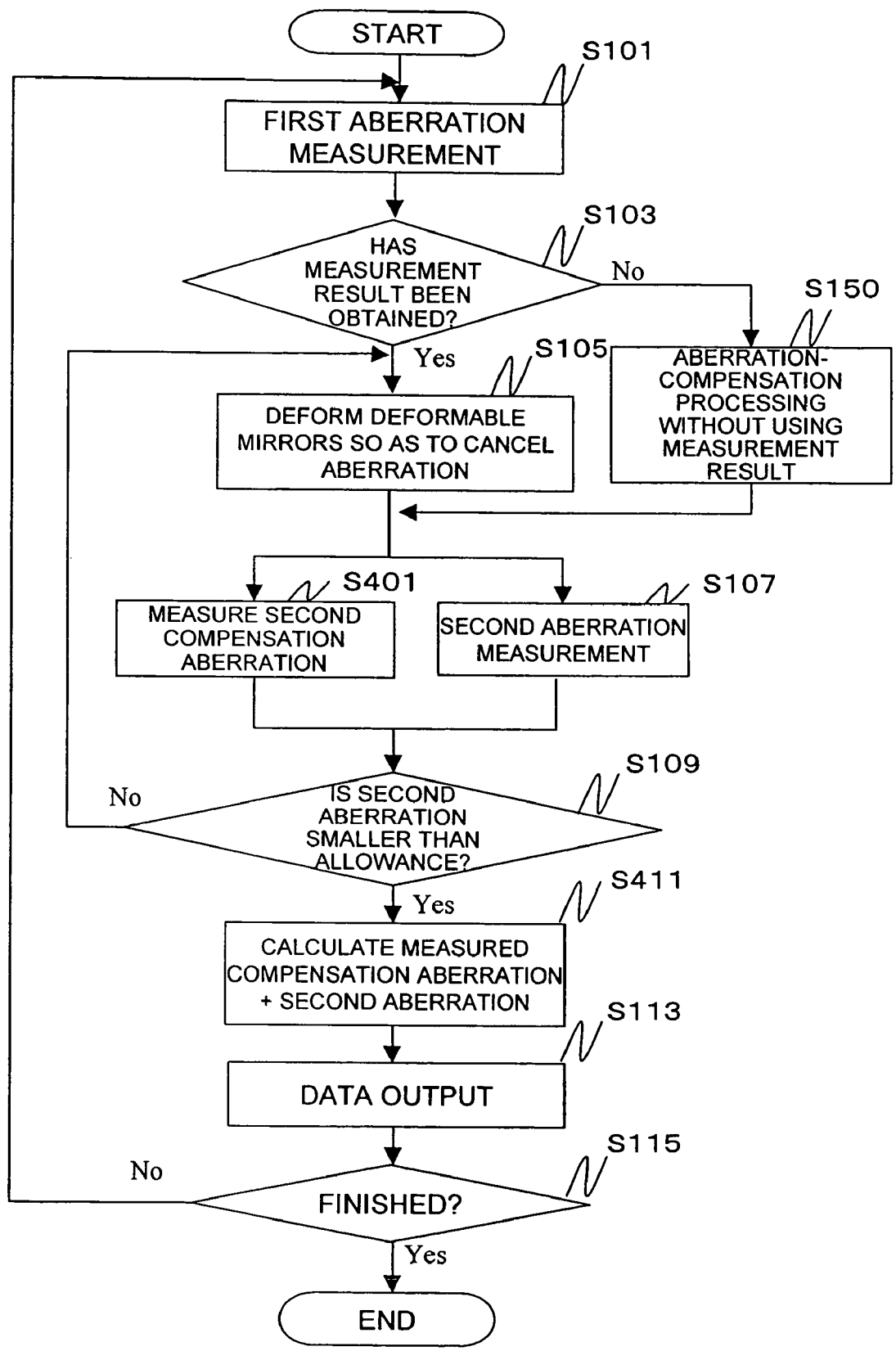
FIG. 12 is a modification of the flowchart of aberration measurement which uses the optical system according to the fourth embodiment.

FIG. 12 is a modification of the flowchart of the aberration measurement which uses the optical system according to the fourth embodiment. In the flowchart shown in FIG. 12, the measurement (S401) of the second compensation aberration and the second aberration measurement (S107) of the reflected light beam from the eye 100 under measurement, both shown in the flowchart of FIG. 11, are executed in parallel. Calculations may be performed by parallel calculations with the use of a plurality of calculation sections. Since the process of each step is the same as that shown in FIG. 11, the same symbols are assigned, and a detailed description thereof is omitted here.

5. FIFTH EMBODIMENT

Figure 13:
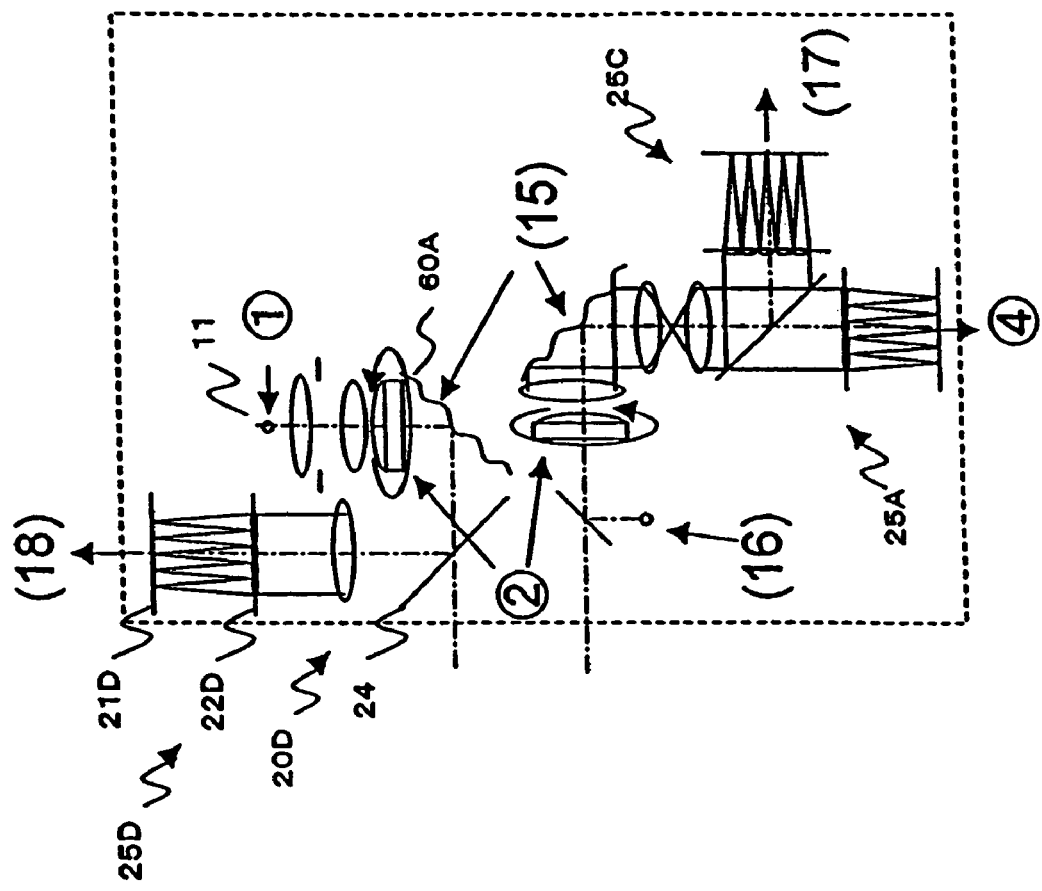
FIG. 13 is a view showing the structure of an optical system according to a fifth embodiment.

FIG. 13 is a view showing the structure of an optical system according to a fifth embodiment. The optical system shown in FIG. 13 is obtained by further adding a fourth measurement section 25D for measuring aberration (first compensation aberration) compensated for by a first compensation optical section 60A to the optical system used in the fourth embodiment, shown in FIG. 10. The fourth measurement section 25D includes a fourth light-receiving optical system 20D and a fourth light-receiving section 21D. The other portions are the same as those shown in FIG. 10. FIG. 13 shows only a portion corresponding to that enclosed by the dotted line in FIG. 1, but the other portions are the same as those shown in FIG. 1.

The fourth light-receiving optical system 20D receives a light beam emitted from the first light-source section 11 and reflected by the first compensation optical section 60A and leads it to the fourth light-receiving section 21D. The fourth light-receiving optical system 20D includes a fourth conversion member 22D (such as a Hartmann plate) and a lens. The fourth conversion member 22D is a wavefront conversion member having a lens section for converting the light beam reflected from the first compensation optical section 60A to a plurality of at least 17 light beams. The fourth conversion member 22D can be a plurality of micro Fresnel lenses disposed on a plane perpendicular to the optical axis. The light beam from the first light-source section 11 is collected to the fourth light-receiving section 21D through the first compensation optical section 60A, a beam splitter 24, and the fourth conversion member 22D. The fourth light-receiving section 21D receives the light coming from the fourth light-receiving optical system 20D and passing through the fourth conversion member 22C to generate a fourth signal. Light beams towards the fourth light-receiving optical system 20D and the eye 100 under measurement are divided by the beam splitter 24. Alternatively, instead of the beam splitter 24, a mirror can be used such that the mirror is moved and inserted into the optical path to switch a light beam between the fourth light-receiving optical system 20D and the eye 100 under measurement. The beam splitter 24 may be a polarization beam splitter.

The structure of an electrical system according to the fifth embodiment can be the same as the structure of the electrical system according to the fourth embodiment. A calculation section 600 further receives the fourth signal (18) from the fourth light-receiving section 21C, and calculates compensation aberration (first compensation aberration) at the first compensation optical section 60A according to the fourth signal (18).

Figure 14:
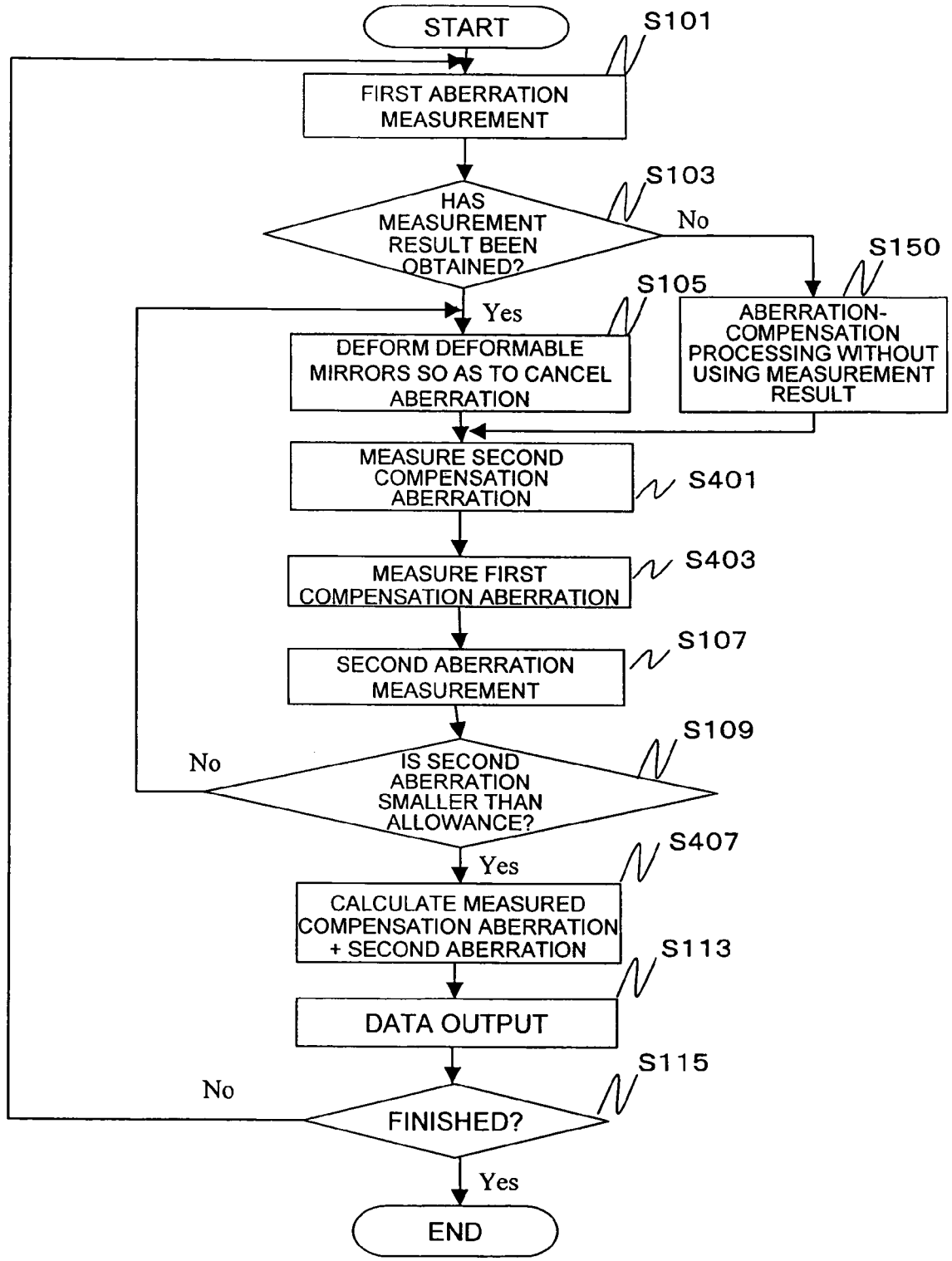
FIG. 14 is a flowchart of aberration measurement which uses the optical system according to the fifth embodiment.

FIG. 14 is a flowchart of aberration measurement which uses the optical system according to the fifth embodiment. In the flowchart shown in FIG. 14, the first compensation aberration of the first compensation optical section 60A is further measured, in addition to the flowchart shown in FIG. 11. First, the calculation section 600 executes the processes of steps S101 to S105, S150, and S401. The details of the processes are the same as those described above, and a description thereof is omitted. Then, the calculation section 600 measures the first compensation aberration (S403). The calculation section 600 receives the fourth signal from the fourth light-receiving section 21D, and calculates the first compensation aberration compensated for by the first compensation optical section 60A, according to the received fourth signal. The aberration calculation is the same as that described above. The first compensation aberration actually compensated for by the first compensation optical section 60A and measured by the fourth measurement section 25D indicates whether a minute area on the eyeground of the eye 100 under measurement is illuminated. If the difference between the measured first compensation aberration and second compensation aberration is equal to or larger than an allowance specified in advance, for example, the calculation section 600 may further compensate the first compensation optical section 60A and the second compensation optical section 60B according to the difference to make the difference equal to or smaller than the allowance. Aberration obtained after the compensation is not smaller than the allowance in some cases because the amount of compensation determined according to aberration measured by using the output of the first light-receiving section 25A is not correctly brought to the first compensation optical section 60A, and therefore, a minute area is not formed on the eyeground, or for some reason. In that case, when the processing returns to step S105 by a process shown later, the calculation section 600 may re-adjusts the amount of compensation for the first compensation optical section 60A according to the first compensation aberration measured in step S403. The calculation section 600 can, for example, compare the input value to the first compensation optical section 60A with the measured first compensation aberration to determine whether to perform re-adjustment. The processes of steps S401 and S403 may be executed in the reverse order, or executed in parallel.

Further, the calculation section 600 executes the processes of steps S107 and S109. The details of the processes are the same as those described above, and a description thereof is omitted. Then, the calculation section 600 adds the second compensation measured in step S107 to the measured second compensation aberration to obtain the aberration W of the eye 100 under measurement (S407). The calculation section 600 may obtain optical characteristics such as the spherical power. Calculation details are the same as in step S111 shown in FIG. 3. Next, the calculation section 600 executes the processes of steps S113 and S115. The details of the processes are the same as those described above, and a description thereof is omitted. The processes of steps S401 and S403, and the process of step S107 may be executed in the reverse order, or executed in parallel. As shown in the modification shown in FIG. 6, aberration calculation for the eye 100 under measurement and the output of the calculation result may be performed each time aberration measurement is performed after compensation.

6. SIXTH EMBODIMENT

Figure 15:
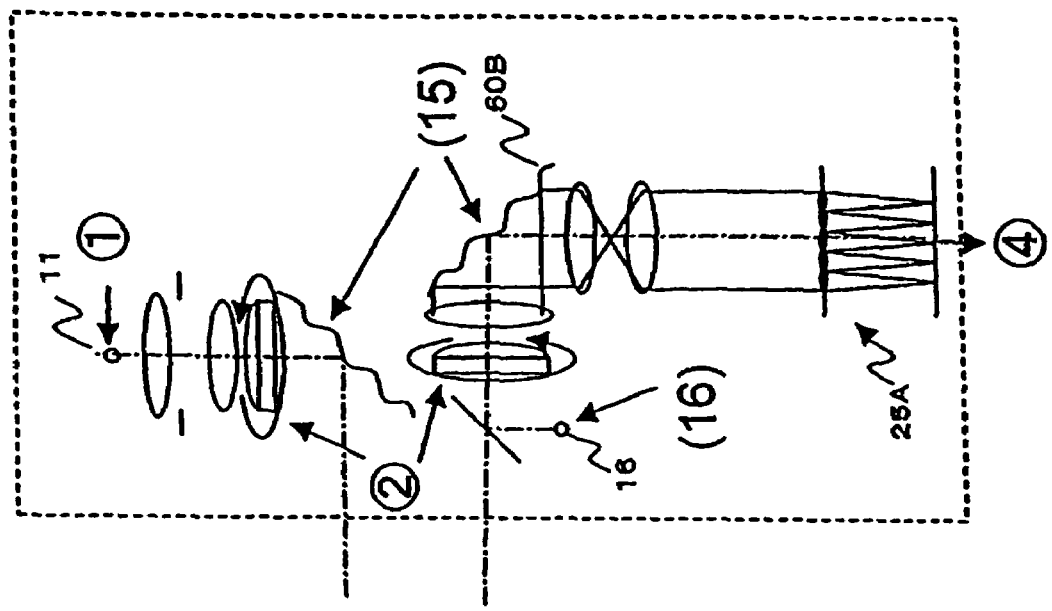
FIG. 15 is a view showing the structure of an optical system according to a sixth embodiment.

FIG. 15 is a view showing the structure of an optical system according to a sixth embodiment. In the optical system shown in FIG. 15, one of the first measurement section 25A and the third measurement section 25C used in the optical system according to the fourth embodiment, shown in FIG. 10 serves as both. By switching a light beam coming from a first light-source section 11 and a light beam coming from a third light-source section 16, one measurement section can receive a light beam reflected from the eye 100 under measurement and a light beam emitted from the third light-source section 16 and reflected from a second compensation optical section 60B. For example, by controlling turning on and off of the first light-source section 11 and the third light-source section 16, or by controlling means for blocking a light beam, such as a chopper, provided before the first and third light-source sections 11 and 16, the light beam incident into a first light-receiving optical system 20A can be switched. Instead of a chopper, appropriate light-beam blocking means, such as a mirror inserted into the optical path, may be used. The other portions are the same as shown in FIG. 10. FIG. 15 shows only a portion corresponding to that enclosed by the dotted line in FIG. 1, but the other portions are the same as those shown in FIG. 1.

The structure of an electrical system according to the sixth embodiment can be the same as the structure of the electrical system according to the first embodiment. A control section 610 further outputs a signal (16) to the third light-source section 16.

Figure 16:
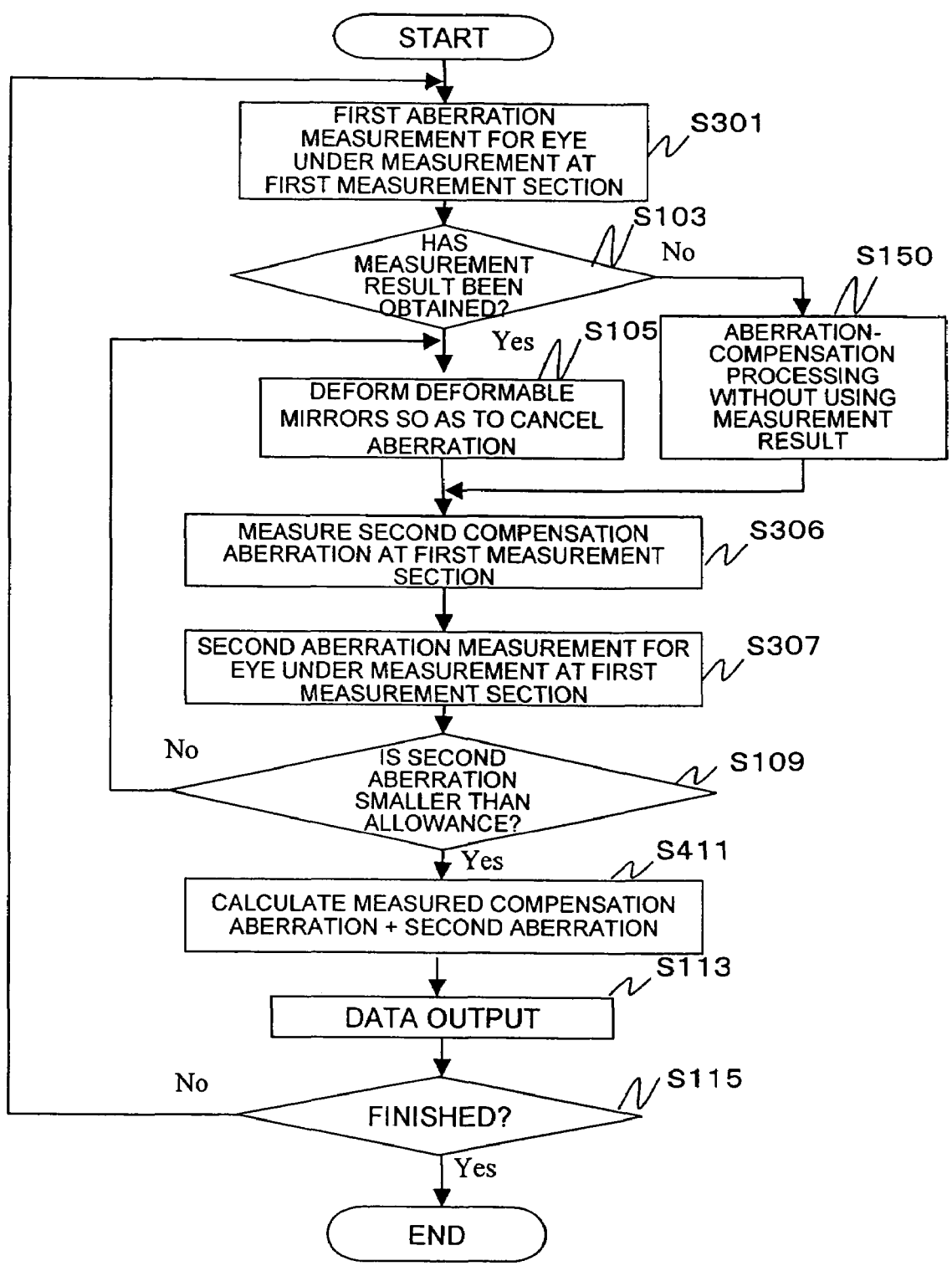
FIG. 16 is a flowchart of aberration measurement which uses the optical system according to the sixth embodiment.

FIG. 16 is a flowchart of aberration measurement which uses the optical system according to the sixth embodiment. In the flowchart shown in FIG. 16, the measurement of second compensation aberration and the measurement of aberration obtained after compensation are performed according to the output of one measurement section.

First, the calculation section 600 performs first aberration measurement for the eye 100 under measurement according to the output of the first measurement section 25A (S301). The calculation section 600, for example, turns on the first light-source section 11 and turns off the third light-source section 16 to make a light beam reflected from the eye 100 under measurement incident on a first light-receiving optical system 20A, and receives a first signal from the first light-receiving section 21A. Then, the calculation section 600 obtains the aberration of the eye 100 under measurement according to the received first signal. Aberration calculation is the same as that described above. The calculation section 600 may further obtain the cornea shape, cornea aberration, and others according to a signal sent from an eye-front-part-image light-receiving section 41 of an eye-front-part observation section 40. The calculation section 600 stores these calculation results in a memory 800. Then, the calculation section 600 executes the processes of steps S103, S105, and S150. The details of the processes are the same as those described above, and a description thereof is omitted.

The calculation section 600 measures second compensation aberration according to the output from the first measurement section 25A (S306). The calculation section 600, for example, turns off the first light-source section 11 and turns on the third light-source section 16 to make a light beam emitted from the third light-source section 16 and reflected from the second compensation optical section 60B incident into the first light-receiving optical system 20a. The calculation section 600 further receives the first signal from the first light-receiving section 21A, and calculates the second compensation aberration according to the received first signal. The aberration calculation is the same as that described above. The calculation section 600 stores the obtained aberration in the memory 800.

Next, the calculation section 600 performs second aberration measurement for the eye 100 under measurement according to the output of the first measurement section 25A (S307). The details of the process is the same as in step S301. In the above-described process, the calculation section 600 turns on and off the first and third light-source sections 11 and 13 to switch the light beam incident into the first light-receiving optical system 20A. Means for blocking a light beam, such as a chopper, may be provided before the first and third light-source sections 11 and 16 and controlled, so that the light beam incident into the first light-receiving optical system 20A is switched. The processes of steps S306 and S307 may be executed in the reverse order. Since the subsequent processes are the same as those shown in FIG. 11, a description thereof is omitted. As shown in the modification shown in FIG. 6, aberration calculation for the eye 100 under measurement and the output of the calculation result may be performed each time aberration measurement is performed after compensation.

7. SEVENTH EMBODIMENT

Figure 17:
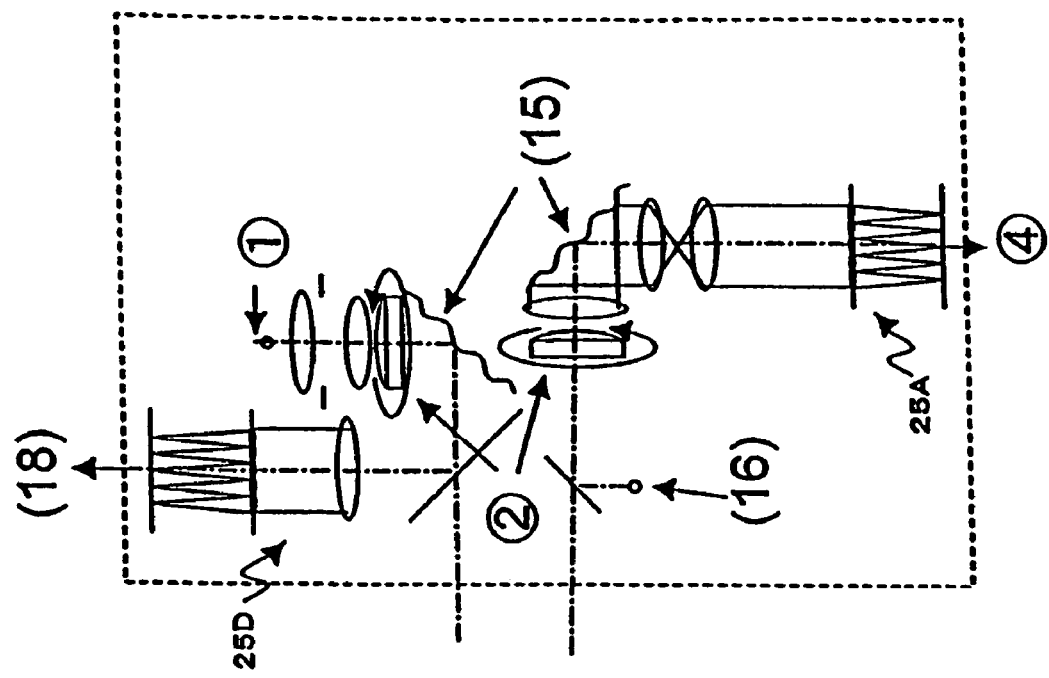
FIG. 17 is a view showing the structure of an optical system according to a seventh embodiment.

FIG. 17 is a view showing the structure of an optical system according to a seventh embodiment. The optical system shown in FIG. 17 is obtained by further adding a fourth measurement section 25D for measuring first compensation aberration compensated for by a first compensation optical section 60A to the sixth embodiment shown in FIG. 15. The fourth measurement section 25D includes a fourth light-receiving optical system 20D and a fourth light-receiving section 21D. In the same way as in the sixth embodiment, by switching a light beam coming from a first light-source section 11 and a light beam coming from a third light-source section 16, a light beam reflected from the eye 100 under measurement and a light beam emitted from the third light-source section 16 and reflected from a second compensation optical section 60B can be led to a first light-receiving optical system 20A. The other portions are the same as those shown in FIG. 13. FIG. 17 shows only a portion corresponding to that enclosed by the dotted line in FIG. 1, but the other portions are the same as those shown in FIG. 1.

The structure of an electrical system according to the seventh embodiment can be the same as the structure of the electrical system according to the sixth embodiment. A calculation section 600 further receives a fourth signal (18) from the fourth light-receiving section 21D, and calculates compensation aberration at a first compensation optical section 60A according to the fourth signal (18).

Figure 18:
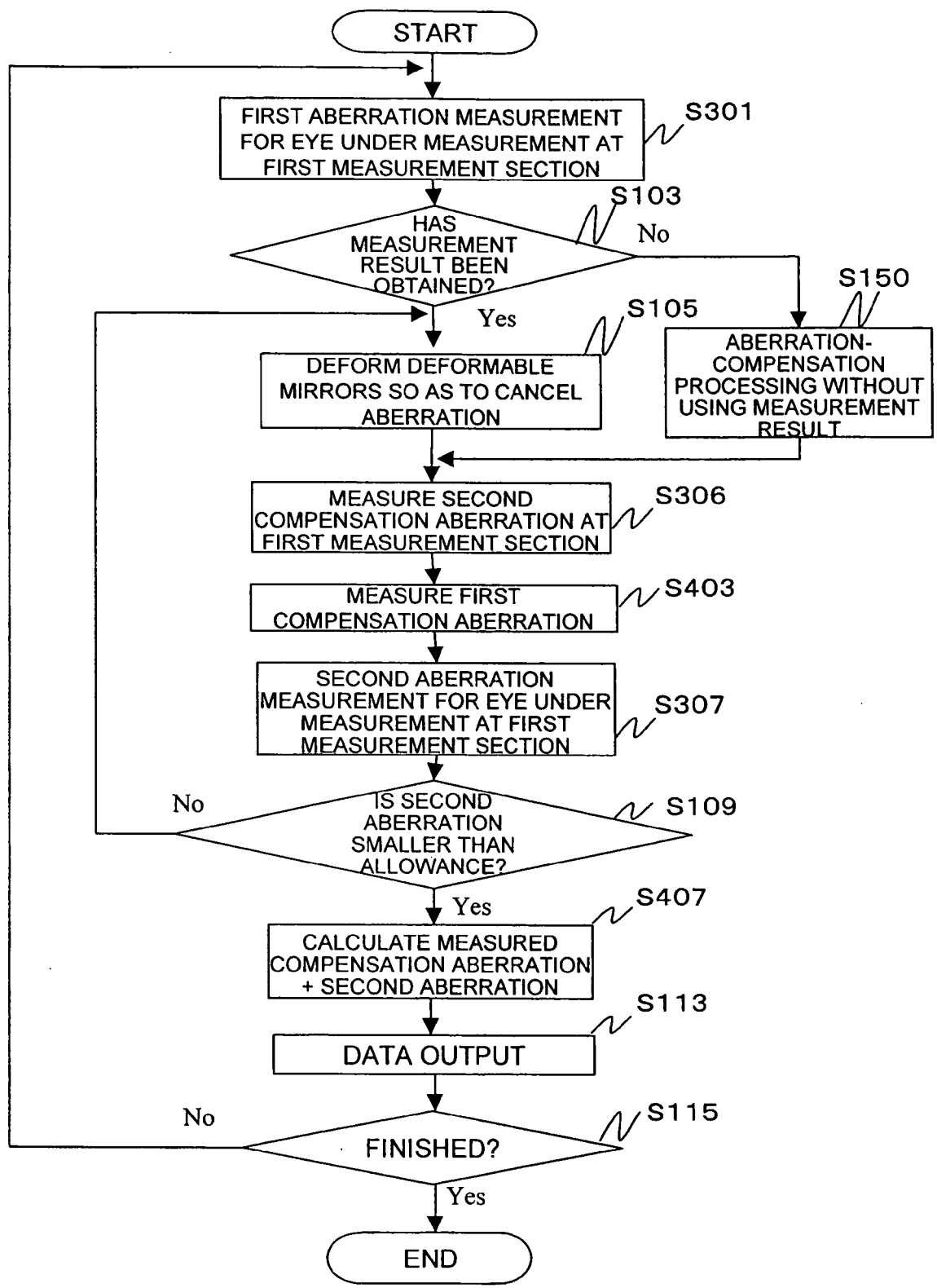
FIG. 18 is a flowchart of aberration measurement which uses the optical system according to the seventh embodiment.

FIG. 18 is a flowchart of aberration measurement which uses the optical system according to the seventh embodiment. In the flowchart shown in FIG. 18, the first compensation aberration is further measured, in addition to the flowchart shown in FIG. 16. Since the process of each step is the same as that shown in FIG. 14 and FIG. 16, the same symbol is assigned and a detailed description thereof is omitted. The processes of steps S306 and S403 may be executed in parallel. The processes of steps S306 and S403, and the process of step S307 may be executed in the reverse order. Further, as shown in the modification shown in FIG. 6, aberration calculation for the eye 100 under measurement and the output of the calculation result may be performed each time aberration measurement is performed after compensation.

8. EIGHTH EMBODIMENT

Figure 19:
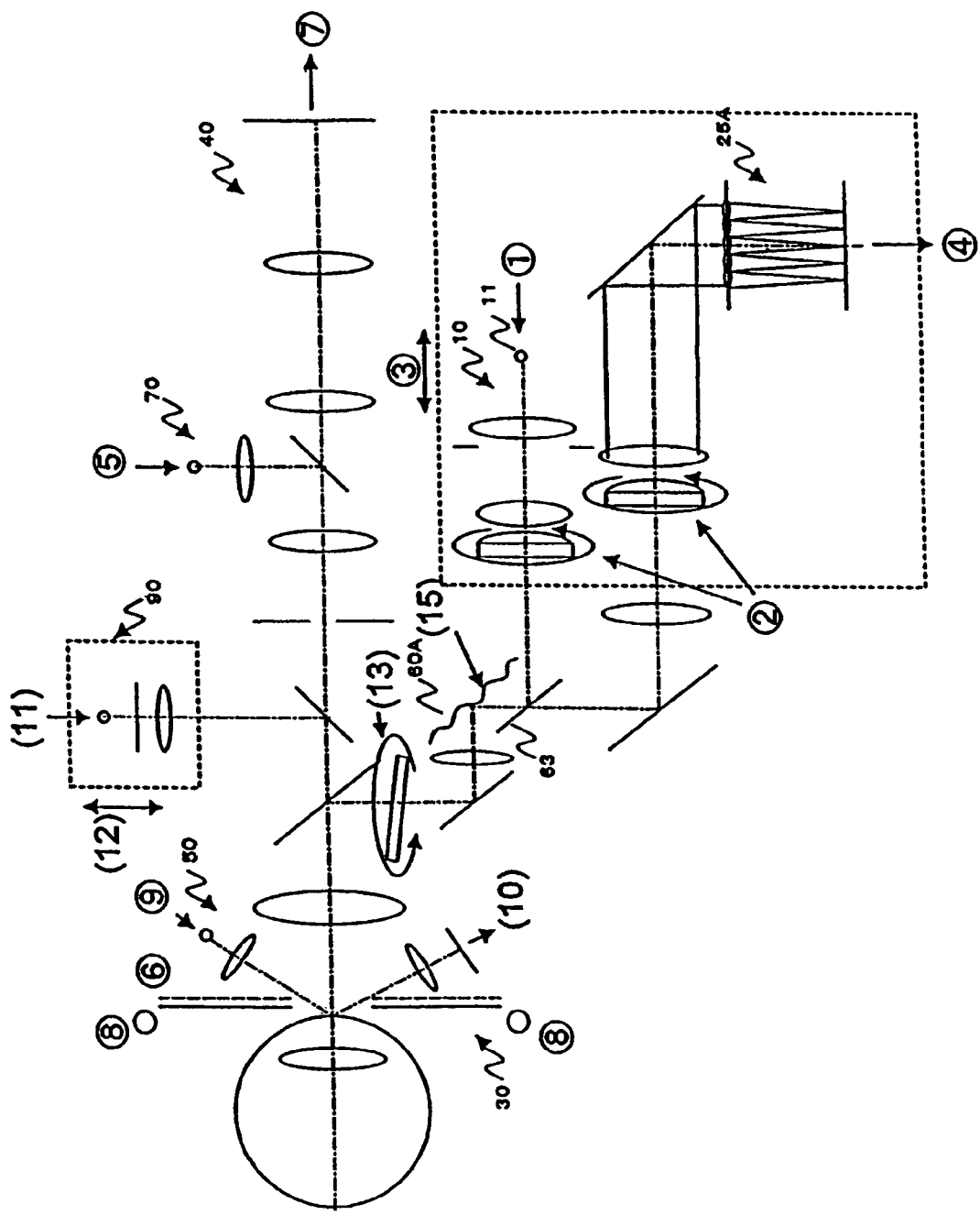
FIG. 19 is a view showing the structure of an optical system according to an eighth embodiment.

FIG. 19 is a view showing the structure of an optical system according to an eighth embodiment. In the optical system shown in FIG. 19, the first compensation optical section 60A and the second compensation optical section 60B used in the optical system according to the first embodiment, shown in FIG. 1, are made to be one section. The first compensation optical section 60A is inserted into the optical path common to light incident on the eye 100 under measurement and light reflected from the eye 100 under measurement. The details of each section is the same as in FIG. 1.

The structure of an electrical system according to the eighth embodiment can be the same as the structure of the electrical system according to the first embodiment. A flowchart of aberration measurement which uses the optical system according to the eighth embodiment can be the flowcharts of the first embodiment, shown in FIG. 3 and FIG. 4.

9. Modifications

The optical systems according to the fourth to eighth embodiments, described above, can be modified by further including a second measurement section 25B for measurement having one of a short focal length, a low sensitivity, and a high density. The modifications will be described below.

(First Modification of the Fourth Embodiment)

Figure 20:
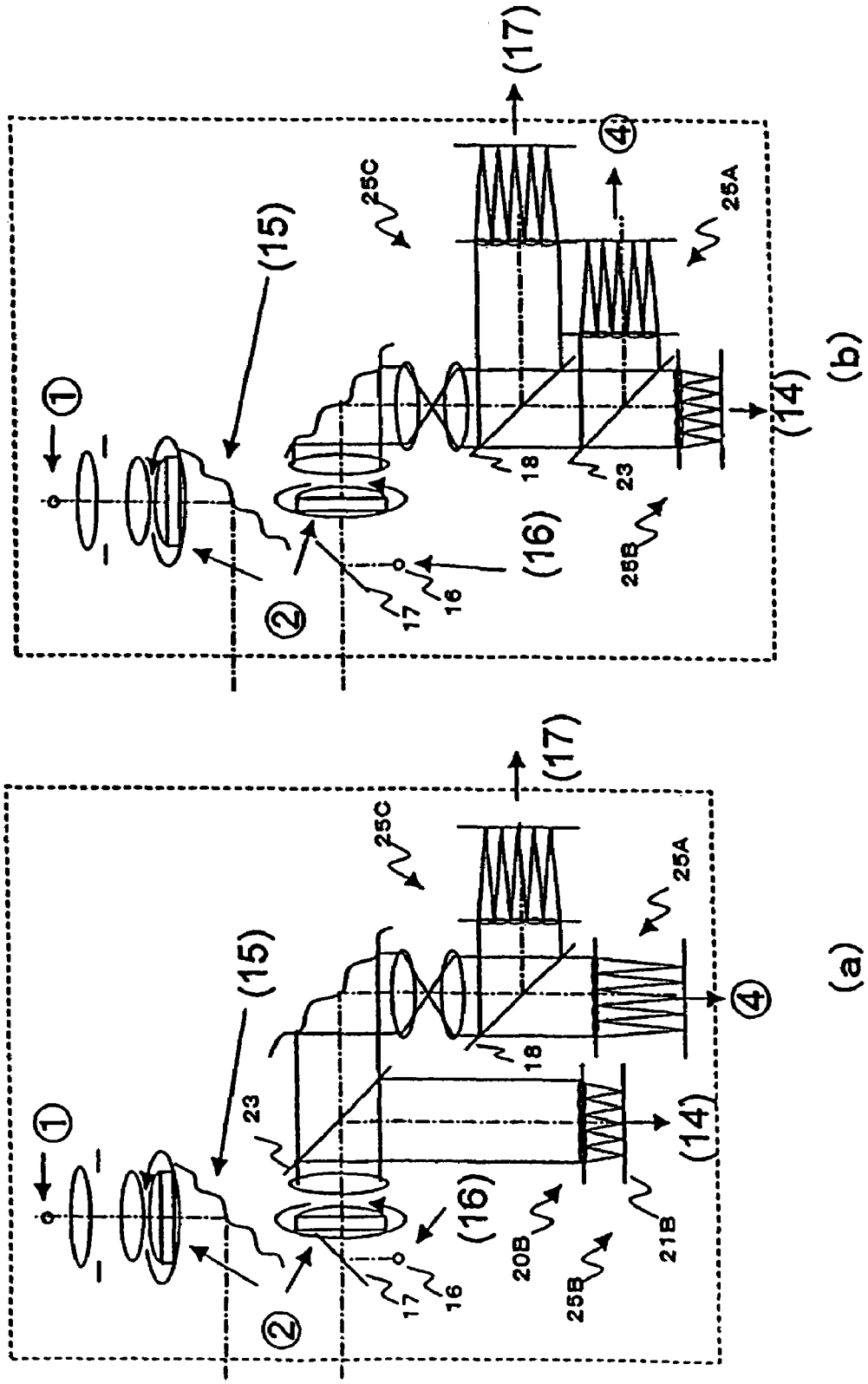
FIG. 20 is a view showing the structure of an optical system according to a first modification of the fourth embodiment.

FIG. 20 is a view showing the structures of optical systems according to a first modification of the fourth embodiment. An optical system shown in FIG. 20(a) is obtained by further adding a second measurement section 25B for measurement having a short focal length, a low sensitivity, and/or a high density, and a beam splitter 23 to the optical system according to the fourth embodiment, shown in FIG. 10. The second measurement section 25B includes a second light-receiving optical system 20B and a second light-receiving section 21B. The second light-receiving section 21B receives a light beam reflected from the eye 100 under measurement and divided into two by the beam splitter 23. In this case, for example, a third light-source section 16 is turned off such that a light beam coming from the third light-source section 16 is not incident on the second light-receiving optical system 20B. Other appropriate methods can be used, such as providing means for blocking a light beam before the third light-source section, such as a chopper, and dividing a light beam coming from the eye 100 under measurement and a light beam coming from the third light-source section 16 by a beam splitter. The other portions are the same as those shown in FIG. 10. An optical system shown in FIG. 20(b) is arranged such that a light beam reflected by the second compensation optical section 60B shown in FIG. 20(a) is also incident on the second measurement section 25B. A light beam coming through the second compensation optical section 60B is led to the second measurement section 25B to allow the second measurement section 25B also to measure aberration after compensation. It is possible that the first and second compensation optical sections 60A and 60B are deformed until aberration measured at the output of the second measurement section 25B is equal to or smaller than an allowance specified in advance. A first conversion member 22A used in the optical systems shown in FIG. 20(a) and FIG. 20(b) is a wavefront conversion member having a lens section with a long focal length and/or a high sensitivity. The other portions are the same as those shown in FIG. 10. FIG. 20(a) and FIG. 20(b) show only portions corresponding to that enclosed by the dotted line in FIG. 1, but the other portions are the same as those shown in FIG. 1.

The structure of an electrical system according to the first modification of the fourth embodiment can be the same as the structure of the electrical system according to the fourth embodiment. A calculation section 600 further receives a second signal (14) from the second light-receiving section 21B, and calculates the aberration of the eye 100 under measurement according to the second signal (14).

Figure 21:
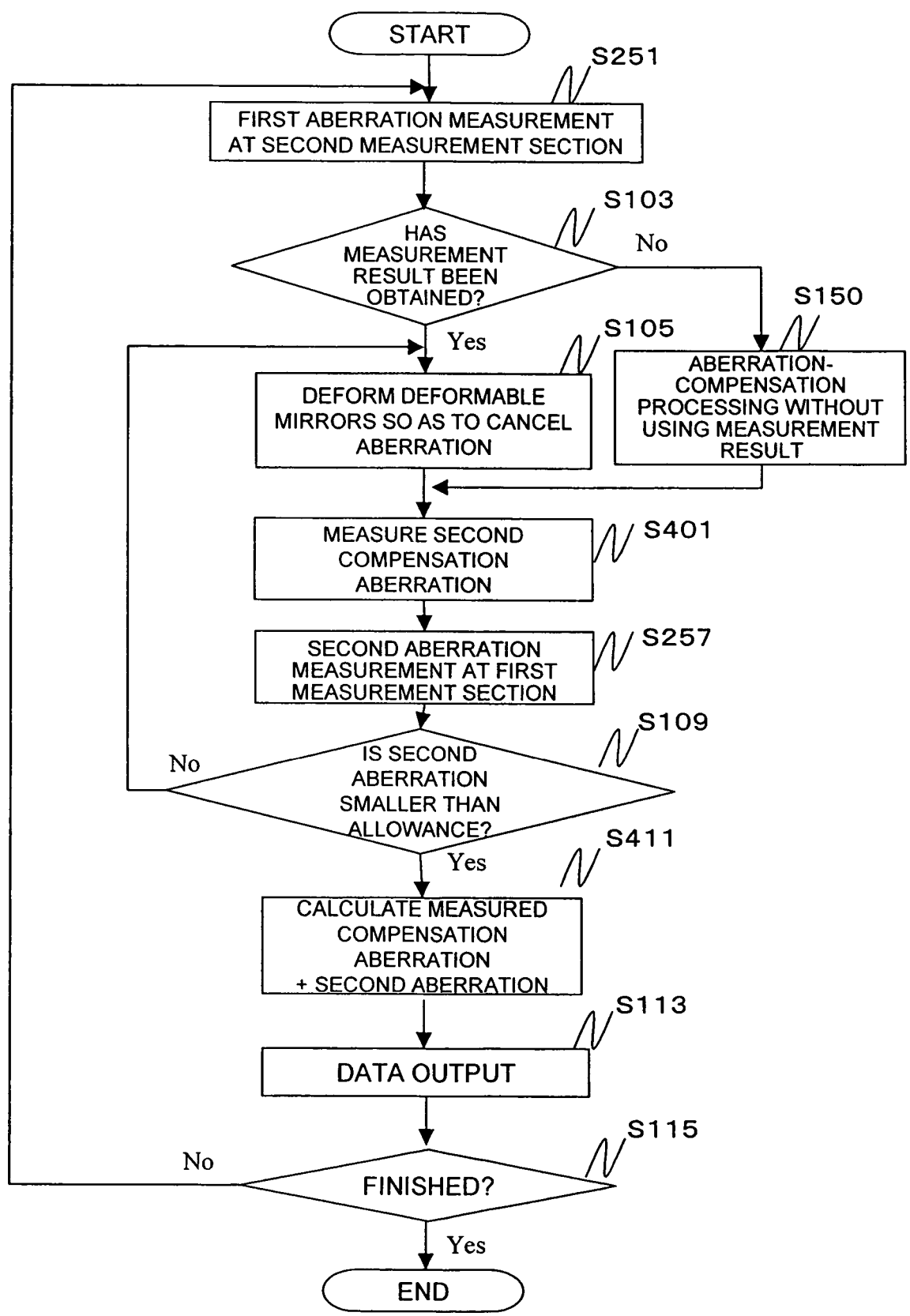
FIG. 21 is a flowchart of aberration measurement which uses the optical system according to the first modification of the fourth embodiment.

FIG. 21 is a flowchart of aberration measurement which uses an optical system according to the first modification of the fourth embodiment. The flowchart shown in FIG. 21 indicates a case, for example, in which the process of the first aberration measurement shown in the flowchart of FIG. 11 is performed according to the output of the second measurement section 25B. Since the process of each step is the same as that shown in FIG. 8 and FIG. 11, the same symbol is assigned and a detailed description thereof is omitted. The processes of steps S401 and S257 may be executed in the reverse order or in parallel. Further, as shown in the modification shown in FIG. 6, aberration calculation for the eye 100 under measurement and the output of the calculation result may be performed each time aberration measurement is performed after compensation.

(Modification of the Fifth Embodiment)

Figure 22:
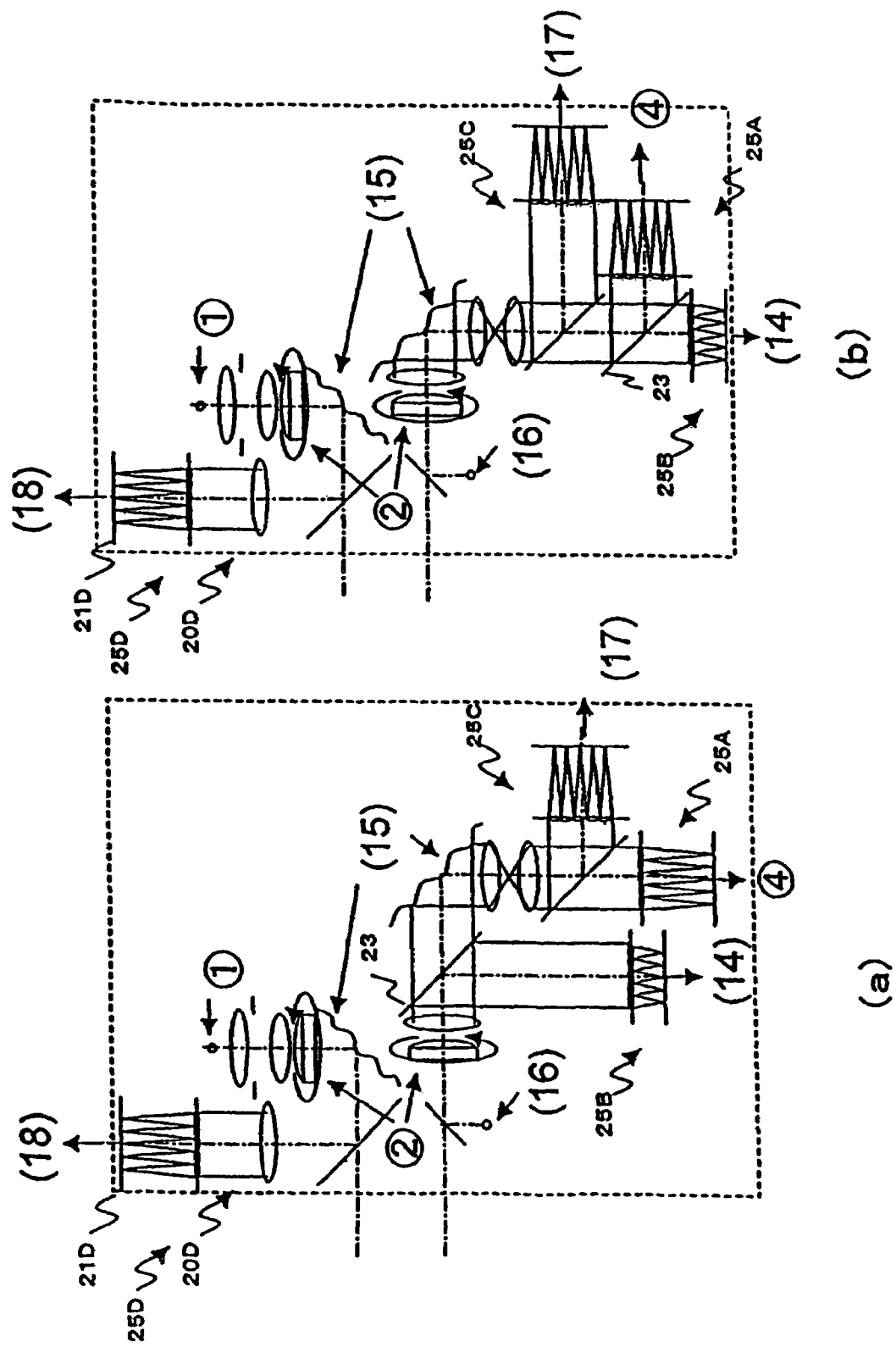
FIG. 22 is a view showing the structure of an optical system according to a modification of the fifth embodiment.

FIG. 22 is a view showing the structures of optical systems according to a modification of the fifth embodiment. An optical system shown in FIG. 22(a) is obtained by further adding a second measurement section 25B for measurement having a short focal length, a low sensitivity, and/or a high density, and a beam splitter 23 to the optical system according to the fifth embodiment, shown in FIG. 13. The second measurement section 25B includes a second light-receiving optical system 20B and a second light-receiving section 21B. The second light-receiving section 21B receives a light beam reflected from the eye 100 under measurement and divided into two by the beam splitter 23. In the same way as in the first modification of the fourth embodiment, when the second light-receiving section 21B receives the light beam reflected from the eye 100 under measurement, provision is made such that a light beam coming from the third light-source section 16 is not incident on the second light-receiving optical system 20B. The other portions are the same as those shown in FIG. 13. An optical system shown in FIG. 22(b) is arranged such that a light beam reflected by the second compensation optical section 60B shown in FIG. 22(a) is also incident on the second measurement section 25B. The optical system shown in FIG. 22(a) is modified such that a light beam coming through the second compensation optical section 60B is incident on the second measurement section 25B for measurement with a short focal length, a low sensitivity, and/or a high density. The second measurement section 25B needs to be for measurement with one of a short focal length, a low sensitivity, and a high density, but is preferably for measurement with a short focal length and a low sensitivity. A first conversion member 22A used in the optical systems shown in FIG. 22(a) and FIG. 22(b) is a wavefront conversion member having a lens section with a long focal length and/or a high sensitivity. The other portions are the same as those shown in FIG. 13. FIG. 22(a) and FIG. 22(b) show only portions corresponding to that enclosed by the dotted line in FIG. 1, but the other portions are the same as those shown in FIG. 1.

The structure of an electrical system according to the modification of the fifth embodiment can be the same as the structure of the electrical system according to the fifth embodiment. A calculation section 600 further receives a second signal (14) from the second light-receiving section 21B, and calculates the aberration of the eye 100 under measurement according to the second signal (14).

Figure 23:
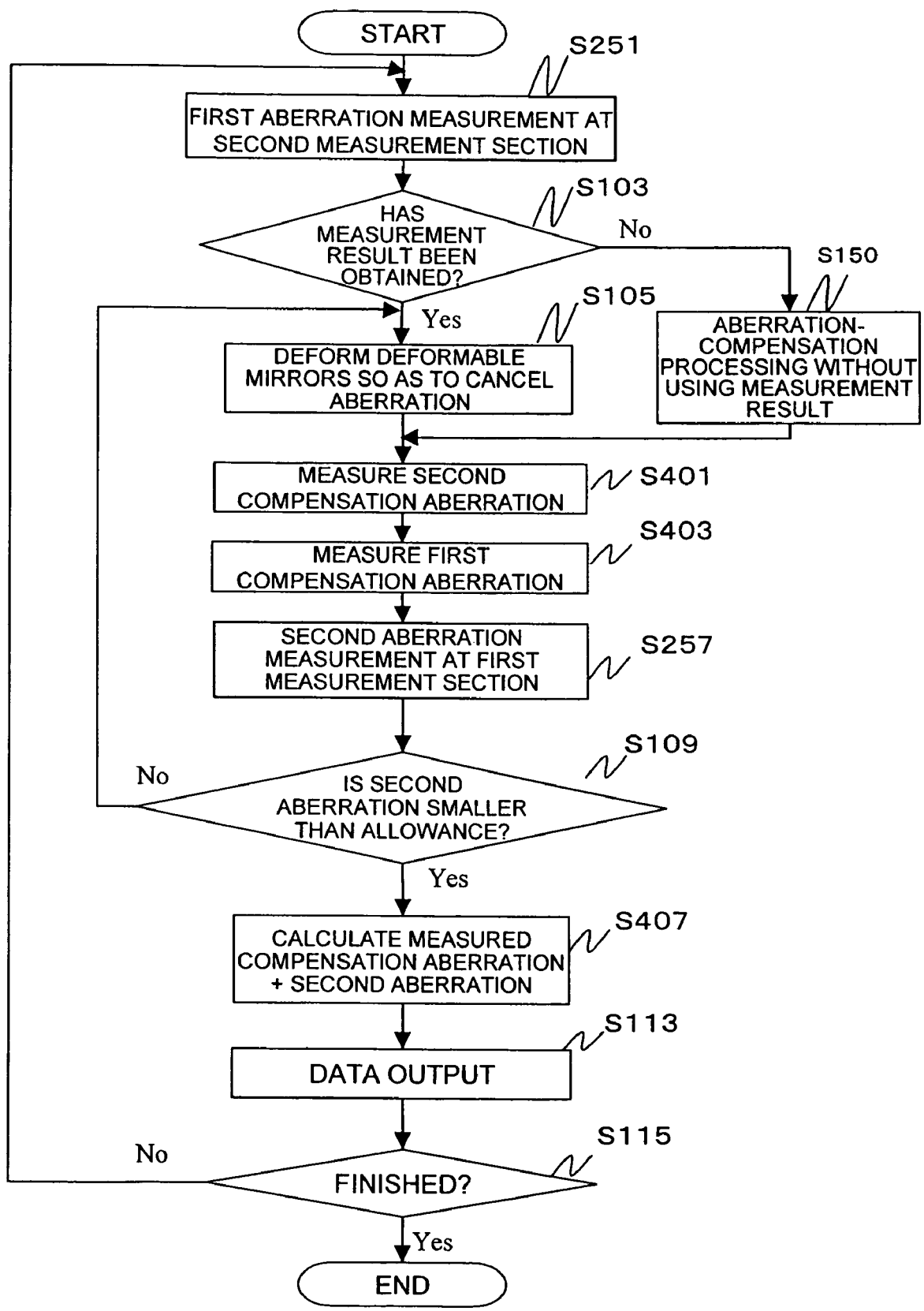
FIG. 23 is a flowchart of aberration measurement which uses the optical system according to the modification of the fifth embodiment.

FIG. 23 is a flowchart of aberration measurement which uses an optical system according to the modification of the fifth embodiment. The flowchart shown in FIG. 23 indicates a case, for example, in which the process of the first aberration measurement shown in the flowchart of FIG. 14 is performed according to the output of the second measurement section 25B. Since the process of each step is the same as that shown in FIG. 8 and FIG. 14, the same symbol is assigned and a detailed description thereof is omitted. The processes of steps S401 and S403 may be executed in the reverse order or in parallel. The processes of steps S401 and S403, and the process of step S257 may be executed in the reverse order or in parallel. Further, as shown in the modification shown in FIG. 6, aberration calculation for the eye 100 under measurement and the output of the calculation result may be performed each time aberration measurement is performed after compensation.

(First Modification of the Sixth Embodiment)

FIG. 24 is a view showing the structures of optical systems according to a first modification of the sixth embodiment. An optical system shown in FIG. 24(a) is obtained by further adding a second measurement section 25B for measurement having a short focal length, a low sensitivity, and/or a high density, and a beam splitter 23 to the optical system according to the sixth embodiment, shown in FIG. 15. The second measurement section 25B needs to be for measurement with one of a short focal length, a low sensitivity, and a high density, but is preferably for measurement with a short focal length and a low sensitivity. The second measurement section 25B includes a second light-receiving optical system 20B and a second light-receiving section 21B. An optical system shown in FIG. 24(b) is arranged such that a light beam reflected by the second compensation optical section 60B shown in FIG. 24(a) is also incident on the second measurement section 25B. A first conversion member 22A used in the optical systems shown in FIG. 24(a) and FIG. 24(b) is a wavefront conversion member having a lens section with a long focal length and/or a high sensitivity. The other portions are the same as those shown in FIG. 15. FIG. 24(a) and FIG. 24(b) show only portions corresponding to that enclosed by the dotted line in FIG. 1, but the other portions are the same as those shown in FIG. 1.

The structure of an electrical system according to the first modification of the sixth embodiment can be the same as the structure of the electrical system according to the sixth embodiment. A calculation section 600 further receives a second signal (14) from the second light-receiving section 21B, and calculates the aberration of the eye 100 under measurement according to the second signal (14).

Figure 25:
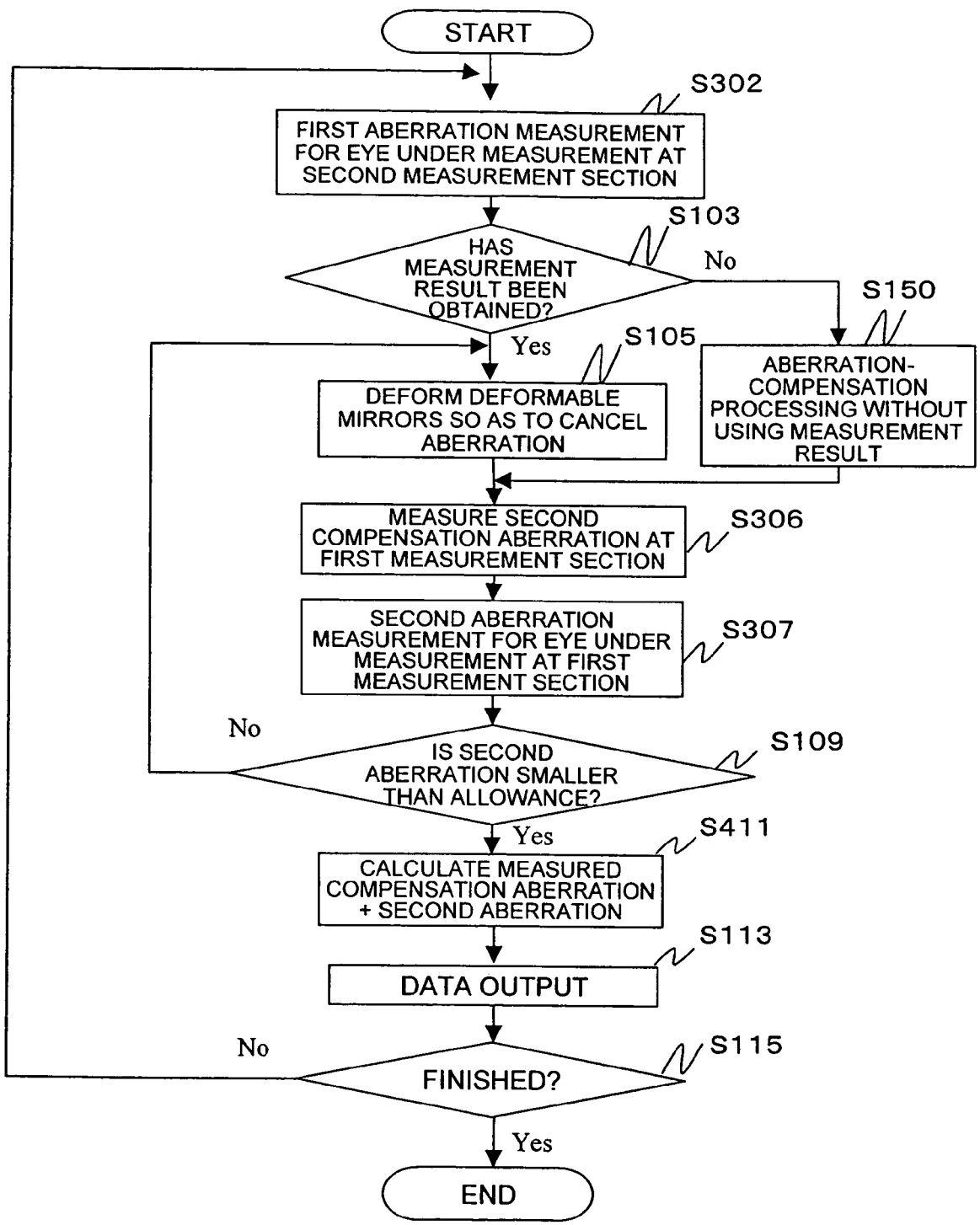
FIG. 25 is a flowchart of aberration measurement which uses the optical system according to the first modification of the sixth embodiment.

FIG. 25 is a flowchart of aberration measurement which uses an optical system according to the modification of the sixth embodiment. The flowchart shown in FIG. 25 indicates a case, for example, in which the process of the first aberration measurement shown in the flowchart of FIG. 16 is performed according to the output of the second measurement section 25B.

First, a light beam reflected from the eye 100 under measurement is incident on the second measurement section 25B, and the calculation section 600 obtains the aberration of the eye 100 under measurement according to the output of the second measurement section 25B (S302). The calculation section 600, for example, turns on a first light-source section 11 and turns off a third light-source section 16 to make a light beam reflected from the eye 100 under measurement incident on the second light-receiving optical system 20A, and receives the second signal from the second light-receiving section 21A. Then, the calculation section 600 obtains a rough aberration of the eye 100 under measurement according to the received second signal. Aberration calculation is the same as that described above. The calculation section 600 may further obtain the cornea shape, cornea aberration, and others according to a signal sent from an eye-front-part-image light-receiving section 41 of an eye-front-part observation section 40. The calculation section 600 stores these calculation results in a memory 800. Since the process of each of subsequent steps is the same as that shown in FIG. 16, the same symbol is assigned and a detailed description thereof is omitted. The processes of steps S306 and S307 may be executed in the reverse order. Further, as shown in the modification shown in FIG. 6, aberration calculation for the eye 100 under measurement and the output of the calculation result may be performed each time aberration measurement is performed after compensation. When the optical system shown in FIG. 24(b) is used, the process of step S306 may be performed according to the output of the second measurement section 25B.

(Modification of the Seventh Embodiment)

Figure 26:
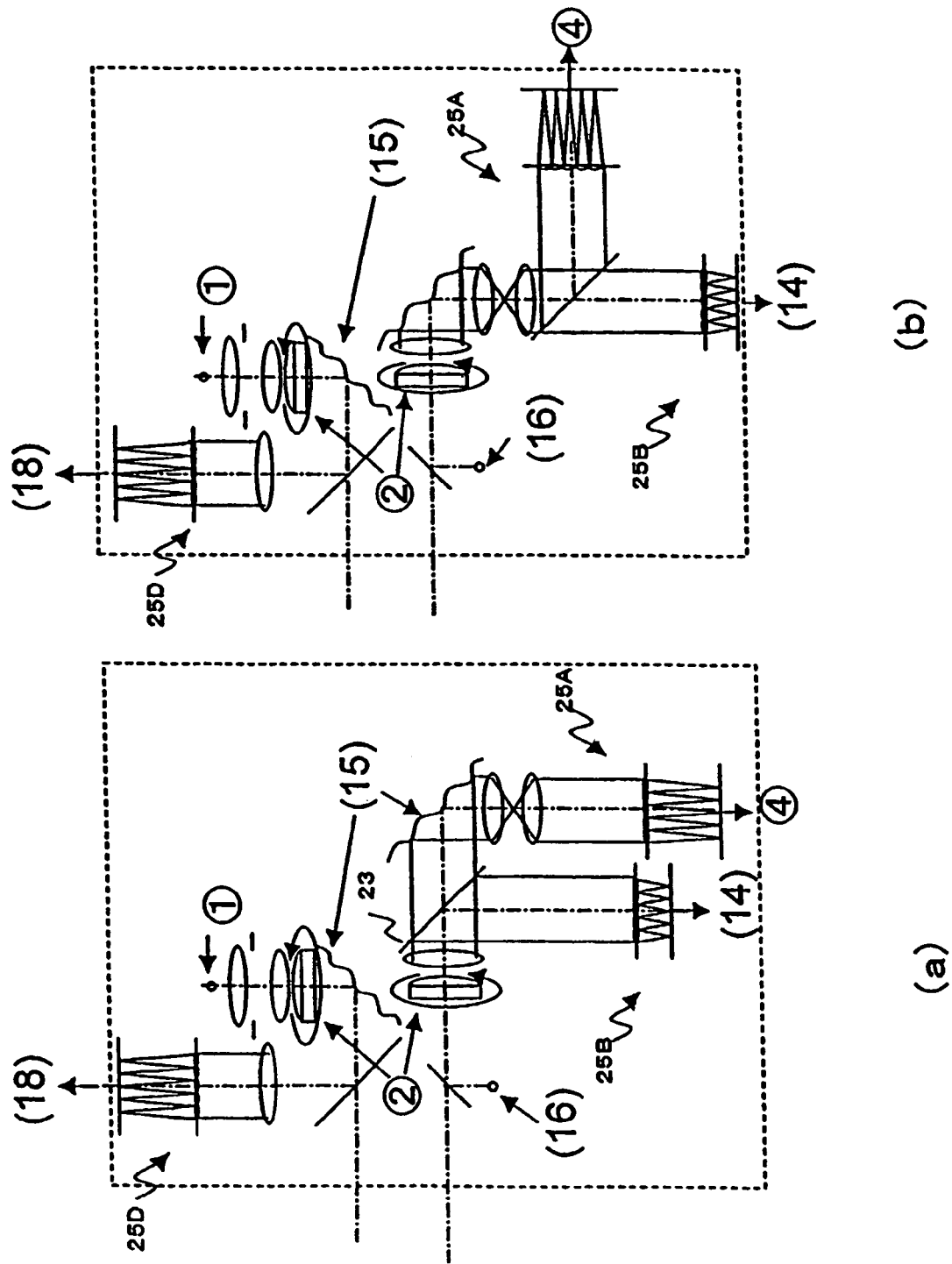
FIG. 26 is a view showing the structure of an optical system according to a modification of the seventh embodiment.

FIG. 26 is a view showing the structures of optical systems according to a modification of the seventh embodiment. An optical system shown in FIG. 26(a) is obtained by further adding a second measurement section 25B for measurement having a short focal length, a low sensitivity, and/or a high density, and a beam splitter 23 to the optical system according to the seventh embodiment, shown in FIG. 17. It is more preferred that the second measurement section 25B have a short focal length and a low sensitivity. The second measurement section 25B includes a second light-receiving optical system 20B and a second light-receiving section 21B. An optical system shown in FIG. 26(b) is arranged such that a light beam reflected by the second compensation optical section 60B shown in FIG. 26(a) is also incident on the second measurement section 25B. A first conversion member 22A used in the optical systems shown in FIG. 26(a) and FIG. 26(b) is a wavefront conversion member having a lens section with a long focal length or a high sensitivity. It is preferred that the first conversion member 22A have a lens section with a long focal length and a high sensitivity. The other portions are the same as those shown in FIG. 17. FIG. 26(a) and FIG. 26(b) show only portions corresponding to that enclosed by the dotted line in FIG. 1, but the other portions are the same as those shown in FIG. 1.

The structure of an electrical system according to the modification of the seventh embodiment can be the same as the structure of the electrical system according to the seventh embodiment. A calculation section 600 further receives a second signal (14) from the second light-receiving section 21B, and calculates the aberration of the eye 100 under measurement according to the second signal (14).

Figure 27:
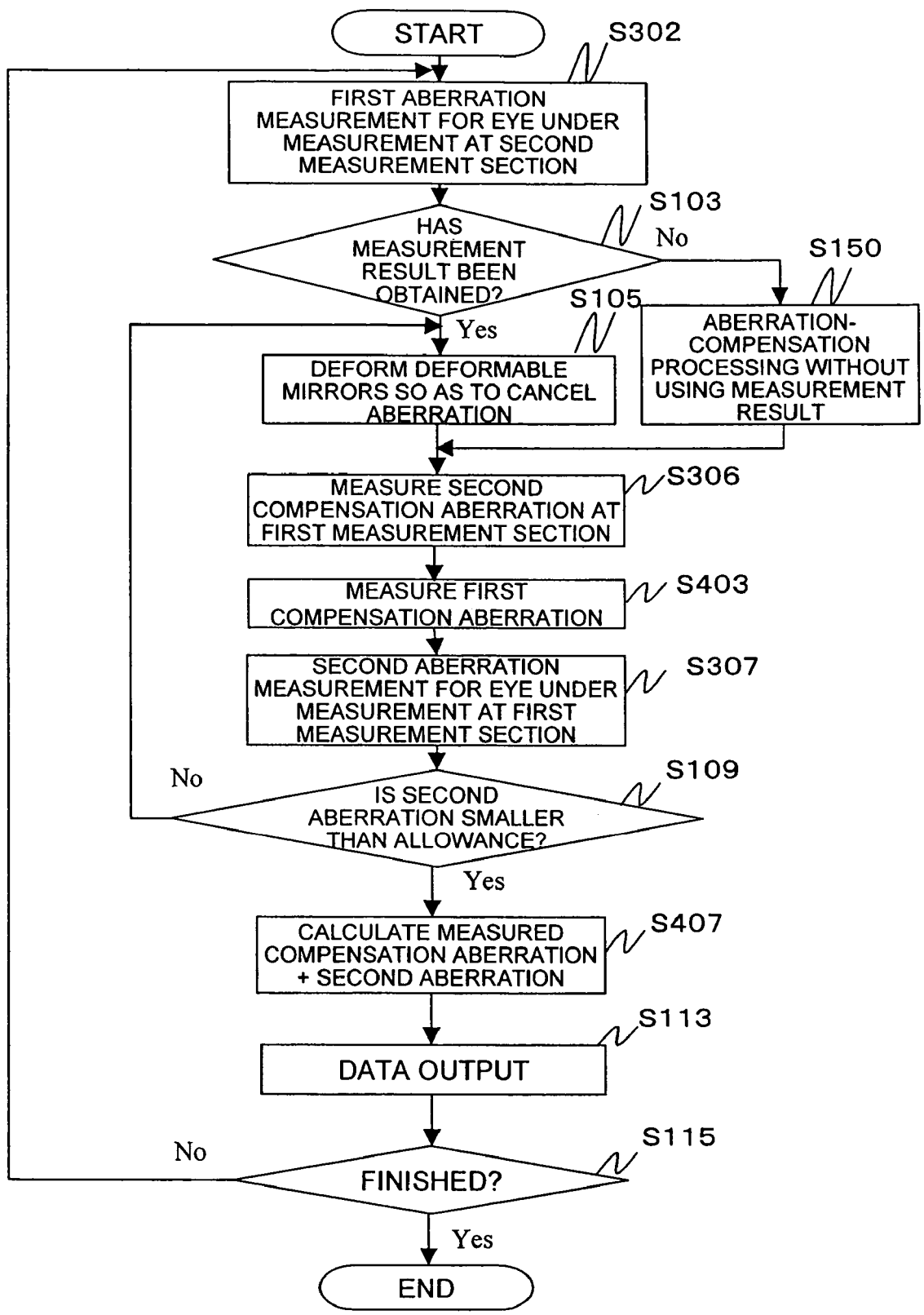
FIG. 27 is a flowchart of aberration measurement which uses the optical system according to the modification of the seventh embodiment.

FIG. 27 is a flowchart of aberration measurement which uses an optical system according to the modification of the seventh embodiment. The flowchart shown in FIG. 27 indicates a case, for example, in which the process of the first aberration measurement shown in the flowchart of FIG. 18 is performed according to the output of the second measurement section 25B. Since the process of each step is the same as that shown in FIG. 18 and FIG. 25, the same symbol is assigned and a detailed description thereof is omitted. The processes of steps S306 and S403 may be executed in the reverse order. The processes of steps S306 and S403, and the process of step S307 may be executed in the reverse order. Further, as shown in the modification shown in FIG. 6, aberration calculation for the eye 100 under measurement and the output of the calculation result may be performed each time aberration measurement is performed after compensation.

(Modification of the Eighth Embodiment)

Figure 28:
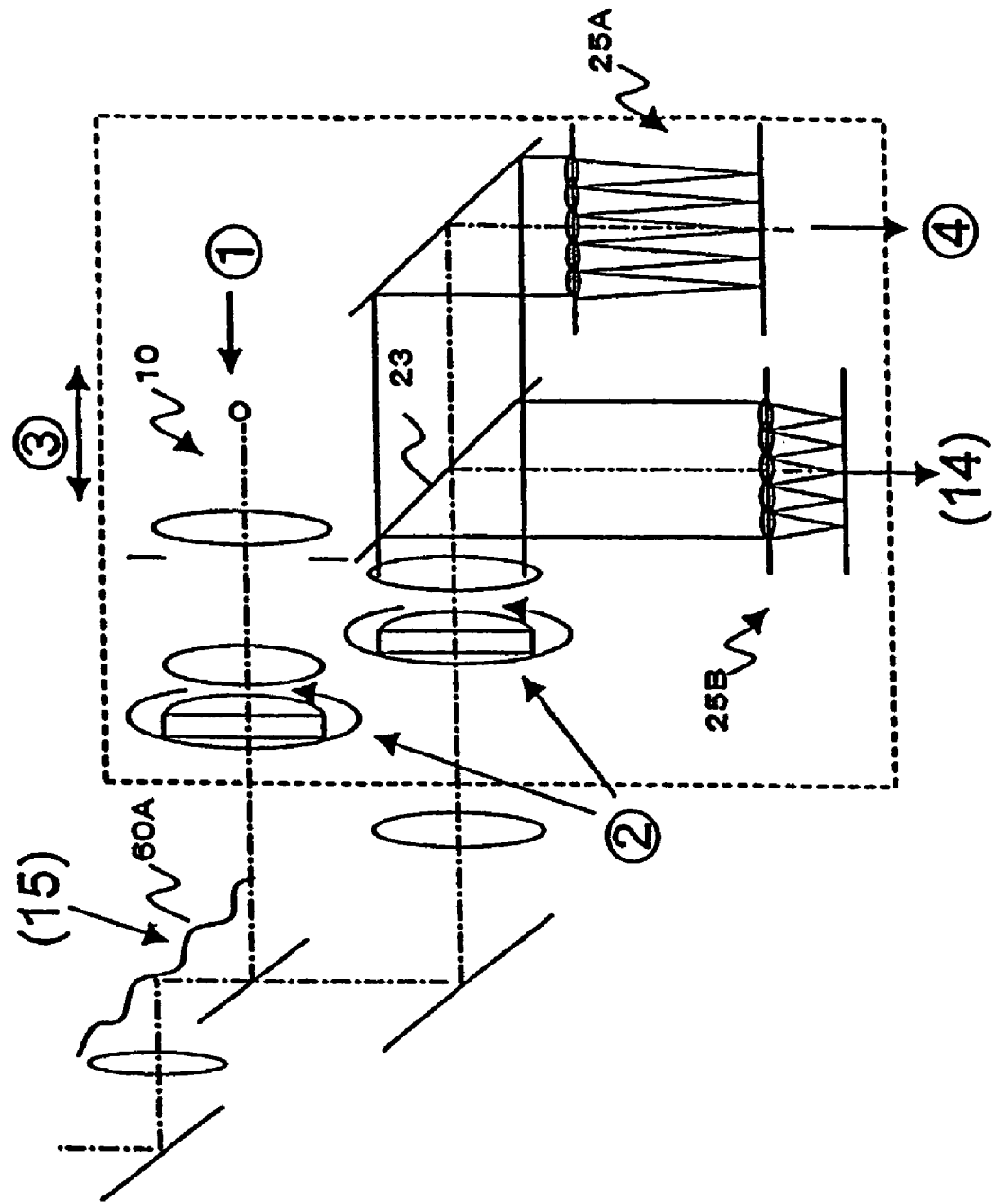
FIG. 28 is a view showing the structure of an optical system according to a modification of the eighth embodiment.

FIG. 28 is a view showing the structure of an optical system according to a modification of the eighth embodiment. The optical system shown in FIG. 28 is obtained by further adding a second measurement section 25B for measurement having a short focal length, a low sensitivity, and/or a high density, and a beam splitter 23 to the optical system according to the eighth embodiment, shown in FIG. 19. The second measurement section 25B needs to be for measurement with one of a short focal length, a low sensitivity, and a high density, but is preferably for measurement with a short focal length and a low sensitivity. The second measurement section 25B includes a second light-receiving optical system 20B and a second light-receiving section 21B. A first conversion member 22A used in the optical system shown in FIG. 28 is a wavefront conversion member having a lens section with a long focal length and/or a high sensitivity. The other portions are the same as those shown in FIG. 19. FIG. 28 shows only a portion corresponding to that enclosed by the dotted line in FIG. 1, but the other portions are the same as those shown in FIG. 1.

The structure of an electrical system according to the modification of the eighth embodiment can be the same as the structure of the electrical system according to the eighth embodiment. A calculation section 600 further receives a second signal (14) from the second light-receiving section 21B, and calculates the aberration of the eye 100 under measurement according to the second signal (14). A flowchart of aberration measurement which uses the optical system according to the modification of the eighth embodiment can be the flowchart shown in FIG. 8.

The optical system according to each embodiment can be modified such that the first compensation optical section 60A and the second compensation optical system 60B are made to one system. The modification thereof will be described below.

(Second Modification of the Fourth Embodiment)

Figure 29:
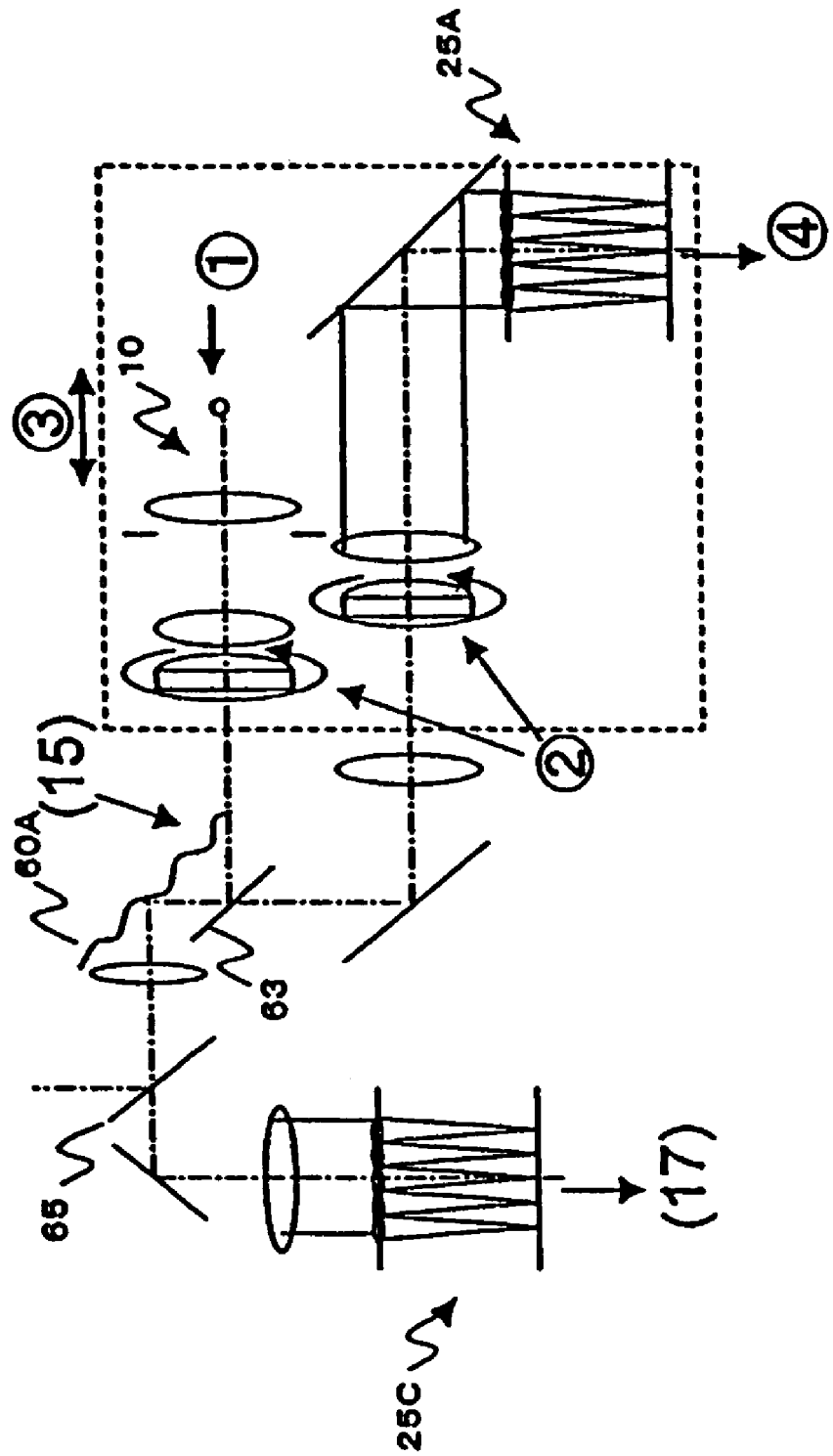
FIG. 29 is a view showing the structure of an optical system according to a second modification of the fourth embodiment.

FIG. 29 is a view showing the structure of an optical system according to a second modification of the fourth embodiment. The optical system shown in FIG. 29 indicates a case in which the first compensation optical section 60A and the second compensation optical system 60B in the optical system according to the fourth embodiment, shown in FIG. 10, are made to one system. The first compensation optical section 60A is inserted into the optical path common to light incident on the eye 100 under measurement and light reflected from the eye 100 under measurement. A third light-receiving section 21C receives a light beam emitted from a first light-source section 11, reflected by the first compensation optical section 60A, and divided by a beam splitter 65. In the optical system shown in FIG. 29, a part of a light beam emitted from the first light-source section 11 is used to measure compensation aberration, instead of a light beam emitted from a third light-source section 16, as an example case. The third light-source section 16 for measuring compensation aberration may be appropriately disposed in the same way as in the fourth embodiment.

A calculation section 600 measures first compensation aberration according to the output of a third measurement section 25C. The beam splitter 65 divides a light beam emitted from the first light-source section 11 into light toward the eye 100 under measurement and light toward the third measurement section 25C. The beam splitter 65 also reflects a light beam reflected and returned from the eye 100 under measurement. The beam splitter 65 can, for example, be a beam splitter which reflects and transmits light at a certain ratio (for example, 9:1). The beam splitter may be a half mirror. The other portions are the same as in FIG. 10. FIG. 29 shows only a part of the optical system, but the other portions are the same as in FIG. 19. When the optical system according to the fifth embodiment is modified such that the first compensation optical section 60A and the second compensation optical system 60B are made to one system, the same optical system as shown in FIG. 29 is obtained.

The structure of an electrical system according to the second modification of the fourth embodiment can be the same as the structure of the electrical system according to the fourth embodiment. A flowchart of aberration measurement which uses the optical system according to the second modification of the fourth embodiment can be the flowcharts shown in FIG. 11 and FIG. 12.

(Third Modification of the Fourth Embodiment)

Figure 30:
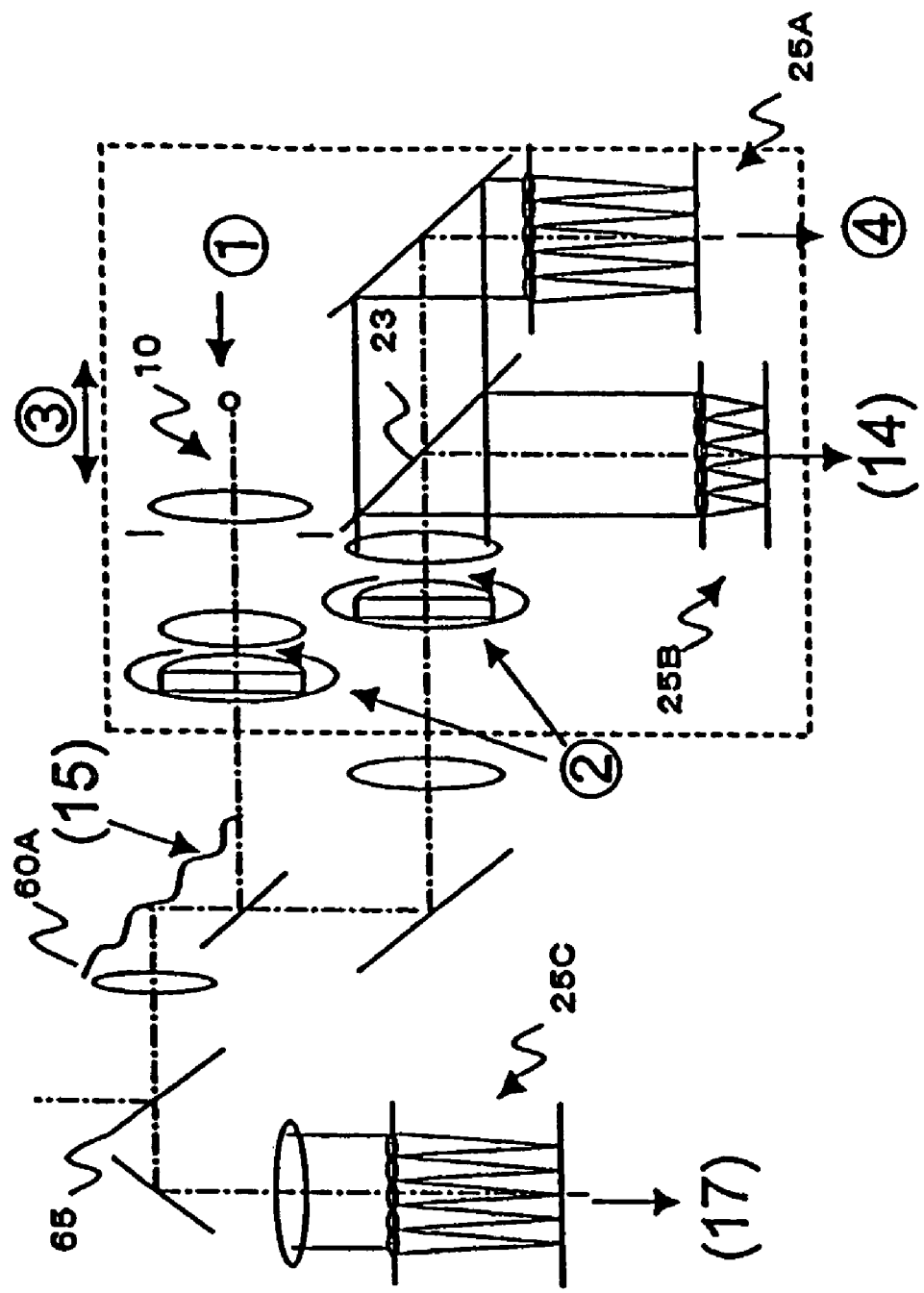
FIG. 30 is a view showing the structure of an optical system according to a third modification of the fourth embodiment.

FIG. 30 is a view showing the structure of an optical system according to a third modification of the fourth embodiment. The optical system shown in FIG. 30 is obtained by further adding a second measurement section 25B for measurement having a short focal length, and/or a low sensitivity, and/or a high density, and a beam splitter 23 to the optical system according to the second modification of the fourth embodiment, shown in FIG. 29. The structure of each portion is the same as in FIG. 28 and FIG. 29. FIG. 30 shows only a part of the optical system, but the other portions are the same as in FIG. 19.

The structure of an electrical system according to the third modification of the fourth embodiment can be the same as the structure of the electrical system according to the second embodiment. A flowchart of aberration measurement which uses the optical system according to the third modification of the fourth embodiment can be the flowchart shown in FIG. 21.

(Second Modification of the Sixth Embodiment)

Figure 31:
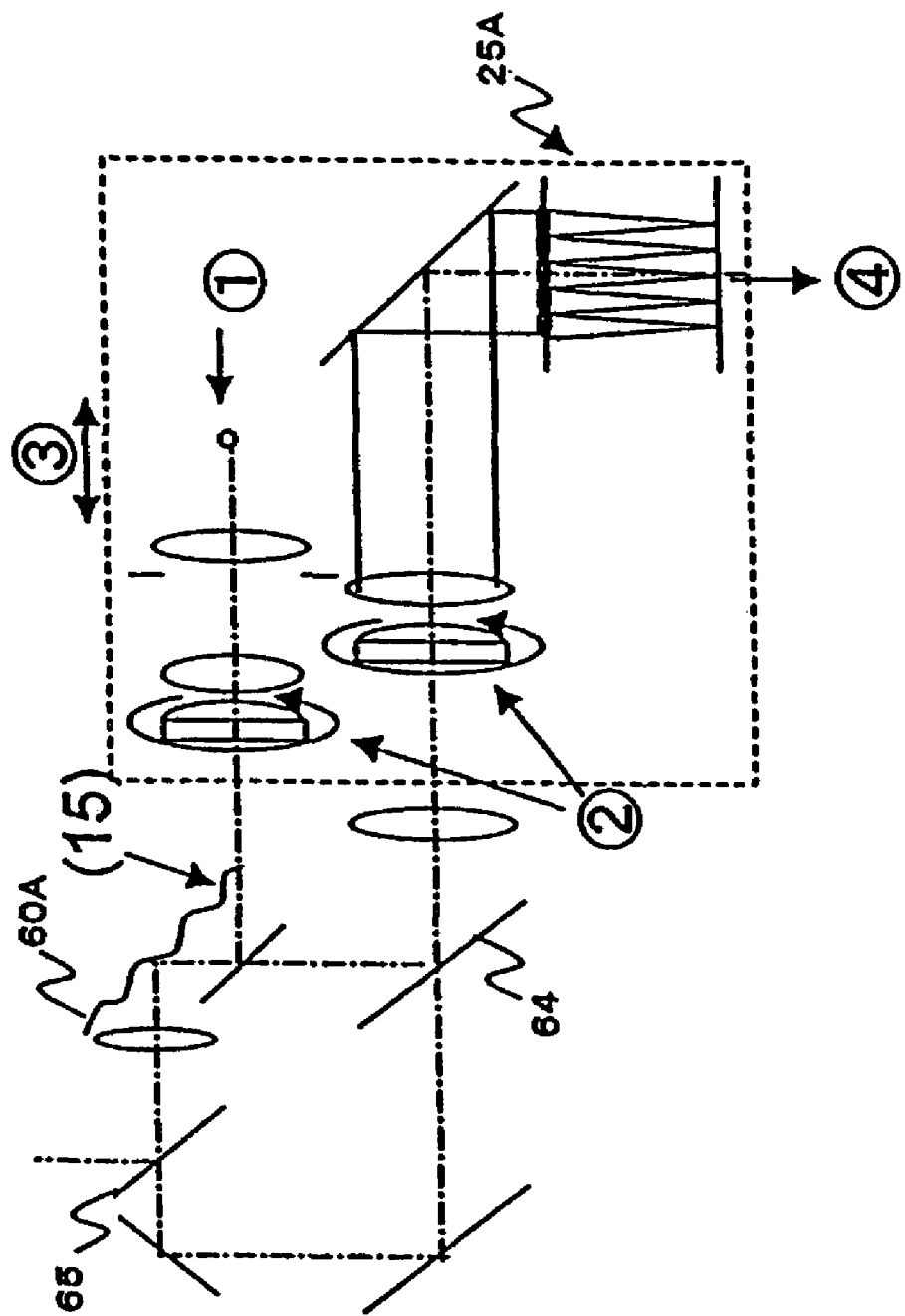
FIG. 31 is a view showing the structure of an optical system according to a second modification of the sixth embodiment.

FIG. 31 is a view showing the structure of an optical system according to a second modification of the sixth embodiment. The optical system shown in FIG. 31 indicates a case in which the first compensation optical section 60A and the second compensation optical system 60B in the optical system according to the sixth embodiment, shown in FIG. 15, are made to one system. The first compensation optical section 60A is inserted into the optical path common to light incident on the eye 100 under measurement and light reflected from the eye 100 under measurement. A part of a light beam emitted from the first light-source section 11 is incident on the eye 100 under measurement through the first compensation optical section 60A and a beam splitter 65. Another part of a light beam emitted from the first light-source section 11 is led to a first measurement section 25A through the first compensation optical section 60A and a beam splitter 65. A light beam reflected from the eye 100 under measurement passes through the beam splitter 65 and the first compensation optical section 60A, is reflected by a beam splitter 64, and is led to the first measurement section 25A. The beam splitter 64 is, for example, a polarization beam splitter which transmits a light beam emitted from the first light-source section 11 and reflects a light beam reflected by the eye 100 under measurement. By switching between the light beam reflected from the eye 100 under measurement and a light beam for compensation aberration measurement both of which are incident on the first measurement section 25A, measurement is possible with one measurement section. For example, a chopper can be provided in the optical path before the beam splitter 64 and controlled to switch the light beam. Appropriate light-beam switching means other than a chopper may be used. The other portions are the same as in FIG. 15. FIG. 31 shows only a part of the optical system, but the other portions are the same as in FIG. 19. When the optical system according to the seventh embodiment is modified such that the first compensation optical section 60A and the second compensation optical section 60B are made to be one system, the same optical system as that shown in FIG. 31 is obtained.

The structure of an electrical system according to the second modification of the sixth embodiment can be the same as the structure of the electrical system according to the sixth embodiment. A flowchart of aberration measurement which uses the optical system according to the second modification of the sixth embodiment can be the flowchart shown in FIG. 16. The light beam reflected from the eye 100 under measurement and the light beam for compensation aberration measurement, both of which are incident on the first measurement section 25A, are switched by controlling a device provided in the optical path, such as a chopper, instead of turning on and off the light source. When a light-source section for compensation aberration measurement is provided, and this light-source section and the first light-source section 11 are turned on and off, the light beam incident on the first measurement section 25A is switched.

(Third Modification of the Sixth Embodiment)

Figure 32:
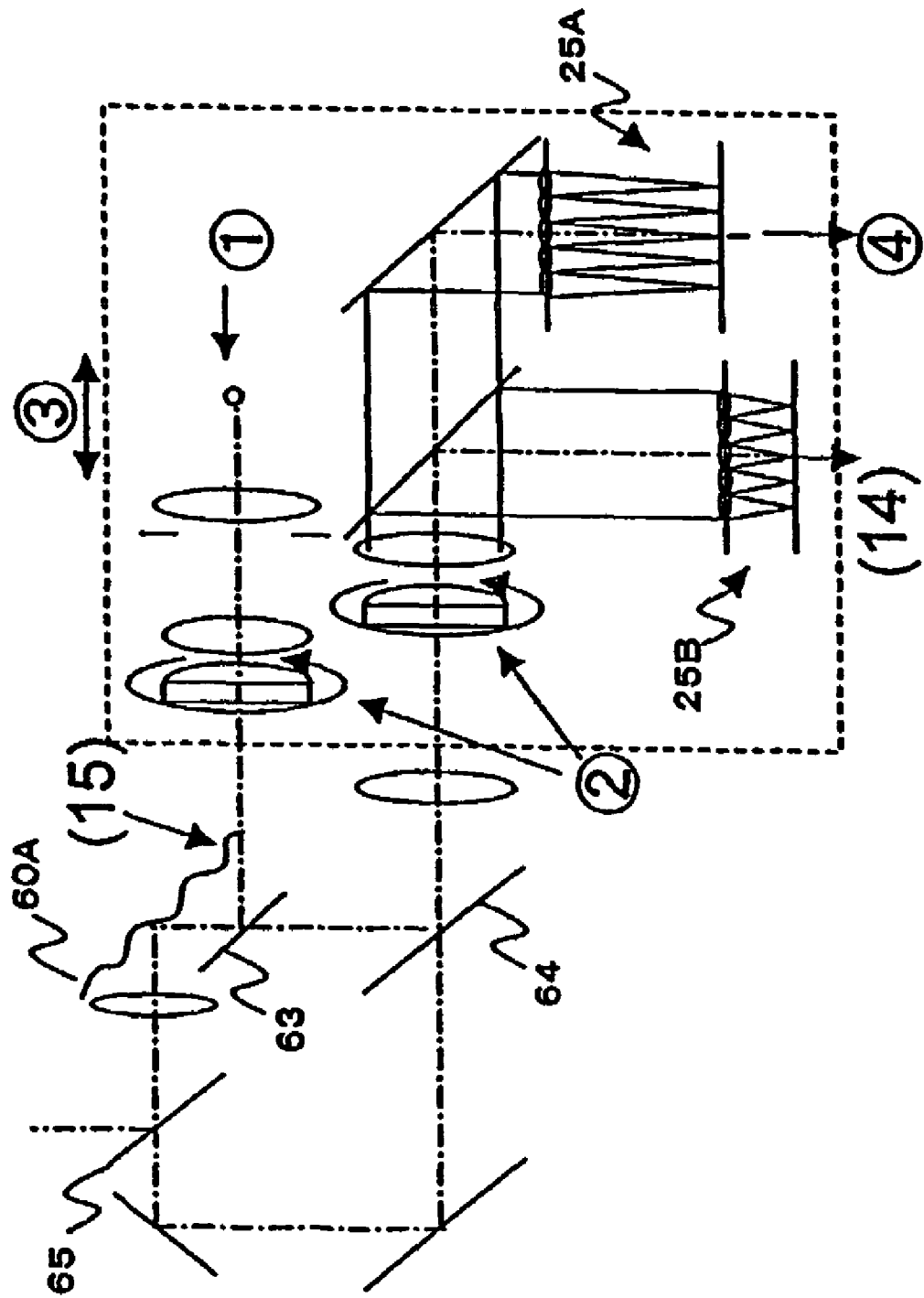
FIG. 32 is a view showing the structure of an optical system according to a third modification of the sixth embodiment.

FIG. 32 is a view showing the structure of an optical system according to a third modification of the sixth embodiment. The optical system shown in FIG. 32 is obtained by further adding a second measurement section 25B for measurement having a short focal length, a low sensitivity, and/or a high density, and a beam splitter 23 to the optical system according to the second modification of the sixth embodiment, shown in FIG. 19. The second measurement section 25B needs to be for measurement with one of a short focal length, a low sensitivity, and a high density, but is preferably for measurement with a short focal length and a low sensitivity. The structure of each section is the same as in FIG. 28 and FIG. 31. FIG. 32 shows only a part of the optical system, but the other portions are the same as in FIG. 19.

The structure of an electrical system according to the third modification of the sixth embodiment can be the same as the structure of the electrical system according to the fourth embodiment. A flowchart of aberration measurement which uses the optical system according to the third modification of the sixth embodiment can be the flowchart shown in FIG. 25.

(Optical System According to a Modification of the First Embodiment)

Figure 35:
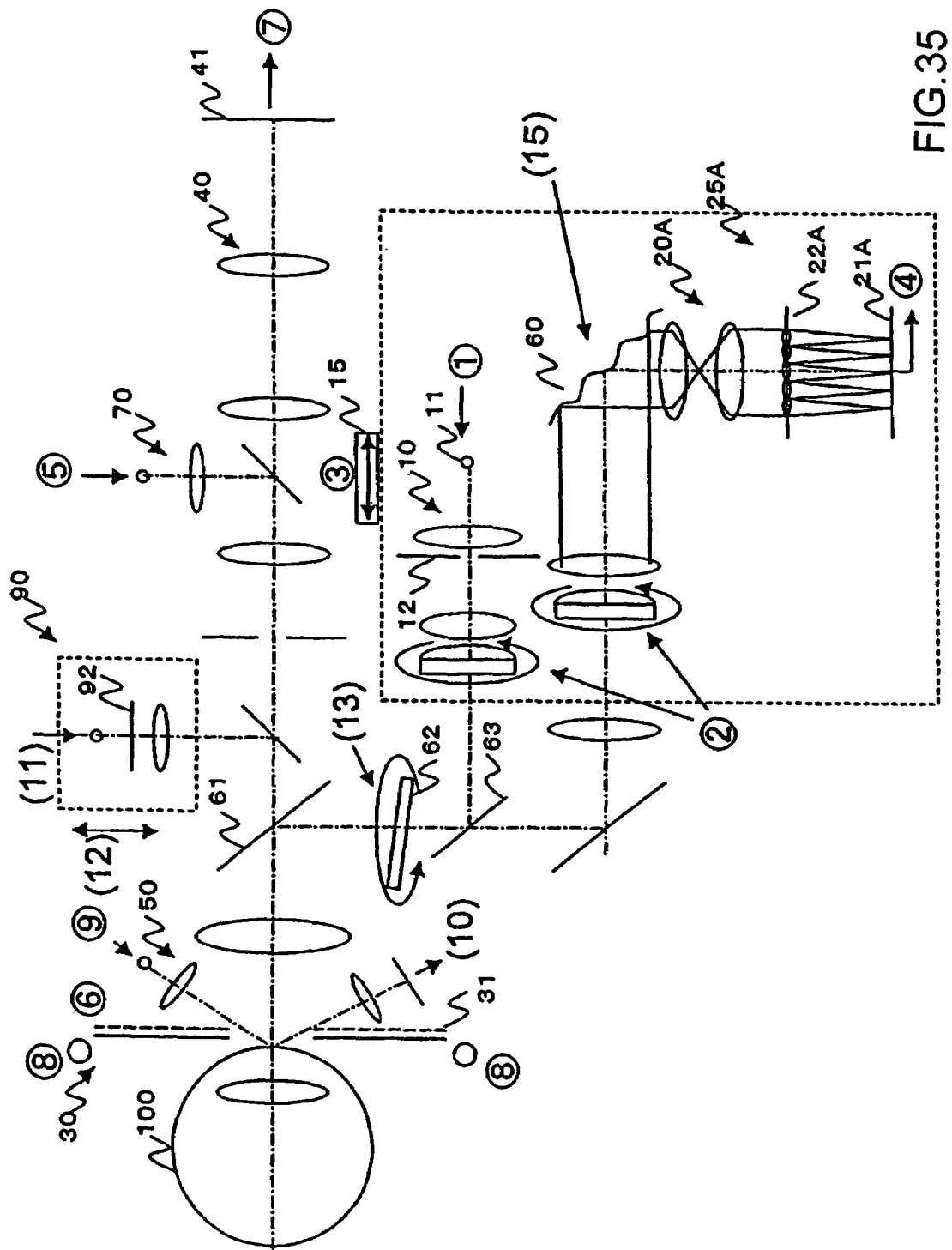
FIG. 35 is a view showing the structure of an optical system of an eye-characteristics measurement apparatus according to a first modification of the first embodiment.

FIG. 35 is a view showing the structure of an optical system of an eye-characteristics measurement apparatus according to a modification of the first embodiment.

An eye-characteristics measurement apparatus includes a first illumination optical system 10, a first light-source section 11, a first measurement section 25A, an eye-front-part illumination section 30, an eye-front-part observation section 40, a first adjustment optical section 50, a compensation optical section 60, a second adjustment optical section 70, and an eyesight-target optical section 90. The first measurement section 25A has a first light-receiving optical system 20A and a first light-receiving section 21A. In an eye 100 under measurement, a retina (eyeground) and a cornea (eye-front part) are shown in the figure. The structure of each section is the same as that described above. The compensation optical section 60 is the same as the second compensation optical section 60B, described above.

When a diaphragm 12 is made to be decentering, the position of incidence of light emitted from the first light-source section 11 and incident on the eye 100 under measurement is changed in a direction perpendicular to the optical axis to prevent the vertex reflection of a lens and the retina to suppress noise. The diaphragm 12 is made such that its diameter is smaller than the effective area of a Hartmann plate 22A and the aberration of the eye affects only at the light-receiving side, that is, so-called single-path aberration measurement is implemented.

After incident light emitted from the first light-source section 11 advances the same optical path as measurement light diffuse-reflected from the eyeground, the incident light advances in the same way as the measurement light diffuse-reflected from the eyeground at a zone close to the axis. In single-path measurement, they have different diameters. The diameter of the incident light beam is much smaller than that of the measurement light. More specifically, for example, the diameter of the incident light beam is about 1 mm at the pupil position of the eye under measurement, and the diameter of the measurement light beam is about 7 mm in some cases. When the optical system is appropriately arranged, double-path measurement can be implemented.

Figure 38:
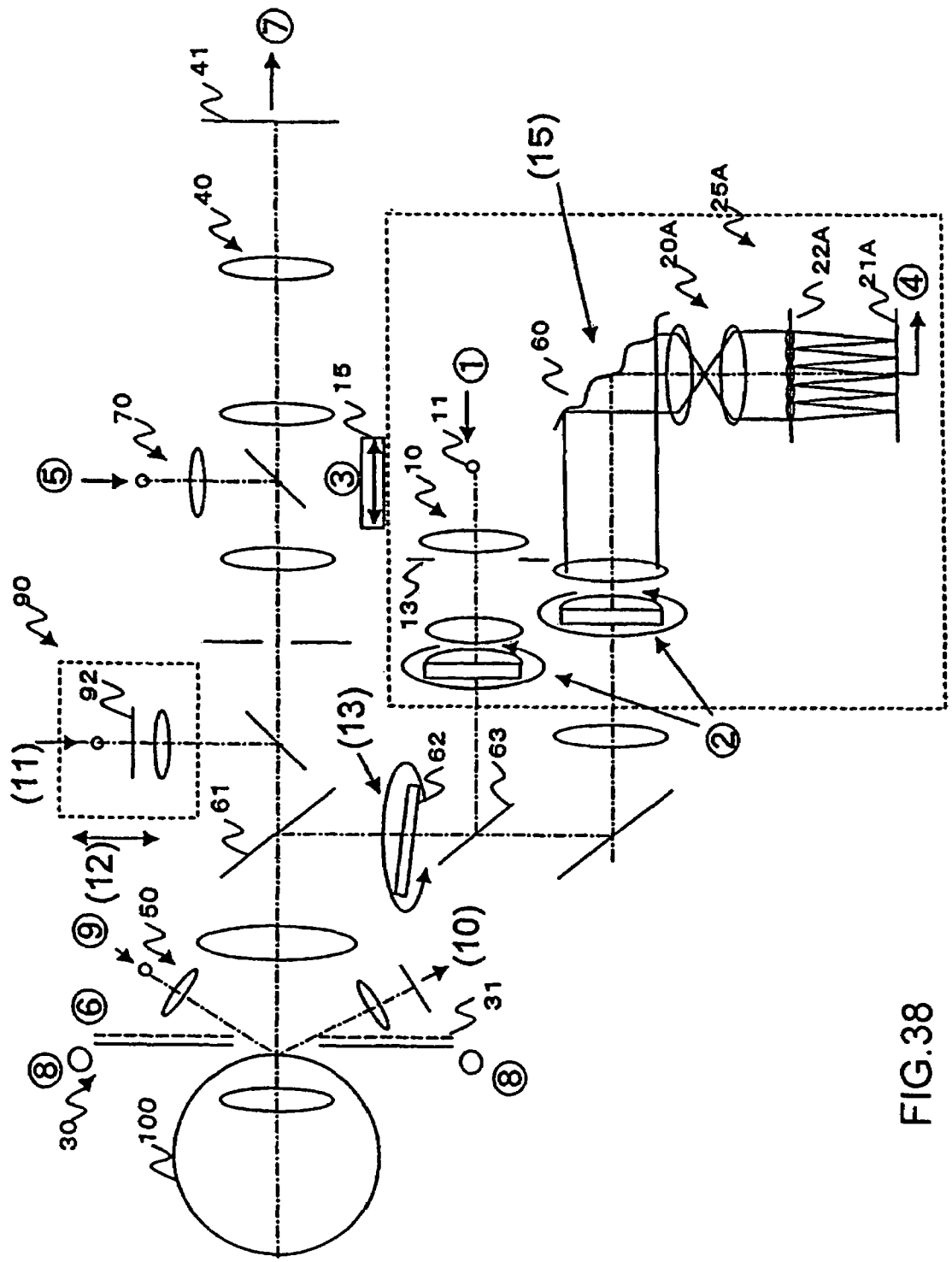
FIG. 38 is a view showing the structure of an optical system for double-path measurement according to a modification of the first embodiment.

FIG. 38 is a view showing the structure of an optical system for double-path measurement according to a modification of the first embodiment. For example, a diaphragm 13 for double-path measurement in a first illumination optical system 10 can make an incident light beam emitted from the first illumination optical system 10 wide. The structures of the other portions are the same as in FIG. 35.

The structure of an electrical system according to the modification of the first embodiment can be the same as the structure of the electrical system according to the first embodiment. A flowchart of aberration measurement which uses the optical system according to the modification of the first embodiment can, for example, be the flowchart shown in FIG. 3.

(Optical System According to a Modification of the Second Embodiment)

Figure 36:
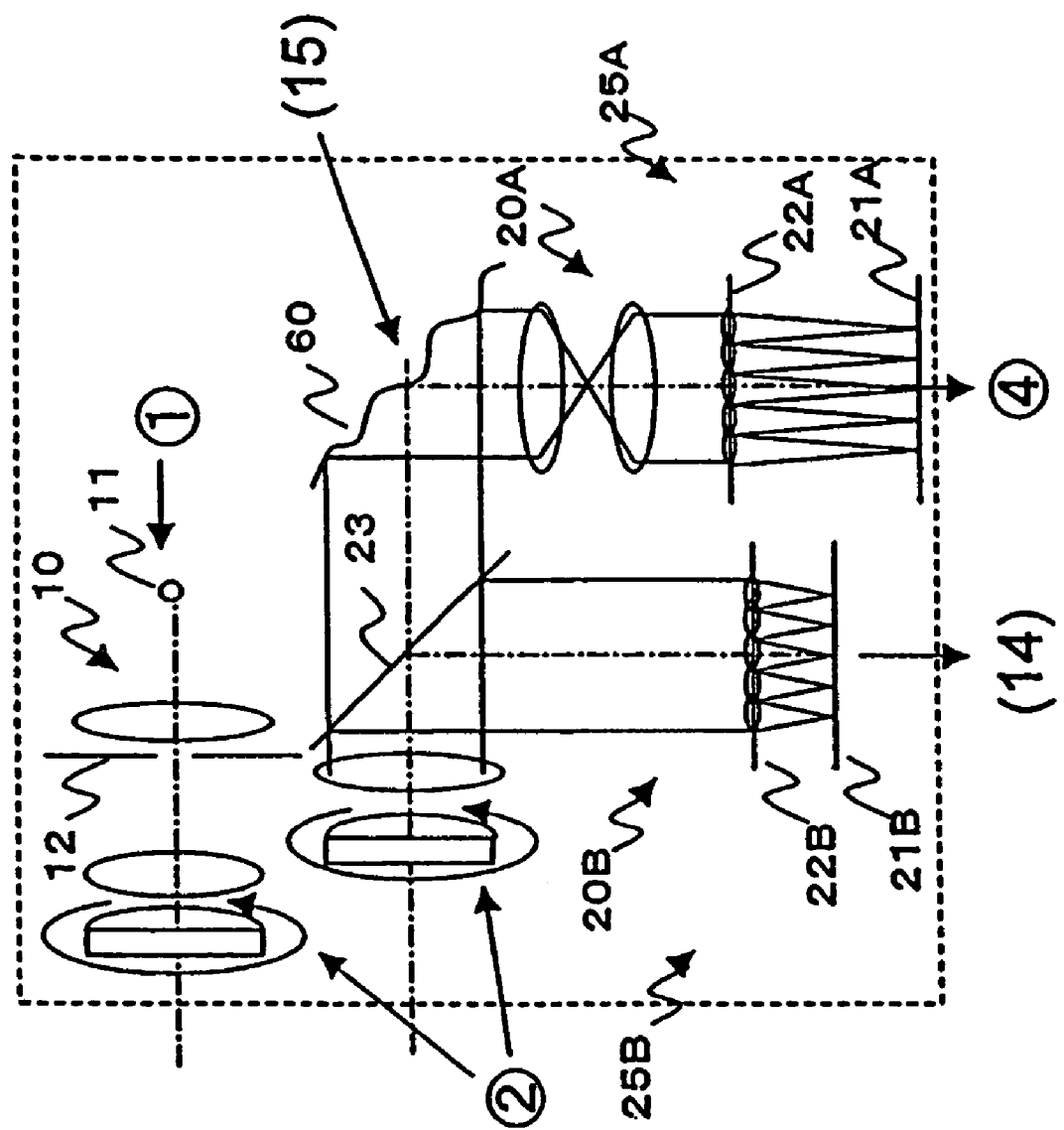
FIG. 36 is a view showing the structure of an optical system of an eye-characteristics measurement apparatus according to a modification of the second embodiment.

FIG. 36 is a view showing the structure of an optical system of an eye-characteristics measurement apparatus according to a modification of the second embodiment. FIG. 36 shows only a portion corresponding to a portion enclosed in a dotted line in FIG. 35, but the other portions are the same as in FIG. 35. The eye-characteristics measurement apparatus shown in FIG. 36 further includes a second measurement section 25B having a short focal length, a low sensitivity, and/or a high density, and a half mirror 23.

The structure of an electrical system according to the modification of the second embodiment can be the same as the structure of the electrical system according to the second embodiment. A flowchart of aberration measurement which uses the optical system according to the modification of the second embodiment can be, for example, the flowchart shown in FIG. 8.

(Optical System According to a Modification of the Third Embodiment)

Figure 37:
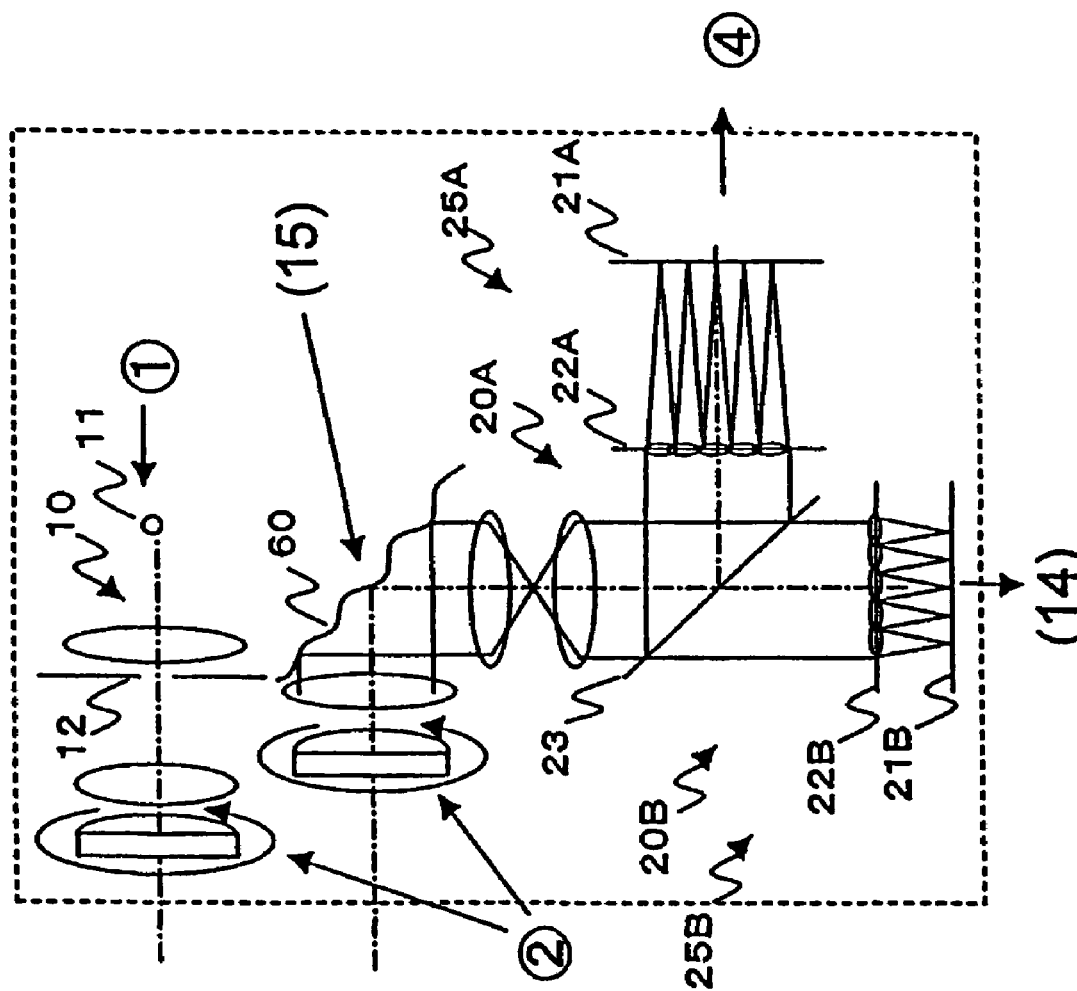
FIG. 37 is a view showing the structure of an optical system of an eye-characteristics measurement apparatus according to a modification of the third embodiment.

FIG. 37 is a view showing the structure of an optical system of an eye-characteristics measurement apparatus according to a modification of the third embodiment. FIG. 37 shows only a portion corresponding to the portion enclosed in the dotted line in FIG. 35, but the other portions are the same as in FIG. 35. In the eye-characteristics measurement apparatus shown in FIG. 37, a compensation optical section 60 is inserted in common into the first and second measurement sections 25A and 25B. A light beam reflected and returned from the retina of an eye 100 under measurement is led to the first and second measurement sections 25A and 25B through the compensation optical section 60. Since the optical beam is led to the second measurement section 25B through the compensation optical section 60, aberration obtained after compensation can be measured even in the second measurement section 25B. In addition, it is possible that the compensation optical section 60 is deformed until aberration measured at the output of the second measurement section 25B becomes equal to or smaller than an allowance specified in advance. The optical systems shown in FIG. 36 and FIG. 37 are described mainly as for single-path measurement, where a thin incident light beam is used. They can be changed for double-path measurement, if necessary.

The structure of an electrical system according to the modification of the third embodiment can be the same as the structure of the electrical system according to the third embodiment. A flowchart of aberration measurement which uses the optical system according to the modification of the third embodiment can be, for example, the flowchart shown in FIG. 8.

(Simulation of Point-Image Movement Distances)

When a light-receiving system having a short focal length, a low sensitivity, and/or a high density is used as in the second embodiment, the third embodiment, and the modifications thereof, for example, after the calculation section 600 determines the amount of compensation according to a signal sent from the second light-receiving optical system 20B having a short focal length, a low sensitivity, and/or a high density, the calculation section 600 can perform in real time simulation of aberration after the compensation and the movement distances of the point images. The calculation section 600 can predict the point images obtained from the first measurement section 25A, from the measurement result previously obtained from the second measurement section 25B. The movement distances of the point images and the Zernike coefficients have similar relations as indicated by the following expression.

$$\begin{cases} \dfrac{\partial W_e(X, Y)}{\partial X} = \dfrac{\Delta \hat{x}}{f} \\ \dfrac{\partial W_e(X, Y)}{\partial X} = \dfrac{\Delta \hat{y}}{f} \end{cases} \quad (8)$$

(f: Distance Between the Hartmann Plate and the CCD in the First Measurement Section 25A)

Aberration measured by the first measurement section 25A after the compensation can be predicted as the difference between the aberration measured by the second measurement section 25B and the aberration compensated for, although there is a measurement-precision difference. When the aberration after the compensation is predicted, the movement distances of the point images from which light is received by the first light-receiving section 20A can be predicted by using the foregoing expressions in the reverse way. The movement distances of the point images can be actually calculated by the following expressions, where $W_e$ indicates predicted aberration obtained after the compensation.

$$\begin{cases} \Delta \hat{x} = \dfrac{\partial}{\partial X} W_e(X, Y) \cdot f \\ \Delta \hat{y} = \dfrac{\partial}{\partial X} W_e(X, Y) \cdot f \end{cases} \quad (9)$$

When the compensation optical section 60 is deformed such that the aberration measured by the second measurement section 25B is completely canceled, predicted aberration obtained after the compensation is eliminated (becomes zero). When the aberration is not completely canceled and light incident on the Hartmann plate is directed in a divergence direction or is tilted, if the point images are associated with each other by using the foregoing expression (9) as a reference, more quickly measurement and measurement which uses the first light-receiving optical system 20A having a longer focal length and/or a higher sensitivity are possible.

(Modification of the Flowchart of Aberration Measurement According to the Second and Third Embodiments)

Figure 39:
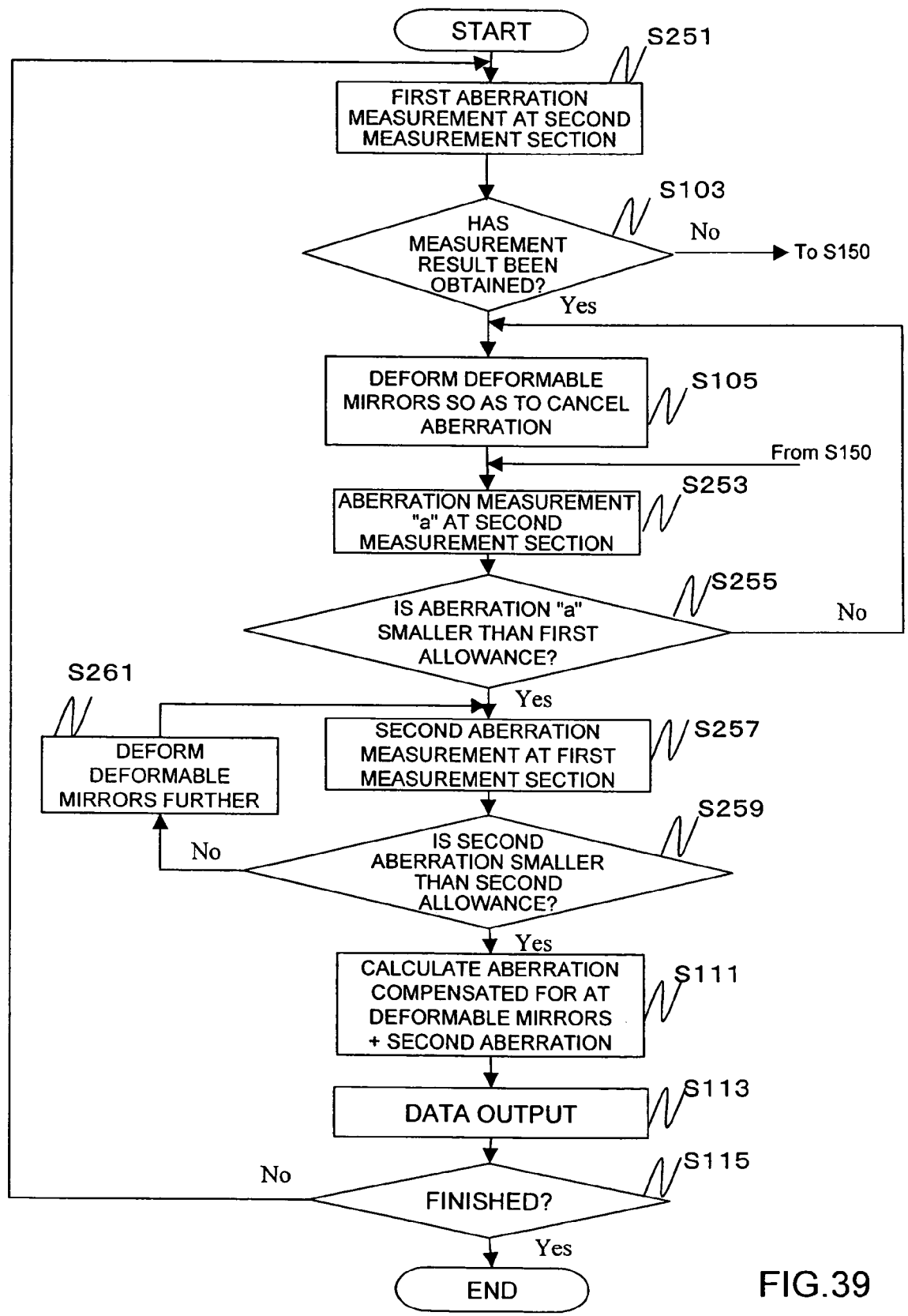
FIG. 39 is a second modification of the flowchart of aberration measurement according to the second embodiment and the third embodiment.

FIG. 39 is a modification of the flowchart of aberration measurement according to the second and third embodiments. In the present modification, the optical system shown in FIG. 37 is used, a light beam compensated for aberration is received by the second light-receiving section 21B, and compensation is performed such that aberration obtained according to a signal sent from the second light-receiving section 21B is equal to or smaller than an allowance specified in advance.

First, the calculation section 600 executes the processes of steps S251, S103, and S105. The details of the processes are the same as those described above, and a description thereof is omitted. Then, the calculation section 600 measures aberration compensated for, according to a signal at the second measurement section 25B (S253). The details of this process is the same as those in step S251, described above, and a description thereof is omitted. The calculation section 600 determines (S255) whether the aberration obtained in step S253 is equal to or smaller than a first allowance specified in advance. For example, the calculation section 600 may determine whether the RMS value of higher-order aberration is equal to or smaller than 0.1. When the aberration is larger than the first allowance, the calculation section 600 goes back to step S105, and further deforms the compensation optical section 65. When the aberration is smaller than the first allowance, the calculation section 600 proceeds to the process of step S257.

Instead of determining whether the aberration is equal to or smaller than the first allowance, the calculation section 600 may receive the first signal from the first light-receiving section 21A and determine whether measurement based on the first signal is possible. For example, the calculation section 600 can determine that measurement based on the first signal is impossible, according to one or a plurality of conditions determined in advance, such as that the number of centers of gravity of the point images based on the received first signal, obtained is less than a predetermined value (for example, less than one third the predetermined value), that each point image has a large blur (for example, has a blur 20 times or more that obtained when there is no aberration), or that the number of points which cannot be separated from an adjacent spot image and therefore cannot be detected is not less than a predetermined value. The determination condition may be any appropriate condition. When the calculation section 600 determines that measurement is impossible, the processing proceeds to the process of step S105. When the calculation section 600 determines that measurement is possible, the processing proceeds to the process of step S257.

The calculation section 600 executes the process of step S257. The details of the process are the same as those described above, and a description thereof is omitted. Then, the calculation section determines (S259) whether the aberration 2 obtained in step S257 is equal to or smaller than a second allowance determined in advance. For example, the calculation section 600 may determine whether the RMS value of higher-order aberration is equal to or smaller than 0.1. The first allowance and the second allowance can be different values. For example, with measurement sensitivity taken into account, the first allowance may be equal to or larger than the second allowance. When the aberration 2 is larger than the second allowance (S259), the calculation section 600 further deforms the compensation optical section 60 according to the aberration 2 (S261), and goes back to step S257. The details of the process for deforming the compensation optical section 60 is the same as those in step S105. When the aberration 2 is smaller than the second allowance, the calculation section 600 proceeds to the process of step S111.

Then, the calculation section 600 executes the processes of steps S111 to S115. The details of the processes are the same as those described above, and a description thereof is omitted.

(Optical System According to a Fourth Modification of the Fourth Embodiment)

Figure 40:
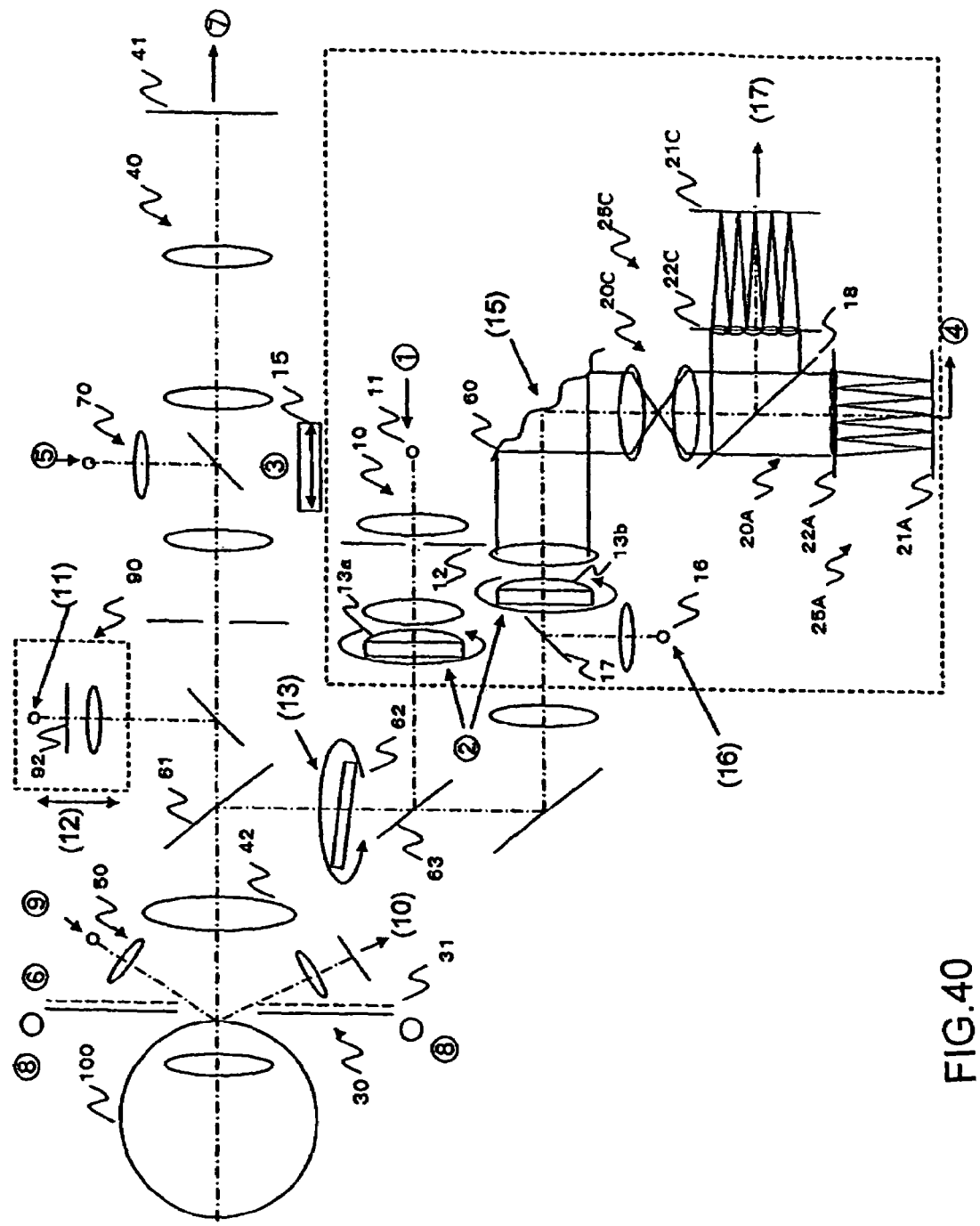
FIG. 40 is a view showing the structure of an optical system of an eye-characteristics measurement apparatus according to a fourth modification of the fourth embodiment.

FIG. 40 is a view showing the structure of an optical system of an eye-characteristics measurement apparatus according to a fourth modification of the fourth embodiment.

An eye-characteristics measurement apparatus includes a first illumination optical system 10, a first light-source section 11, a third light-source section 16, a first measurement section 25A, a third measurement section 25C, an eye-front-part illumination section 30, an eye-front-part observation section 40, a first adjustment optical section 50, a compensation optical section 60, a second adjustment optical section 70, and an eyesight-target optical section 90. The first measurement section 25A has a first light-receiving optical system 20A and a first light-receiving section 21A. The third measurement section 25C has a third light-receiving optical system 20C and a first light-receiving section 21C. In an eye 100 under measurement, a retina (eyeground) and a cornea (eye-front part) are shown in the figure. The structure of each section is the same as that described above.

When a diaphragm 12 is made to be decentering, the position of incidence of light emitted from the first light-source section 11 and incident on the eye 100 under measurement is changed in a direction perpendicular to the optical axis to prevent the vertex reflection of a lens and the retina to suppress noise. The diaphragm 12 is made such that its diameter is smaller than the effective area of a Hartmann plate 22A and the aberration of the eye affects only at the light-receiving side, that is, so-called single-path aberration measurement is implemented.

The structure of an electrical system according to the fourth modification of the fourth embodiment can be the same as the structure of the electrical system according to the fourth embodiment. A flowchart of aberration measurement which uses the optical system according to the fourth modification of the fourth embodiment can, for example, be the flowchart shown in FIG. 11. In the present modification, the second compensation aberration obtained in step S401 is compensation aberration in the compensation optical section 60.

(Optical System According to a Fifth Modification of the Fourth Embodiment)

Figure 41:
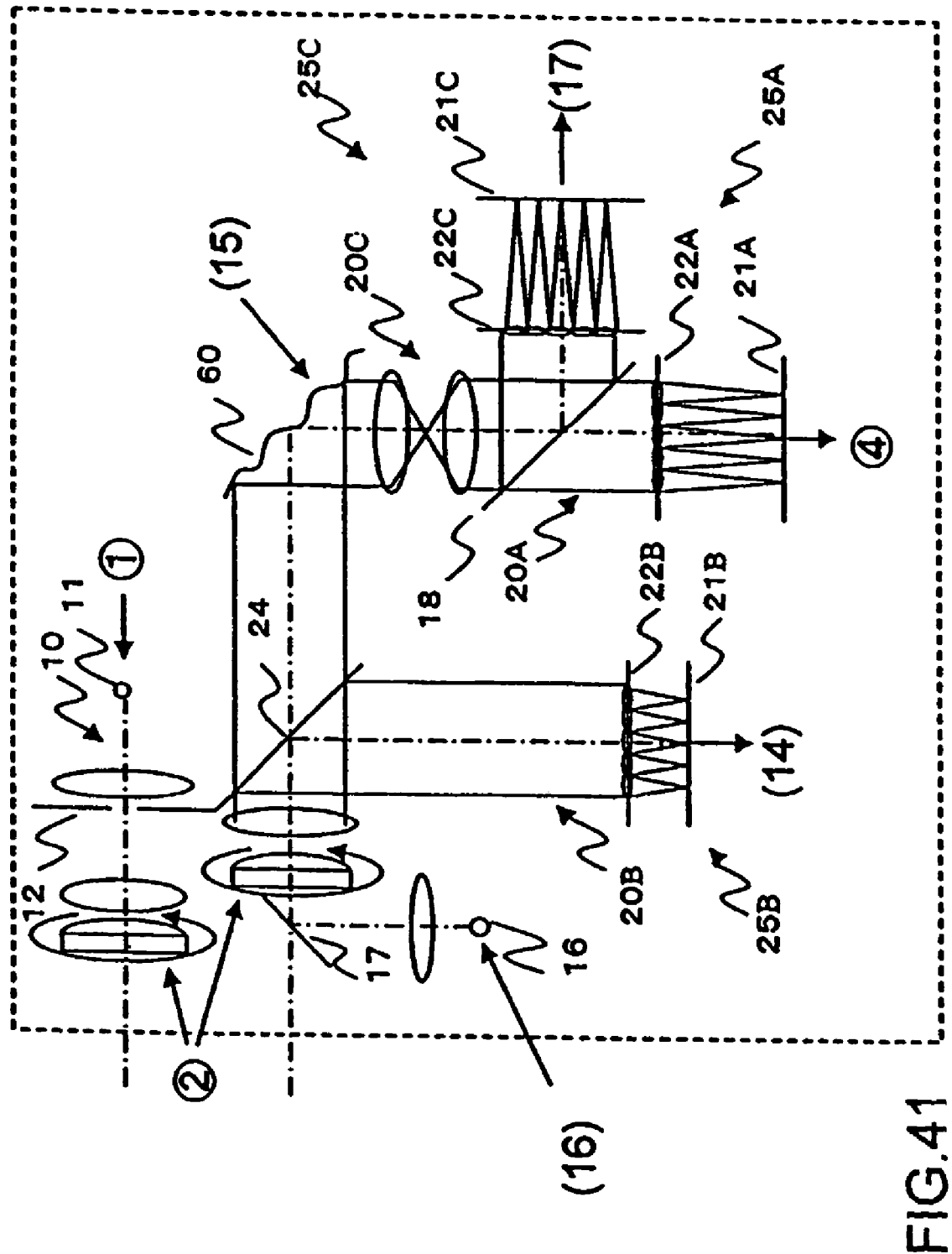
FIG. 41 is a view showing the structure of an optical system of an eye-characteristics measurement apparatus according to a fifth modification of the fourth embodiment.

FIG. 41 is a view showing the structure of an optical system of an eye-characteristics measurement apparatus according to a fifth modification of the fourth embodiment. FIG. 41 shows only a portion corresponding to a portion enclosed in a dotted line in FIG. 40, but the other portions are the same as in FIG. 40. The eye-characteristics measurement apparatus shown in FIG. 41 further includes a second measurement section 25B having a short focal length, a low sensitivity, and/or a high density, and a half mirror 24. In the optical system shown in FIG. 41, a first conversion member 22A is a wavefront conversion member having a lens section with a long focal length and/or a high sensitivity.

The structure of an electrical system according to the fifth modification of the fourth embodiment can be the same as the structure of the electrical system according to the fourth embodiment. A flowchart of aberration measurement which uses the optical system according to the fifth modification of the fourth embodiment can be, for example, the flowchart shown in FIG. 21.

(Optical System According to a Sixth Modification of the Fourth Embodiment)

Figure 42:
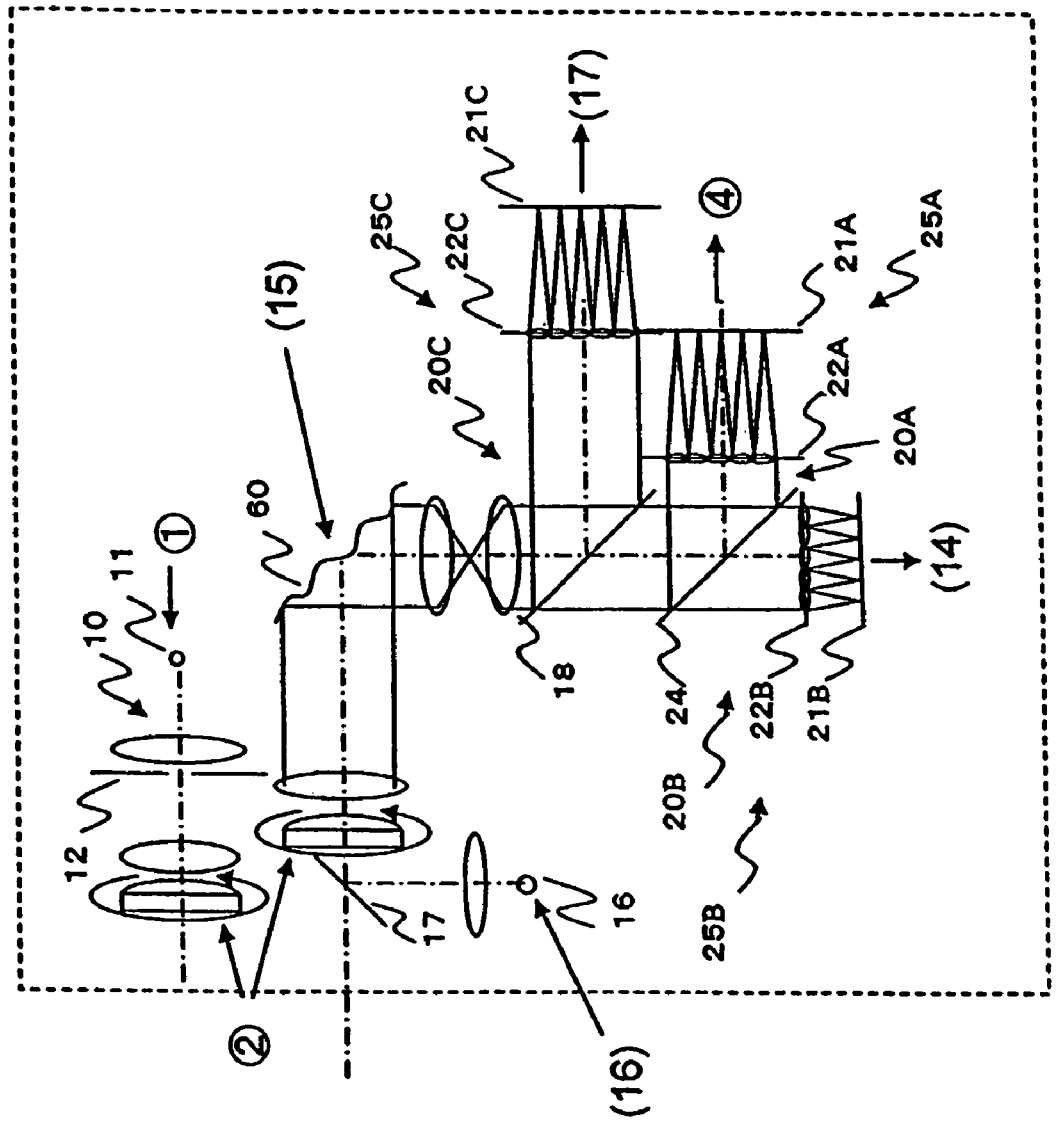
FIG. 42 is a view showing the structure of an optical system of an eye-characteristics measurement apparatus according to a sixth modification of the fourth embodiment.

FIG. 42 is a view showing the structure of an optical system of an eye-characteristics measurement apparatus according to a sixth modification of the fourth embodiment. FIG. 42 shows only a portion corresponding to the portion enclosed in the dotted line in FIG. 40, but the other portions are the same as in FIG. 40. In the eye-characteristics measurement apparatus shown in FIG. 42, a compensation optical section 60 is inserted in common into first, second, and third light-receiving optical systems 20A, 20B, and 20C. A light beam reflected and returned from the retina of an eye 100 under measurement passes a beam splitter 18 via the compensation optical section 60, is divided by a half mirror, and is led to first and second measurement sections 25A and 25B. Alternatively, instead of the half mirror 24, a mirror can be used and be moved and inserted into the optical path, so that the incidence of the light beam is switched between the first and second measurement sections 25A and 25B. A light beam emitted from a third light-source section 16 passes through the compensation optical section 60, is reflected by the beam splitter 18, and is led to a third measurement section 25C. Since the light beam is led to the second measurement section 25B through the compensation optical section 60, aberration obtained after compensation, and compensation aberration can be measured even in the second measurement section 25B. In addition, it is possible that the compensation optical section 60 is deformed until aberration measured at the output of the second measurement section 25B becomes equal to or smaller than an allowance specified in advance. The optical systems shown in FIG. 41 and FIG. 42 are described mainly as for single-path measurement, where a thin incident light beam is used. They can be changed for double-path measurement, if necessary.

The structure of an electrical system according to the sixth modification of the fourth embodiment can be the same as the structure of the electrical system according to the fourth embodiment. A flowchart of aberration measurement which uses the optical system according to the sixth modification of the fourth embodiment can, for example, be the flowchart shown in FIG. 21

(Fourth Modification of the Sixth Embodiment)

Figure 43:
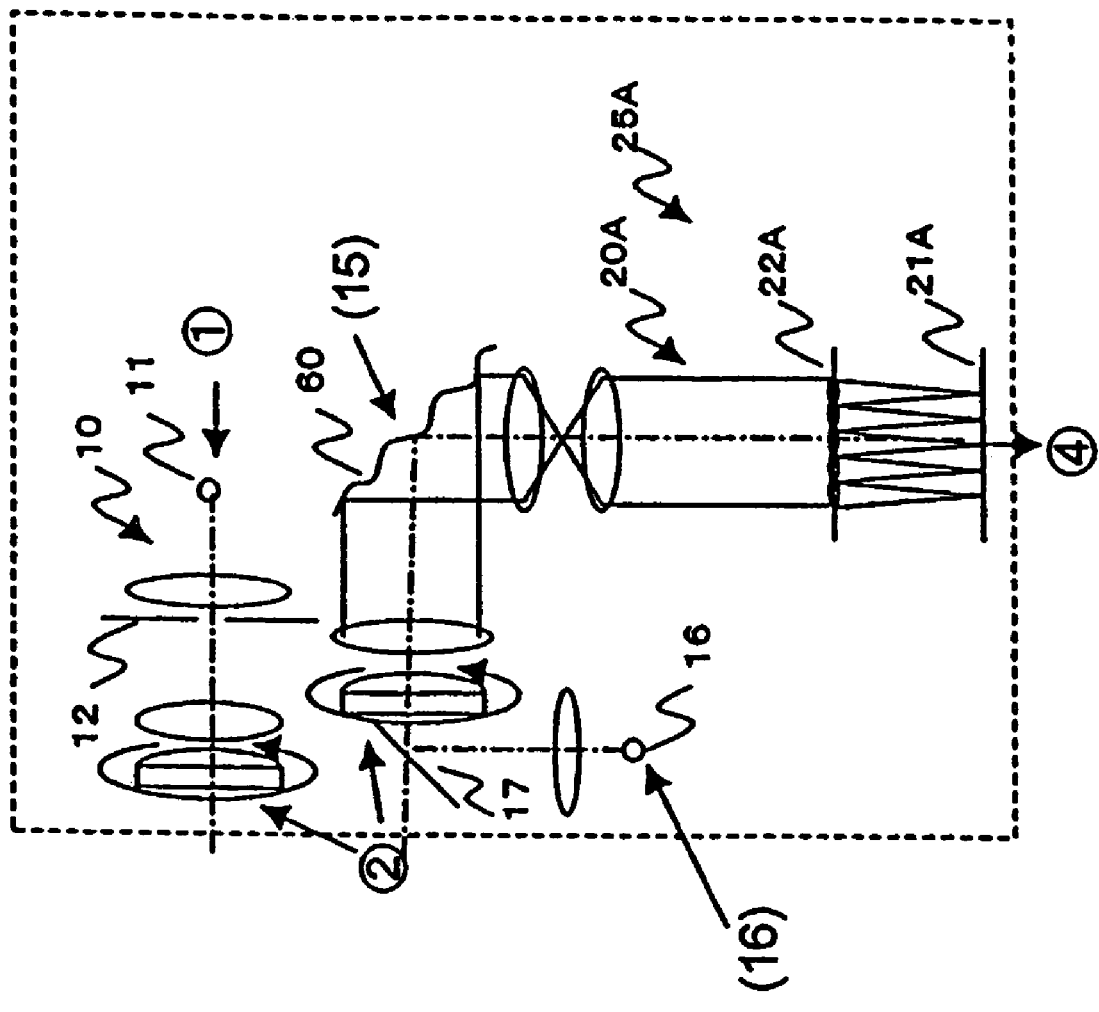
FIG. 43 is a view showing the structure of an optical system of an eye-characteristics measurement apparatus.

FIG. 43 is a view showing the structure of an optical system of an eye-characteristics measurement apparatus according to a fourth modification of the sixth embodiment. FIG. 43 shows the modification in which the first measurement section 25A for aberration measurement and the second measurement section 25B for compensation-aberration measurement used in FIG. 40 are made to one section. When the first light-source section 11 and the third light-source section 16 are alternately turned on, for example, a light beam reflected and returned from the eye 100 under measurement and a light beam emitted from the third light-source section 16 are switched and incident on the first light-receiving optical system 20A. A chopper may be provided before the first light-source section 11 and the third light-source section 16 to control a light beam incident on the first light-source optical system 20A. Instead of a chopper, appropriate means for blocking a light beam may be used. Since the detailed descriptions of the other portions are the same as those for FIG. 40, the same symbols are assigned and descriptions thereof are omitted. FIG. 43 shows only a portion corresponding to the portion enclosed in the dotted line in FIG. 40, but the other portions are the same as in FIG. 40.

The structure of an electrical system according to the fourth modification of the sixth embodiment can be the same as the structure of the electrical system according to the sixth embodiment. A flowchart of aberration measurement which uses the optical system according to the fourth modification of the sixth embodiment can, for example, be the flowchart shown in FIG. 16.

(Fifth Modification of the Sixth Embodiment)

Figure 44:
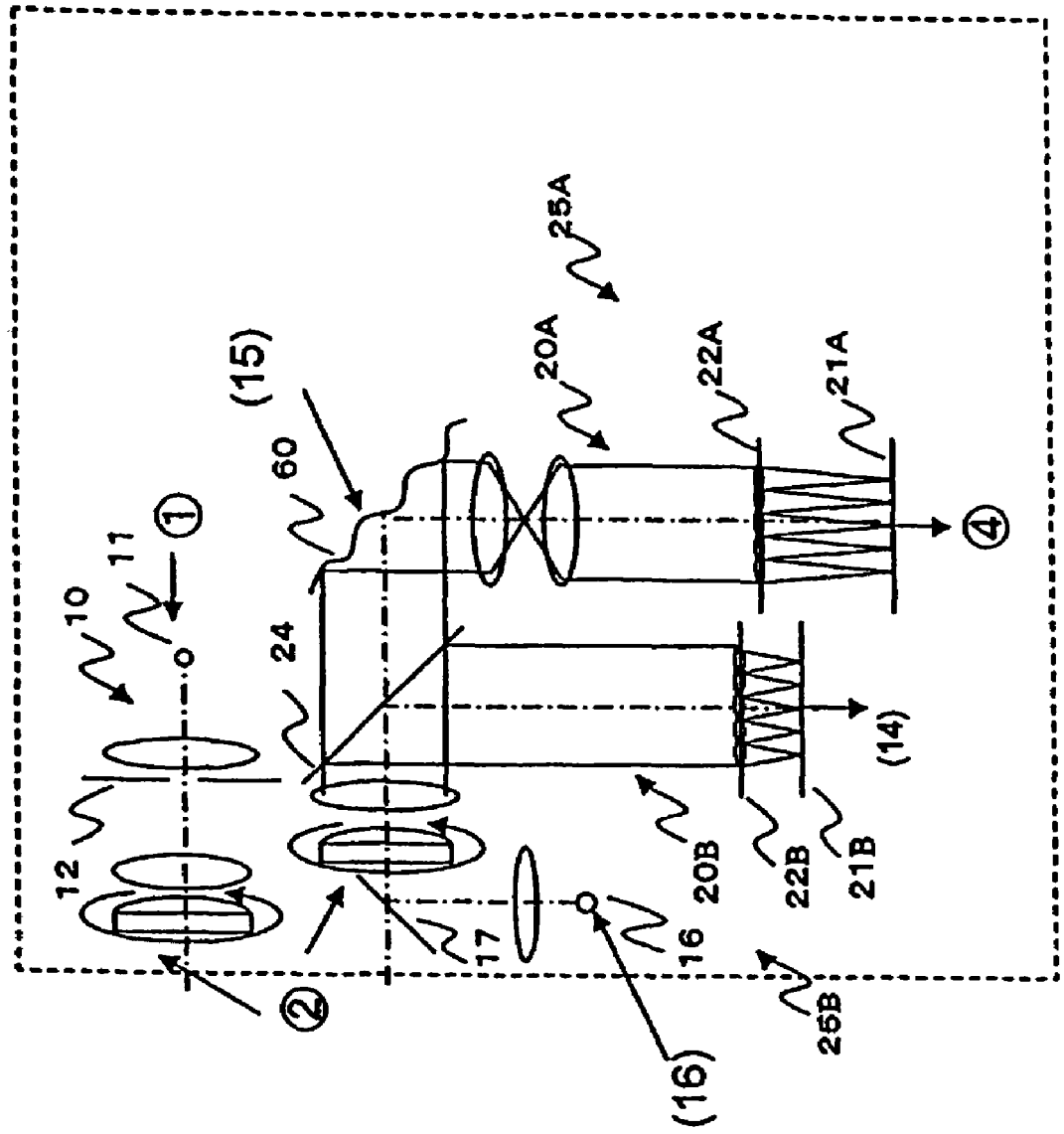
FIG. 44 is a view showing the structure of an optical system of an eye-characteristics measurement apparatus according to a fifth modification of the sixth embodiment.

FIG. 44 is a view showing the structure of an optical system of an eye-characteristics measurement apparatus according to a fifth modification of the sixth embodiment. FIG. 44 shows the modification in which the first measurement section 25A for aberration measurement and the third measurement section 25C for compensation-aberration measurement used in FIG. 41 are made to one section. When the first light-source section 11 and the third light-source section 16 are alternately turned on, for example, a light beam reflected and returned from the eye 100 under measurement and a light beam emitted from the third light-source section 16 are switched and incident on the first light-receiving section 21A. Light-beam blocking means, such as a chopper, may be provided before the first light-source section 11 and the third light-source section 16 to control a light beam incident on the first light-receiving optical system 20A and the second light-receiving optical system 20B. Since the detailed descriptions of the other portions are the same as those for FIG. 41, the same symbols are assigned and descriptions thereof are omitted. FIG. 44 shows only a portion corresponding to the portion enclosed in the dotted line in FIG. 40, but the other portions are the same as in FIG. 40.

The structure of an electrical system according to the fifth modification of the sixth embodiment can be the same as the structure of the electrical system according to the sixth embodiment. A flowchart of aberration measurement which uses the optical system according to the fifth modification of the sixth embodiment can, for example, be the flowchart shown in FIG. 25.

(Sixth Modification of the Sixth Embodiment)

Figure 45:
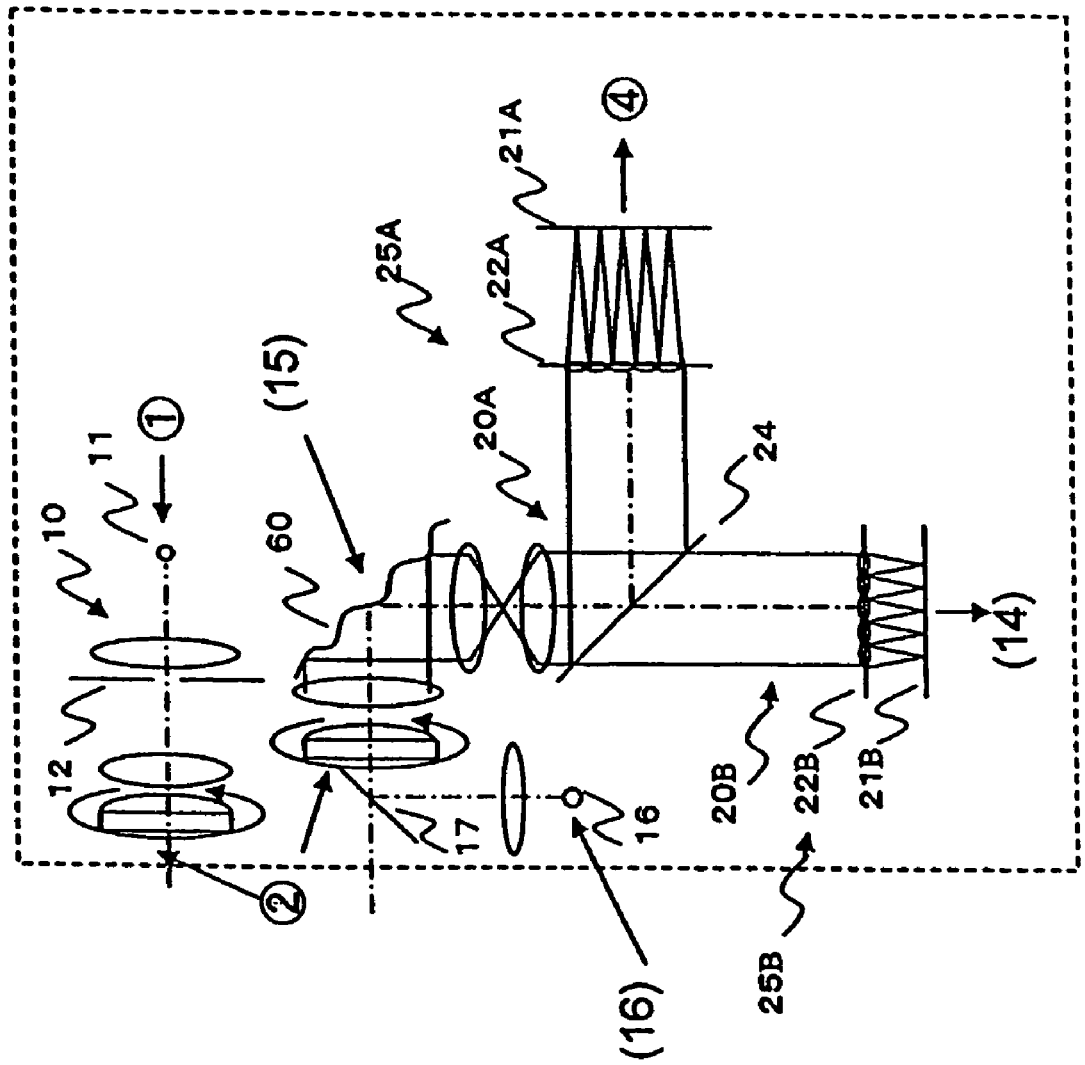
FIG. 45 is a view showing the structure of an optical system of an eye-characteristics measurement apparatus according to a sixth modification of the sixth embodiment.

FIG. 45 is a view showing the structure of an optical system of an eye-characteristics measurement apparatus according to a sixth modification of the sixth embodiment. FIG. 45 shows the modification in which the first measurement section 25A for aberration measurement and the second measurement section 25*b* for compensation-aberration measurement used in FIG. 42 are made to one section. Measurement is performed by switching a light beam incident on the first light-receiving optical 20A in the same way as in the fourth modification of the sixth embodiment. Since the detailed descriptions of the other portions are the same as those for FIG. 42, the same symbols are assigned and descriptions thereof are omitted. FIG. 45 shows only a portion corresponding to the portion enclosed in the dotted line in FIG. 40, but the other portions are the same as in FIG. 40.

The structure of an electrical system according to the sixth modification of the sixth embodiment can be the same as the structure of the electrical system according to the sixth embodiment. A flowchart of aberration measurement which uses the optical system according to the sixth modification of the sixth embodiment can, for example, be the flowchart shown in FIG. 16.

Figure 46:
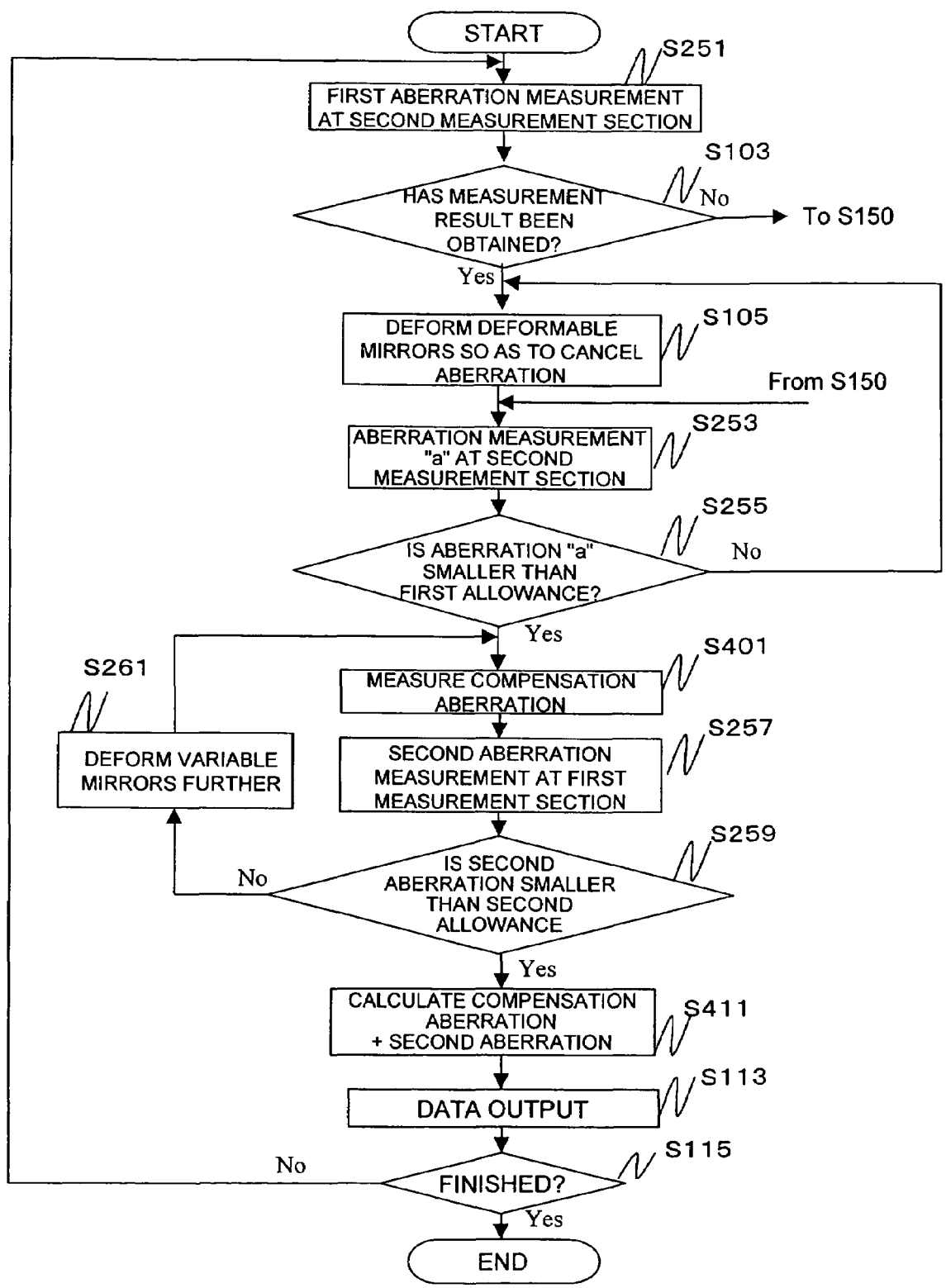
FIG. 46 is a modification of the flowchart of aberration measurement according to the fourth embodiment.

FIG. 46 is a second modification of the flowchart of aberration measurement according to the fourth embodiment. In the present modification, the optical system shown in FIG. 42 or FIG. 20 is used, a light beam compensated for aberration is received by the second light-receiving section 21B, and compensation is performed such that aberration obtained according to a signal sent from the second light-receiving section 21B is equal to or smaller than an allowance specified in advance.

First, the calculation section 600 executes the processes of steps S251, S103, and S105. The details of the processes are the same as those described above, and a description thereof is omitted. Then, the calculation section 600 measures aberration obtained after the compensation, according to a signal at the second measurement section 25B (S253). The details of this process is the same as those in step S251, described above, and a description thereof is omitted. The calculation section 600 determines (S255) whether the aberration obtained in step S253 is equal to or smaller than a first allowance specified in advance. For example, the calculation section 600 may determine whether the RMS value of higher-order aberration is equal to or smaller than 0.1. When the aberration is larger than the first allowance, the calculation section 600 goes back to step S105, and further deforms the compensation optical section 60. When the aberration is smaller than the first allowance, the calculation section 600 proceeds to the process of step S401.

Instead of determining whether the aberration is equal to or smaller than the first allowance, the calculation section 600 may receive the first signal from the first light-receiving section 21A and determine whether measurement based on the first signal is possible. For example, the calculation section 600 can determine that measurement based on the first signal is impossible, according to one or a plurality of conditions determined in advance, such as that the number of centers of gravity of the point images based on the received first signal, obtained is less than a predetermined value (for example, less than one third the predetermined value), that each point image has a large blur (for example, has a blur 20 times or more that obtained when there is no aberration), or that the number of points which cannot be separated from an adjacent spot image and therefore cannot be detected is not less than a predetermined value. The determination condition may be any appropriate condition. When the calculation section 600 determines that measurement is impossible, the processing proceeds to the process of step S105. When the calculation section 600 determines that measurement is possible, the processing proceeds to the process of step S401.

The calculation section 600 executes the processes of steps S401 and S257. The details of the processes are the same as those described above, and a description thereof is omitted. Then, the calculation section determines (S259) whether the aberration 2 obtained in step S257 is equal to or smaller than a second allowance determined in advance. For example, the calculation section 600 may determine whether the RMS value of higher-order aberration is equal to or smaller than 0.1. The first allowance and the second allowance can be different values. For example, with measurement sensitivity taken into account, the first allowance may be equal to or larger than the second allowance. When the aberration 2 is larger than the second allowance (S259), the calculation section 600 further deforms the compensation optical section 60 according to the aberration 2 (S261), and goes back to step S401. The details of the process for deforming the compensation optical section 60 is the same as those in step S105. When the aberration 2 is smaller than the second allowance, the calculation section 600 proceeds to the process of step S411.

Then, the calculation section 600 executes the processes of steps S111, S113, and S115. The details of the processes are the same as those described above, and a description thereof is omitted.

INDUSTRIAL APPLICABILITY

According to the present invention, a precise eye-characteristics measurement apparatus having a wide measurement range and capable of performing correct measurement even if there is much aberration can be provided. According to the present invention, an eye 100 under measurement can be illuminated in an appropriate illumination state. Further, according to the present invention, an eye-characteristics measurement apparatus for precisely measuring the optical characteristics of the eye 100 under measurement by applying compensation to cancel aberration and further by measuring the amount of aberration after the compensation can be provided. According to the present invention, an eye-characteristics measurement apparatus for measuring optical characteristics more precisely and more quickly by applying compensation to cancel aberration included in measurement light and further by using low-sensitivity and high-sensitivity optical systems can be provided. Furthermore, according to the present invention, more correct measurement with the difference between a value input to cancel aberration and aberration actually compensated for being taken into account can be performed.

The invention claimed is:

1. An eye-characteristics measurement apparatus comprising:
   a first light-source section for emitting a light beam having a first wavelength;
   a first illumination optical system for illuminating a minute area on the retina of an eye under measurement, with a light beam emitted from the first light-source section;
   a compensation optical section for compensating for aberration of a light beam transmitted or reflected, according to the amount of compensation given based on an optical characteristic of a reflected light beam which is reflected and returned from the retina of the eye under measurement;
   a first light-receiving optical system for receiving a part of the reflected light beam which is reflected and returned from the retina of the eye under measurement, through the compensation optical section and a first conversion member having a long focal length or a high sensitivity for converting to at least substantially 17 beams;
   a first light-receiving section for receiving a light beam received by the first light-receiving optical system;
   a third light-source section for illuminating the compensation optical section with a light beam having a third wavelength;
   a third light-receiving optical system for receiving a light beam emitted from the third light-source section, through the compensation optical section and a third conversion member for converting to at least substantially 17 beams;
   a third light-receiving section for receiving a light beam received by the third light-receiving optical system;
   a second light-receiving optical system for receiving a part of the reflected light beam which is reflected and returned from the retina of the eye under measurement, through the compensation optical section and a second conversion member having a short focal length, a low sensitivity, or a high density for converting to at least substantially 17 beams;
   a second light-receiving section for receiving a light beam received by the second light-receiving optical system;
   a compensation-amount calculation section for obtaining an optical characteristic of the eye under measurement based on the output of the second light-receiving section, for obtaining the amount of compensation based on the optical characteristic, and for outputting the amount of compensation to the compensation optical section; and
   a measurement calculation section for measuring an optical characteristic compensated by the compensation optical section based on the output of the third light-receiving section and an optical characteristic based on the output of the first light-receiving section, obtained after the compensation of the compensation optical section, and for obtaining an optical characteristic of the eye under measurement according to the measured optical characteristics.

2. An eye-characteristics measurement apparatus comprising:
   a first light-source section for emitting a light beam having a first wavelength;
   a first illumination optical system for illuminating a minute area on the retina of an eye under measurement, with a light beam emitted from the first light-source section;
   a compensation optical section for compensating for aberration of a light beam transmitted or reflected, according to the amount of compensation given based on an optical characteristic of a reflected light beam which is reflected and returned from the retina of the eye under measurement;
   a third light-source section for illuminating the compensation optical section with a light beam having a third wavelength;
   a first light-receiving optical system for receiving a part of the reflected light beam which is reflected and returned from the retina of the eye under measurement and the light beam emitted from the third light-source section, through the compensation optical section and a first conversion member having a long focal length or a high sensitivity for converting to at least substantially 17 beams;
   a first light-receiving section for receiving a light beam received by the first light-receiving optical system;
   a second light-receiving optical system for receiving a part of the reflected light beam which is reflected and returned from the retina of the eye under measurement, through the compensation optical section and a second conversion member having a short focal length, a low sensitivity, or a high density for converting to at least substantially 17 beams;
   a second light-receiving section for receiving a light beam received by the second light-receiving optical system;
   a compensation-amount calculation section for obtaining an optical characteristic of the eye under measurement based on the output of the second light-receiving section, for obtaining the amount of compensation based on the optical characteristic, and for outputting the amount of compensation to the compensation optical section; and a measurement calculation section for measuring an optical characteristic compensated by the compensation optical section based on the output of the first light-receiving section caused by the light beam emitted from the third light-source section, for measuring an optical characteristic obtained after the compensation of the compensation optical section based on the output of the first light-receiving section caused by the light beam emitted from the first light-source section, and for obtaining an optical characteristic of the eye under measurement according to the measured optical characteristics.

3. An eye-characteristics measurement apparatus comprising:

a first light-source section for emitting a light beam having a first wavelength;

a first illumination optical system for illuminating a minute area on the retina of an eye under measurement, with a light beam emitted from the first light-source section;

a first light-receiving optical system for receiving a part of a reflected light beam which is reflected and returned from the retina of the eye under measurement, through a first conversion member having a long focal length or a high sensitivity for converting to at least substantially 17 beams;

a second light-receiving optical system for receiving a part of the reflected light beam which is reflected and returned from the retina of the eye under measurement, through a second conversion member having a short focal length, a low sensitivity, or a high density for converting to at least substantially 17 beams;

a first light-receiving section for receiving a light beam received by the first light-receiving optical system;

a second light-receiving section for receiving a light beam received by the second light-receiving optical system;

a compensation-amount calculation section for obtaining an optical characteristic of the eye under measurement based on the output of the first light-receiving section and/or the second light-receiving section, and for obtaining and outputting the amount of compensation required to cancel aberration based on the optical characteristic;

a compensation optical section for applying aberration compensation based on the amount of compensation output from the compensation-amount calculation section to the reflected light beam from the retina of the eye under measurement, or to both an illumination light beam coming from the first illumination optical system and the reflected light beam from the retina of the eye under measurement; and a measurement calculation section for obtaining an optical characteristic of the eye under measurement according to an optical characteristic based on the output of the first light-receiving section and/or the second light-receiving section, obtained after the compensation of the compensation optical section, and an optical characteristic compensated by the compensation optical section.

4. An eye-characteristics measurement apparatus according to claim 3, wherein the second light-receiving optical system is configured so as to be able to perform signal processing more easily and quickly due to a setting in which the change of a beam converted by the second conversion member over a measurement possible area is set smaller than the conversion pitch of the second conversion member.

5. An eye-characteristics measurement apparatus according to claim 3, wherein the compensation-amount calculation section obtains the optical characteristic of the eye under measurement based on the output of the second light-receiving section, and obtains and outputs the amount of compensation required to cancel aberration based on the optical characteristic, and the measurement calculation section is configured so as to obtain the optical characteristic of the eye under measurement at a high sensitivity based on the optical characteristic based on the output of the first light-receiving section and the optical characteristic compensated by the compensation optical section.

6. An eye-characteristics measurement apparatus according to claim 3, further comprising:

a third light-source section for emitting a light beam to illuminate the compensation optical section;

a third light-receiving optical system for receiving a light beam emitted from the third light-source section, through the compensation optical section and a third conversion member for converting to at least substantially 17 beams;

a third light-receiving section for receiving a light beam received by the third light-receiving optical system, wherein the measurement calculation section is configured so as to measure the optical characteristic compensated by the compensation optical section, based on the output of the third light-receiving section and to obtain the optical characteristic of the eye under measurement by using the measured optical characteristic.

7. An eye-characteristics measurement apparatus according to claim 6, wherein the wavelength of a light beam emitted from the third light-source section is different from the first wavelength of the first light-source section, and the measurement calculation section is configured so as to measure in parallel the optical characteristic based on the output of the first light-receiving section, obtained after the compensation of the compensation optical section and the optical characteristic compensated by the compensation optical section based on the output of the third light-receiving section.

8. An eye-characteristics measurement apparatus according to claim 3, further comprising a third light-source section for emitting a light beam to illuminate the compensation optical section, wherein the first light-receiving section further receives a light beam emitted from the third light-source section, through the compensation optical section and the first conversion member, and the measurement calculation section is configured so as to measure the optical characteristic compensated by the compensation optical section, based on the output of the first light-receiving section caused by a light beam emitted from the third light-source section, and to use the measured optical characteristic to obtain the optical characteristic of the eye under measurement.

9. An eye-characteristics measurement apparatus according to claim 8, wherein the measurement calculation section turns on and off the first and third light-source sections or inserts light-beam blocking means in an optical path coming from the first and third light-source section to switch or select the light beam to be received by the first light-receiving section.

10. An eye-characteristics measurement apparatus according to claim 6, wherein
the third light-source section is formed of a light source common with the first light-source section, and
a part of a light beam emitted from the first light-source section is used as a light beam emitted from the third light-source section.

11. An eye-characteristics measurement apparatus comprising:
a first light-source section for emitting a light beam having a first wavelength;
a first illumination optical system for illuminating a minute area on the retina of an eye under measurement, with a light beam emitted from the first light-source section;
a first light-receiving optical system for receiving a part of a reflected light beam which is reflected and returned from the retina of the eye under measurement, through a first conversion member for converting to at least substantially 17 beams;
a first light-receiving section for receiving a light beam received by the first light-receiving optical system;
a second light-source section for emitting a light beam having a second wavelength;
an eye-front-part illumination section for illuminating a portion close to the retina of the eye under measurement at a predetermined pattern with a light beam emitted from the second light-source section;
an eye-front-part observation section for receiving a reflected light beam which is reflected and returned from the portion close to the retina of the eye under measurement;
an eye-front-part-image light-receiving section for receiving a light beam received by the eye-front-part observation section;
a compensation-amount calculation section for obtaining an optical characteristic of the eye under measurement based on the output of the eye-front-part-image light-receiving section, and for obtaining and outputting the amount of compensation required to cancel aberration based on the optical characteristic;
a compensation optical section for applying aberration compensation based on the amount of compensation output from the compensation-amount calculation section to the reflected light beam from the retina of the eye under measurement, or to both an illumination light beam coming from the first illumination optical system and the reflected light beam from the retina of the eye under measurement; and
a measurement calculation section for obtaining an optical characteristic of the eye under measurement according to an optical characteristic based on the output of the first light-receiving section, obtained after the compensation of the compensation optical section, and an optical characteristic compensated by the compensation optical section.

12. An eye-characteristics measurement apparatus according to claim 11, wherein the measurement calculation section is configured so as to further obtain the shape of the cornea of the eye under measurement based on the output of the eye-front-part-image light receiving section.

13. An eye-characteristics measurement apparatus according to claim 11, further comprising:
a third light-source section for emitting a light beam to illuminate the compensation optical section;
a third light-receiving optical system for receiving a light beam emitted from the third light-source section, through the compensation optical section and a third conversion member for converting to at least substantially 17 beams; and
a third light-receiving section for receiving a light beam received by the third light-receiving optical system,
wherein the measurement calculation section is configured so as to measure the optical characteristic compensated by the compensation optical section, based on the output of the third light-receiving section and to obtain the optical characteristic of the eye under measurement by using the measured optical characteristic.

14. An eye-characteristics measurement apparatus according to claim 13, wherein
the wavelength of a light beam emitted from the third light-source section is different from the first wavelength of the first light-source section, and
the measurement calculation section is configured so as to measure in parallel the optical characteristic based on the output of the first light-receiving section, obtained after the compensation of the compensation optical section and the optical characteristic compensated by the compensation optical section based on the output of the third light-receiving section.

15. An eye-characteristics measurement apparatus according to claim 11, further comprising a third light-source section for emitting a light beam to illuminate the compensation optical section,
wherein the first light-receiving section further receives a light beam emitted from the third light-source section, through the compensation optical section and the first conversion member, and
the measurement calculation section is configured so as to measure the optical characteristic compensated by the compensation optical section, based on the output of the first light-receiving section caused by a light beam emitted from the third light-source section, and to use the measured optical characteristic to obtain the optical characteristic of the eye under measurement.

16. An eye-characteristics measurement apparatus according to claim 15, wherein the measurement calculation section turns on and off the first and third light-source sections or inserts light-beam blocking means in an optical path coming from the first and third light-source sections to switch the light beam to be received by the first light-receiving section.

17. An eye-characteristics measurement apparatus according to claim 13, wherein
the third light-source section is formed of a light source common with the first light-source section, and
a part of a light beam emitted from the first light-source section is used as a light beam emitted from the third light-source section.

18. An eye-characteristics measurement apparatus comprising:
a first light-source section for emitting a light beam having a first wavelength;
a first illumination optical system for illuminating a minute area on the retina of an eye under measurement, with a light beam emitted from the first light-source section;
a first light-receiving optical system for receiving a part of a reflected light beam which is reflected and returned from the retina of the eye under measurement, through a first conversion member for converting to at least substantially 17 beams;
a first light-receiving section for receiving a light beam received by the first light-receiving optical system;
a compensation-amount calculation section for obtaining an optical characteristic of the eye under measurement based on the output of the first light-receiving section, and for obtaining and outputting the amount of compensation required to cancel aberration based on the optical characteristic;

a compensation optical section for applying aberration compensation based on the amount of compensation output from the compensation-amount calculation section to the reflected light beam from the retina of the eye under measurement, or to both an illumination light beam coming from the first illumination optical system and the reflected light beam from the retina of the eye under measurement;

a third light-source section for emitting a light beam to illuminate the compensation optical section;

a third light-receiving optical system for receiving a light beam emitted from the third light-source section, through the compensation optical section and a third conversion member for converting to at least substantially 17 beams;

a third light-receiving section for receiving a light beam received by the third light-receiving optical system; and a measurement calculation section for measuring an optical characteristic based on the output of the first light-receiving section, obtained after the compensation of the compensation optical section, and an optical characteristic compensated by the compensation optical section based on the output of the third light-receiving section, and for obtaining an optical characteristic of the eye under measurement according to the measured optical characteristics.

19. An eye-characteristics measurement apparatus according to claim 18, wherein the wavelength of a light beam emitted from the third light-source section is different from the first wavelength of the first light-source section, and the measurement calculation section is configured so as to measure in parallel the optical characteristic based on the output of the first light-receiving section, obtained after the compensation of the compensation optical section and the optical characteristic compensated by the compensation optical section based on the output of the third light-receiving section.

20. An eye-characteristics measurement apparatus according to claim 18, wherein the third light-source section is formed of a light source common with the first light-source section, and a part of a light beam emitted from the first light-source section is used as a light beam emitted from the third light-source section.

21. An eye-characteristics measurement apparatus comprising:

a first light-source section for emitting a light beam having a first wavelength;

a first illumination optical system for illuminating a minute area on the retina of an eye under measurement, with a light beam emitted from the first light-source section;

a third light-source section for emitting a light beam used for measuring aberration compensated for;

a first light-receiving optical system for receiving a part of a reflected light beam which is reflected and returned from the retina of the eye under measurement and a light beam emitted from the third light-receiving section, through a first conversion member for converting to at least substantially 17 beams;

a first light-receiving section for receiving a light beam received by the first light-receiving optical system;

a compensation-amount calculation section for obtaining an optical characteristic of the eye under measurement based on the output of the first light-receiving section, and for obtaining and outputting the amount of compensation required to cancel aberration based on the optical characteristic;

a compensation optical section for applying aberration compensation based on the amount of compensation output from the compensation-amount calculation section to the reflected light beam from the retina of the eye under measurement and a light beam coming from the third light-source section, or to an illumination light beam coming from the first illumination optical system, the reflected light beam from the retina of the eye under measurement, and the light beam coming from the third light-source section; and a measurement calculation section for measuring an optical characteristic compensated by the compensation optical section based on the output of the first light-receiving section caused by the light beam emitted from the third light-source section, for measuring an optical characteristic obtained after the compensation of the compensation optical section based on the output of the first light-receiving section caused by the light beam emitted from the first light-source section, and for obtaining an optical characteristic of the eye under measurement according to the measured optical characteristics.

22. An eye-characteristics measurement apparatus according to claim 21, wherein the measurement calculation section turns on and off the first and third light-source sections or inserts light-beam blocking means in an optical path coming from the first and third light-source sections to switch or select the light beam to be received by the first light-receiving section.

23. An eye-characteristics measurement apparatus according to claim 21, wherein the third light-source section is formed of a light source common with the first light-source section, and a part of a light beam emitted from the first light-source section is used as a light beam emitted from the third light-source section.

24. An eye-characteristics measurement apparatus according to claim 1, wherein the compensation optical section comprises a first compensation optical section for applying aberration compensation to an illumination light beam coming from the first illumination optical system, and a second compensation optical section for applying aberration compensation to the reflection light beam from the retina of the eye under measurement.

25. An eye-characteristics measurement apparatus according to claim 24, further comprising:

a fourth light-receiving optical system for receiving a part of a light beam emitted from the first light-source section, through the first compensation optical section and a fourth conversion member for converting to at least substantially 17 beams; and a fourth light-receiving section for receiving a light beam received by the fourth light-receiving optical system, wherein the third light-source section illuminates the second compensation optical section;

the third light-receiving section receives a light beam emitted from the third light-source section, through the second compensation optical section and the third conversion member; and the measurement calculation section is configured so as to further measure the optical characteristic compensated by the second compensation optical section based on the output of the third light-receiving section and to use the measured optical characteristic to obtain the optical characteristic of the eye under measurement.

26. An eye-characteristics measurement apparatus according to claim 1, wherein the compensation-amount calculation section is configured so as to be able to compensate for a spherical-power component, which is a lower-order aberration, based on the optical characteristic of the eye under measurement by moving the first illumination optical system and/or the first light-receiving optical system.

27. An eye-characteristics measurement apparatus according to claim 1, wherein the compensation-amount calculation section is configured such that a spherical-power component and/or an astigmatic component, which are lower-order aberrations, is compensated for by moving the first light-receiving optical system and/or changing the state of a part of the elements of the first light-receiving optical system, and the compensation optical section performs compensation including at least a higher-order component of the other optical characteristics.

28. An eye-characteristics measurement apparatus according to claim 1, wherein the compensation optical section is configured so as to perform compensation including at least a higher-order component of the optical characteristic of the eye under measurement.

29. An eye-characteristics measurement apparatus according to claim 1, wherein the compensation optical section is formed of at least either a liquid-crystal spatial optical modulator or a deformable mirror.

30. An eye-characteristics measurement apparatus according to claim 1, wherein the optical characteristic of the eye under measurement is displayed after the compensation of the compensation optical section, and aberration is further compensated for by the compensation-amount calculation section and the compensation optical section according to an instruction from an input section.

31. An eye-characteristics measurement apparatus according to claim 1, wherein the compensation-amount calculation section is configured so as to obtain the amount of compensation such that the obtained optical characteristic of the eye under measurement is not completely canceled.

32. An eye-characteristics measurement apparatus according to claim 1, wherein the first illumination optical system is configured so as to illuminate the minute area on the retina of the eye under measurement with a wide beam when passing through the cornea of the eye under measurement by a light beam emitted from the first light-source section.

33. An eye-characteristics measurement apparatus according to claim 1, wherein the first illumination optical system is configured so as to illuminate the minute area on the retina of the eye under measurement with a narrow beam by a light beam emitted from the first light-source section.

34. An eye-characteristics measurement apparatus according to claim 33, wherein the first illumination optical system comprises a light-beam incident-position change section capable of changing the position where the narrow beam for illumination is incident on an eye-front-part of the eye under measurement, in a direction perpendicular to the optical axis.

35. An eye-characteristics measurement apparatus according to claim 18, wherein the compensation optical section comprises
a first compensation optical section for applying aberration compensation to an illumination light beam coming from the first illumination optical system, and
a second compensation optical section for applying aberration compensation to the reflection light beam from the retina of the eye under measurement.

36. An eye-characteristics measurement apparatus according to claim 35, further comprising:
a fourth light-receiving optical system for receiving a part of a light beam emitted from the first light-source section, through the first compensation optical section and a fourth conversion member for converting to at least substantially 17 beams; and
a fourth light-receiving section for receiving a light beam received by the fourth light-receiving optical system,
wherein the third light-source section illuminates the second compensation optical section;
the third light-receiving section receives a light beam emitted from the third light-source section, through the second compensation optical section and the third conversion member; and
the measurement calculation section is configured so as to further measure the optical characteristic compensated by the second compensation optical section based on the output of the third light-receiving section and to use the measured optical characteristic to obtain the optical characteristic of the eye under measurement.

37. An eye-characteristics measurement apparatus according to claim 18, wherein the compensation-amount calculation section is configured so as to be able to compensate for a spherical-power component, which is a lower-order aberration, based on the optical characteristic of the eye under measurement by moving the first illumination optical system and/or the first light-receiving optical system.

38. An eye-characteristics measurement apparatus according to claim 18, wherein the compensation-amount calculation section is configured such that a spherical-power component and/or an astigmatic component, which are lower-order aberrations, is compensated for by moving the first light-receiving optical system and/or changing the state of a part of the elements of the first light-receiving optical system, and the compensation optical section performs compensation including at least a higher-order component of the other optical characteristics.

39. An eye-characteristics measurement apparatus according to claim 18, wherein the compensation optical section is configured so as to perform compensation including at least a higher-order component of the optical characteristic of the eye under measurement.

40. An eye-characteristics measurement apparatus according to claim 18, wherein the compensation optical section is formed of at least either a liquid-crystal spatial optical modulator or a deformable mirror.

41. An eye-characteristics measurement apparatus according to claim 18, wherein the optical characteristic of the eye under measurement is displayed after the compensation of the compensation optical section, and aberration is further compensated for by the compensation-amount calculation section and the compensation optical section according to an instruction from an input section.

42. An eye-characteristics measurement apparatus according to claim 18, wherein the compensation-amount calculation section is configured so as to obtain the amount of compensation such that the obtained optical characteristic of the eye under measurement is not completely canceled.

43. An eye-characteristics measurement apparatus according to claim 18, wherein the first illumination optical system is configured so as to illuminate the minute area on the retina of the eye under measurement with a wide beam when passing through the cornea of the eye under measurement by a light beam emitted from the first light-source section.

44. An eye-characteristics measurement apparatus according to claim 18, wherein the first illumination optical system is configured so as to illuminate the minute area on the retina of the eye under measurement with a narrow beam by a light beam emitted from the first light-source section.

45. An eye-characteristics measurement apparatus according to claim 44, wherein the first illumination optical system comprises a light-beam incident-position change section capable of changing the position where the narrow beam for illumination is incident on an eye-front-part of the eye under measurement, in a direction perpendicular to the optical axis.

* * * * *